US009446017B2

(12) United States Patent
Hsu

(10) Patent No.: US 9,446,017 B2
(45) Date of Patent: Sep. 20, 2016

(54) COMPOSITIONS AND METHODS FOR TREATING HERPES SIMPLEX VIRUS

(75) Inventor: Stephen D. Hsu, Evans, GA (US)

(73) Assignee: Augusta University Research Institute, Inc., Augusta, GA (US)

(*) Notice: Subject to any disclaimer, the term of this patent is extended or adjusted under 35 U.S.C. 154(b) by 0 days.

(21) Appl. No.: 13/177,041

(22) Filed: Jul. 6, 2011

(65) Prior Publication Data

US 2012/0172423 A1 Jul. 5, 2012

Related U.S. Application Data

(63) Continuation-in-part of application No. 12/063,139, filed as application No. PCT/US2006/031120 on Aug. 10, 2006, now Pat. No. 8,076,484.

(60) Provisional application No. 61/361,752, filed on Jul. 6, 2010, provisional application No. 60/707,234, filed on Aug. 11, 2005.

(51) Int. Cl.
*A01N 43/16* (2006.01)
*A61K 31/35* (2006.01)
*A61K 31/353* (2006.01)

(52) U.S. Cl.
CPC .................................... *A61K 31/353* (2013.01)

(58) Field of Classification Search
CPC ... A61K 31/353; A61K 31/43; A61K 31/496; A61K 31/546; A61K 31/65; A61K 31/7036; A61K 31/7048; A61K 36/82; A61K 38/12
USPC .......................................................... 514/456
See application file for complete search history.

(56) References Cited

U.S. PATENT DOCUMENTS

| | | | | |
|---|---|---|---|---|
| 4,235,871 | A | | 11/1980 | Papahadjopoulos |
| 4,501,728 | A | | 2/1985 | Geho |
| 4,522,811 | A | | 6/1985 | Eppstein |
| 4,624,665 | A | | 11/1986 | Nuwayser |
| 4,655,767 | A | | 4/1987 | Woodard |
| 4,687,481 | A | | 8/1987 | Nuwayser |
| 4,797,284 | A | | 1/1989 | Loper |
| 4,810,499 | A | | 3/1989 | Nuwayser |
| 4,834,978 | A | | 5/1989 | Nuwayser |
| 4,837,028 | A | | 6/1989 | Allen |
| 4,877,618 | A | | 10/1989 | Reed, Jr. |
| 4,880,663 | A | | 11/1989 | Shimada |
| 4,917,895 | A | | 4/1990 | Lee |
| 4,920,016 | A | | 4/1990 | Allen |
| 4,927,687 | A | | 5/1990 | Nuwayser |
| 4,956,171 | A | | 9/1990 | Chang |
| 5,019,369 | A | | 5/1991 | Presant |
| 5,035,894 | A | | 7/1991 | Lee |
| 5,073,372 | A | | 12/1991 | Turner |
| 5,087,445 | A | | 2/1992 | Haffey |
| 5,091,186 | A | | 2/1992 | Miranda |
| 5,160,731 | A | | 11/1992 | Sabatelli |
| 5,163,899 | A | | 11/1992 | Sibalis |
| 5,232,702 | A | | 8/1993 | Pfister |
| 5,234,690 | A | | 8/1993 | Chiang |
| 5,273,755 | A | | 12/1993 | Venktrama |
| 5,273,756 | A | | 12/1993 | Fallon |
| 5,308,625 | A | | 5/1994 | Wong |
| 5,356,632 | A | | 10/1994 | Gross |
| 5,358,715 | A | | 10/1994 | Wong |
| 5,372,579 | A | | 12/1994 | Sibalis |
| 5,421,816 | A | | 6/1995 | Lipkovker |
| 5,466,465 | A | | 11/1995 | Royds |
| 5,494,680 | A | | 2/1996 | Peterson |
| 5,505,958 | A | | 4/1996 | Bello |
| 5,554,381 | A | | 9/1996 | Roos |
| 5,560,922 | A | | 10/1996 | Chien |
| 5,571,528 | A | | 11/1996 | Lee |
| 5,585,111 | A | | 12/1996 | Peterson |
| 5,656,285 | A | | 8/1997 | Sablotsky |
| 5,667,798 | A | | 9/1997 | Royds |
| 5,698,217 | A | | 12/1997 | Wilking |
| 5,741,511 | A | | 4/1998 | Lee |
| 5,747,783 | A | | 5/1998 | Myung |
| 5,770,219 | A | | 6/1998 | Chiang |
| 5,814,599 | A | | 9/1998 | Mitragotri |
| 5,817,332 | A | | 10/1998 | Urtti |
| 5,833,647 | A | | 11/1998 | Edwards |
| 5,879,322 | A | | 3/1999 | Lattin |
| 5,906,830 | A | | 5/1999 | Farinas |
| 5,981,603 | A | * | 11/1999 | Hendler ........................ 514/712 |
| 6,248,341 | B1 | | 6/2001 | Anderson |
| 6,410,052 | B1 | | 6/2002 | Morre |

(Continued)

FOREIGN PATENT DOCUMENTS

| | | |
|---|---|---|
| CN | 1197786 | 11/1998 |
| CN | 1067675 | 6/2001 |

(Continued)

OTHER PUBLICATIONS

CAPLUS Accession No. 2005:988222 CAPLUS, Oct. 15, 2003 to Chen.*

Yanagi et al, Arch. Virol. 1989;108(1-2):151-9.*

Accession No. 142:37216 to Chen—2003.* http://www.google.com/patents/CN1448395A?cl=en, The web address for CN1448395 A, accessed on Jun. 16, 2014.*

Adhami, et al., "Molecular targets for green tea in prostate cancer prevention", J. Nutr., 133:2417S-2424S (2003).

Ahmad, et al., "Identification and characterization of murine caspase-14, a new member of the caspase family", Cancer Res., 58:5201-5205 (1998).

(Continued)

*Primary Examiner* — Jean Cornet
(74) *Attorney, Agent, or Firm* — Pabst Patent Group LLP

(57) ABSTRACT

Green tea polyphenol compositions and methods of their use in treating herpes simplex virus (HSV) are provided. Representative green tea polyphenols include, but are not limited to (−)-epigallocatechin-3-gallate as well as green tea polyphenols with one on more ester-linked fatty acids.

10 Claims, 11 Drawing Sheets

(56) References Cited

U.S. PATENT DOCUMENTS

| | | | | |
|---|---|---|---|---|
| 6,428,818 | B1 | 8/2002 | Morre | |
| 6,713,506 | B2 * | 3/2004 | Dou et al. | 514/450 |
| 7,358,383 | B2 | 4/2008 | Dou | |
| 2001/0051186 | A1 | 12/2001 | Acharya | |
| 2002/0176898 | A1 | 11/2002 | Morre | |
| 2004/0186167 | A1 | 9/2004 | Dou | |
| 2004/0191842 | A1 | 9/2004 | Hsu | |
| 2011/0003889 | A1 | 1/2011 | Kaihatsu | |

FOREIGN PATENT DOCUMENTS

| | | | |
|---|---|---|---|
| CN | 1448395 | | 4/2003 |
| CN | 1448395 | A * | 10/2003 |
| DE | 10156794 | | 6/2003 |
| JP | 9176010 | | 7/1997 |
| JP | 9227374 | | 9/1997 |
| TW | 200301141 | | 7/2003 |
| WO | 2004052873 | | 6/2004 |
| WO | 2010067869 | | 6/2010 |

OTHER PUBLICATIONS

Ahmed, et al., "Green tea polyphenol epigallocatechin-3-gallate (EGCG) differentially inhibits interleukin-1 beta-induced expression of matrix metalloproteinase-1 and -13 in human chondrocytes", J. Pharmacol, Exp. Ther., 308(2):767-73 (2004).

Alibardi, et al., "Ultrastructural localization of caspase-14 in human epidermis", J. Histochem. Cytochem., 52(12):1561-74 (2004).

Allen and Cullis, "Drug delivery systems: entering the mainstream", Science, 303(5665):1818-22 (2004).

Asgharnejad, "Improving Oral Drug Transport via Prodrugs", in Transport Processes in Pharmaceutical Systems, (Amidon, et al., ed.), pp. 185-218, Marcell Dekker: New York, NY (2000).

Balant, et al., "Prodrugs for the improvement of drug absorption via different routes of administration", Eur. J. Drug. Metab. Pharmacokinet., 15(2):143-53 (1990).

Balasubramanian, et al., "Green tea polyphenol stimulates a Ras, MEKK1, MEK3, and p38 cascade to increase activator protein 1 factor-dependent involucrin gene expression in normal human keratinocytes", J. Biol. Chem., 277:1828-1836 (2002).

Balimane and Sinko, "Involvement of multiple transporters in the oral absorption of nucleoside analogues", Adv. Drug Delivery Rev., 39(1-3):183-209 (1999).

Beck, et al., "A new long-acting injectable microcapsule system for the administration of progesterone", Fertil. Steril. 31:545-51 (1979).

Benita, et al., "Characterization of drug-loaded poly(d,l-lactide) microspheres", J. Pharm. Sci., 73:1721-4 (1984).

Bikle, et al., "Calcium- and vitamin D-regulated keratinocyte differentiation", Mol. Cell. Endocrinol., 177:161-171 (2001).

Bollag and Bollag, "1,25-Dihydroxyvitamin D(3), phospholipase D and protein kinase C in keratinocyte differentiation", Mol. Cell. Endocrinol., 177:173-182 (2001).

Borke, et al., "Monoclonal antibodies to human erythrocyte membrane Ca+—Mg++ adenosine triphosphatase pump recognize an epitope in the basolateral membrane of human kidney distal tubule cell", J. Clin. Invest., 80: 1225-1231 (1987).

Browne, "Fosphenytoin (Cerebyx)", Clin. Neuropharmacol., 20(1):1-12 (1997).

Bundgaard, "Bioreversible derivatization of drugs—principle and applicability to improve the therapeutic effects of drugs", Arch. Pharm. Chemi., 86(1):1-39 (1979). (with English abstract).

Cabrera, et al., "Beneficial effects of green tea—a review", J. Am. Coll. Nutr., 25(2):79-99 (2006).

Chen & Du, "Isolation and purification of a novel long-chain acyl catechin from lipophilic tea polyphenols", Chinese J. Chem., 21(7):979-981 (2003).

Chen, et al., "Degradation of green tea catechins in tea drinks", J. Agric. Food Chem., 49(1):477-82 (2001).

Chen, et al., "A novel long-chain acyl-derivative of epigallocatechin-3-O-gallate prepared and purified from green tea polyphenols", J Zhejiang Univ Sci., 6:714-8 (2003).

Chen, et al., "Preparation, structure, and antioxidant activity of EGCG palmitate", J. Zhejiang Univ., 30(4):422-425 (2003). (with English abstract).

Chen, et al., "Purification of long-chain fatty acid ester of epigallocatechin-3-O-gallate by high-speed counter-current chromatography", J. Chromatogr., 982:163-165 (2002).

Chen, et al., "The main active component of lipophilic tea polyphenols and in vitro inhibition activity on ovarian cancer cells HO-8910", J. Tea Sci., 23(2) 115-118 (2003). (with English abstract).

Chung, et al., "Dual mechanisms of green tea extract (EGCG)-induced cell survival in human epidermal keratinocytes", FASEB J., 17(13):1913-5 (2003).

Daikoku, et al., "Polyhenols including catechin from green tea with in vitro antiviral activity exhibited anti-herpes simplex virus activity but not anti-influenza virus activity in mice", J. Trad. Med., 28:63-72 (2011).

Dong, et al., "UVA light-induced DNA cleavage by isomeric methylbenz[a]anthracenes", Chem. Res. Toxicol., 15(3):400-7 (2002).

Eckhart, et al., "Caspase-14: analysis of gene structure and mRNA expression during keratinocyte differentiation", Biochem. Biophys. Res. Commun., 277:655-659 (2000).

Eckhart, et al., "Terminal differentiation of human keratinocytes and stratum corneum formation is associated with caspase-14 activation", J. Invest. Dermatol., 115:1148-51 (2000a).

Ege, "Reaction of Carboxylic Acids and Acid Derivatives with Alchohols as Neucleophiles. Acylation at Oxygen", in Organic Chemistry: Structure and Reactivity, 4th Ed., pp. 573, Houghton Mifflin Company: New York, NY (1999).

Farquhar, et al., "Biologically reversible phosphate-protective groups", J. Pharm. Sci., 72(3):324-325 (1983).

Fischer, et al., "Stratum corneum-derived caspase-14 is catalytically active", FEBS Lett., 577(3):446-50 (2004).

Fleisher, et al., "Design of prodrugs for improved gastrointestinal absorption by intestinal enzyme targeting", Methods Enzymol., 112:360-81 (1985).

Fleisher, et al., "Improved oral drug delivery: solubility limitations overcome by the use of prodrugs", Adv. Drug Delivery Rev., 19(2): 115-130 (1996).

Gaspano, "The role of PUVA in the treatment of psoriasis. Photobiology issues related to skin-cancer incidence", Am. J. Clin. Dermatol., 1:337-48 (2000).

Gillespie, et al., "Effects of oral consumption of the green tea polyphenol EGCG in a murine model for human Sjogren's syndrome, an autoimmune disease", Life Sci., 83(17-18):581-8 (2008).

Han and Amidon, "Targeted prodrug design to optimize drug delivery", AAPS Pharmsci., 2(1):E6 (2000).

He, et al., "Epigallocatechin gallate inhibits HBV DNA synthesis in a viral replication-inducible cell line", World J Gastroenterology, 17(11):1507-14 (2011).

Herbst, "Drug Latentiation", in Progress in Drug Research, (Jucker, ed.) 4:221-294, Birkhauser Verlag: Basel, Switzerland (1962).

Hiipakka, et al., "Structure-activity relationships for inhibition of human 5alpha-reductases by polyphenols", Biochem. Pharmacol., 63(6):1165-1176 (2002).

Hsu and Dickinson, "A new approach to managing oral manifestations of Sjogren's syndrome and skin manifestations of lupus", J. Biochem. Mol. Biol., 39(3):229-39 (2006).

Hsu, "Green tea and the skin", J. Am. Acad. Dermatol., 52(6):1049-59 (2005).

Hsu, et al, "Induction of p57 is required for cell survival when exposed to green tea polyphenols", Anticancer Research., 22:4115-4120 (2002b).

Hsu, et al., "A mechanism-based in vitro anticancer drug screening approach for phenolic phytochemicals", Assay Drug Dev. Technol., 1(5):611-8 (2003a).

Hsu, et al., "Chemoprevention of oral cancer by green tea", Gen. Dent., 50:140-6 (2002).

Hsu, et al., "Chemopreventive effects of green tea polyphenols correlate with reversible induction of p57 expression", Anticancer Research, 21:3743-3748 (2001).

(56) References Cited

OTHER PUBLICATIONS

Hsu, et al., "Green tea polypbenol-induced epithelial cell terminal differentiation is associated with coordinated expression of p57IKIP2 and caspase 14", J. Pharmacol. Exp. Ther., 312(3):884-90 (2005a).
Hsu, et al., "Green tea polyphenol targets the mitochondria in tumor cells inducing caspase 3-dependent apoptosis" , Anticancer Research, 23:1533-1540 (2003d).
Hsu, et al., "Inhibition of autoantigen expression by (−)-epigallocatechin-3-gallate (the major constituent of green tea) in normal human cells", J. Pharmacol. Exp. Ther., 315(2):805-11 (2005b).
Hsu, et al., "Green tea polyphenols induce differentiation and proliferation in epidermal keratinocytes", J. Pharmacol. Exp. Ther., 306:29-34 (2003).
Hsu, et al., "Green tea polyphenols reduce autoimmune symptoms in a murine model for human Sjogren's syndrome and protect human salivary acinar cells from TNF-alpha-induced cytotoxicity", Autoimmunity. 40(2):138-47 (2007).
Hsu, et al., "Green tea polyphenol induces caspase 14 in epidermal keratinocytes via MAPK pathways and reduces psoriasiform lesions in the flaky skin mouse model", Exp. Dermatol., 16(8):678-84 (2007b).
Hsu, et al., "Use of avidin-biotin-peroxidase complex (ABC) in immunoperoxidase techniques: a comparison between ABC and unlabeled antibody (PAP) procedures", J. Histochem. Cytochem., 29:577-580 (1981).
Hu, et al., "Caspase-14 is a novel developmentally regulated protease", J. Biol. Chem., 273:29648-29653 (1998).
Isaacs, et al., "Epigallocatechin gallate inactivates clinical isolates of herpes simplex virus", Antimicrob Agts and Chemother, 52(3):962-70 (2008).
Ivanova, et al., "Flavonoid compounds of larix sibirica and larix gmelinii bark", Khimiya Rastitel\nogo Syr\ya, 4:5-13 (2002) Abstract only.
Katiyar, et al., "Green teapolyphenols: DNA photodamage and photoimmunology", J. Photochem. Photobiol. B., 65(2-3):109-14 (2001).
Kazi, et al., "Potential molecular targets of tea polyphenols in human tumor cells: significance in cancer prevention", In Vivo, 16:397-403 (2002).
Kazi, et al., "Structure-activity relationships of synthetic analogs of (−)-epigallocatechin-3-gallate as proteasome inhibitors", Anticanc. Res., 24 (2B):943-954 (2004).
Kostovic and Pasic, "Phototherapy of psoriasis: review and update", Acta Dermatovenerol Croat., 12(1):42-50 (2004).
Lam, et al., "A potential prodrug for a green tea polyphenol proteasome inhibitor: evaluation of the peracetate ester of (−)-epigallocatechin gallate [(−)-EGCG].", Bioorg Med. Chem.,12:5587-93 (2004).
Lambert, "Rationale and applications of lipids as prodrug carriers", Eur. J. Pharm. Sci., 11 (Suppl 2):S15-27 (2000).
Landis-Piwowar, "A novel prodrug of green tea polyphenol (−)-epigallocatechin-3-gallate as a potential anticancer agent", Cancer Res., 67:4303-10 (2007).
Lazebnik, et al., "Nuclear events of apoptosis in vitro in cellfree mitotic extracts: a model system for analysis of the active phase of apoptosis", J. Cell Biol., 123(1):7-22 (1993).
Lippens, et al., "Caspase 14 is expressed in the epidermis, the choroid plexus, the retinal pigment epithelium and thymic Hassall's bodies", Cell Death Differ., 10:257-9 (2003).
Lippens, et al., "Epidermal differentiation does not involve the pro-apoptotic executioner caspases, but is associated with caspase-14 induction and processing", Cell Death Differ., 7:1218-1224 (2000).
Lippens, et al., "Vitamin D3 induces caspase-14 expression in psoriatic lesions and enhances caspase-14 processing in organotypic skin cultures", Am. J. Pathol.,165(3):833-41 (2004).
Madison, "Barrier function of the skin: "la raison d'etre" of the epidermis", J. Invest. Dermatol., 121:231-41 (2003).
Marston, et al., "Effect of a complex environmental mixture from coal tar containing polycyclic aromatic hydrocarbons (PAH) on the tumor initiation, PAH-DNA binding and metabolic activation of carcinogenic PAH in mouse epidermis", Carcinogenesis, 22(7):1077-86 (2001).
Martindale: The Complete Drug Reference, 32nd Ed., (Parfitt, ed.), pp. 367-389, Pharmaceutical Press: Chicago, IL (1999).
Mathiowitz, et al., "Morphology of Polyanhydride microsphere delivery systems", Scanning Microsc, 4:329-40 (1990).
Mathiowitz, et al., "Novel microcapsules for delivery systems", Reactive Polymers, 6:275-83 (1987).
Medina, et al., "Assessment of the phototoxic potential of compounds and finished topical products using a human reconstructed epidermis", In Vitr. Mol. Toxicol., 14(3):157-68 (2001).
Mizen and Burton, "The Use of Esters as Prodrugs for Oral Delivery of$^2$-Lactam antibiotics", Pharm. Biotech., 11:345-365 (1998).
Mori, et al., "Enhanced anti-influenza A virus activity of (−)-epigallocatechin-3-O-gallate fatty acid monoester derivatives: effect of alkyl chain length", Bioorg Med. Chem. Lett.,18(14):4249-52 (2008).
Morita, et al., "Cutaneous ultrastructural features of the flaky skin (fsn) mouse mutation", J. Dermatol., 22(6):385-95 (1995).
Mukhtar and Ahmad, "Tea polyphenols: prevention of cancer and optimizing health", Am. J. Clin. Nutr., 71(suppl):1698S-1702S (2000).
Nickoloff, et al., "Life and death signaling pathways contributing to skin cancer", J. Investig. Dermatol. Symp. Proc., 7(1):27-35 (2002).
Oliveira, et al., "Inhibition of herpes simplex virus type 1 with the modified green tea polyphenol palmitoyl-epigallocatechin gallate", Food Chem. Toxicol., 52:207-15 (2012).
Oya and Schulz, "Decreased expression of p57(KIP2) mRNA in human bladder cancer", Br. J. Cancer., 83(5):626-31 (2000).
Paterson and Anderson, "Chemistry, The renaissance of natural products as drug candidates", Science, 310:451-3 (2005).
Pauletti, et al., "Improvement of oral peptide bioavailability: Peptidomimetics and prodrug strategies", Adv. Drug Deliv. Rev., 27(2-3):235-256 (1997).
Ping, et al., "A novel catechin analog antioxidant for edible vegetable oils",Zhongguo Liangyou Zuebao, 18(5):77-79 (2003) Abstract only.
Pistritto, et al., "Expression and transcriptional regulation of caspase-14 in simple and complex epithelia", Cell Death. Differ., 9:995-1006 (2002).
Rendl, et al., "Caspase-14 expression by epidermal keratinocytes is regulated by retinoids in a differentiation-associated manner", J. Invest. Dermatol., 119:1150-1155 (2002).
Rojas, et al., "Myeloperoxidase—463A variant reduces benzo[a]pyrene diol epoxide DNA adducts in skin of coal tar treated patients", Carcinogenesis, 22(7)1015-1018 (2001).
Rozen and Skaletsky, "Primer3 on the WWW for general users and for biologist programmers", Methods Mol. Biol., 132:365-86 (2000).
Rubin, "Synergistic mechanisms in carcinogenesis by polycyclic aromatic hydrocarbons and by tobacco smoke: a bio-historical perspective with updates", Carcinogenesis, 22(12):1903-30 (2001).
Sadzuka, "Effective prodrug liposome and conversion to active metabolite", Curr. Drug Metab., 1(1):31-48 (2000).
Sano, et al., "Stat3 links activated keratinocytes and immunocytes required for development of psoriasis in a novel transgenic mouse model", Nat. Med., 11(1):43-9 (2005).
Schon, et al., "Pathogenic function of IL-1 beta in psoriasiform skin lesions of flaky skin (fsn/fsn) mice", Clin. Exp. Immunol., 123(3):505-10 (2001).
Sharangi, "Medicinal and therapeutic potentialities of tea (*Camellia sinensis* L.)—A review", Food Res Intl, 42(5-6):529-35 (2009).
Singh, et al., "Epigallocatechin-3-gallate selectively inhibits interleukin-1 beta-induced activation of mitogen activated protein kinase subgroup cJun N-terminal kinase in human osteoarthritis chondrocytes", J. Orthop. Res., 21(1):102-9 (2003).
Song, et al., "Antiviral effect of catechins in green tea on influenza virus", Antivirus Response, 68:66-74 (2005).
Stratton, et al., "The state-of-the-art in chemoprevention of skin cancer", Eur. J. Cancer, 36:1292-7 (2000).
Sundberg, et al., Full-thickness skin grafts from flaky skin mice to nude mice: maintenance of the psoriasiform phenotype\, J. Invest. Dermatol., 102(5):781-8 (1994).

(56) References Cited

OTHER PUBLICATIONS

Szoka, et al., "Comparative properties and methods of preparation of lipid vesicles (liposomes).", Ann. Rev. Biophys. Bioeng., 9: 467-508 (1980).
Tedeschi, et al., "Green tea inhibits human inducible nitric-oxide synthase expression by down-regulating signal transducer and activator of transcriptionlalpha activation", Mol. Pharmacol., 65(1):111-20 (2004).
Thein, et al., "A strong genotoxic effect in mouse skin of a single painting of coal tar in hairless mice and in MutaMouse", Mute Res., 468(2):117-124 (2000).
Uesato, et al., "Inhibitory effects of 3-O-acyl-(+)-catechins on Epstein-Barr virus activation", Chem Pharm Bull (Tokyo), 51:1448-50 (2003).
Van De Craen, et al., "Identification of a new caspase homologue: caspase-14", Cell. Death Differ., 5:838-846 (1998).
Vayalil, et al., "Treatment of green tea polyphenols in hydrophilic cream prevents UVB-induced oxidation of lipids and proteins, depletion of antioxidant enzymes and phosphorylation of MAPK proteins in SKH-1 hairless mouse skin", Carcinogenesis, 24:927-36 (2003).
Vogel, et al., "Pharmacological coal tar induces G:C to T:A transversion mutations in the skin of MutaMouse", Pharmacol Toxicol., 89(1):30-34 (2001).
Walsh, et al., "Psoriasis is characterized by altered epidermal expression of caspase-14, a novel regulator of keratinocyte terminal differentiation and barrier formation", J. Dermat. Sci., 37(1):61-3 (2005).
Wan, et al., "Structure-activity study of epi-gallocatechin gallate (EGCG) analogs as proteasome inhibitors", Bioorg. Med. Chem., 13:2177-2185 (2005).
Wan, et al., "Study of the green tea polyphenols catechin-3-gallate (CG) and epicatechin-3-gallate (ECG) as proteasome inhibitors", Bioorg. Med. Chem., 12(13):3521-7 (2004).
Wang, et al., "Prodrug approaches to the improved delivery of peptide drugs", Curr. Pharm. Design., 5(4):265-287 (1999).
Wermuth, et al., "Designing Prodrugs and Bioprecursors I. Carrier Prodrugs", Pract. Med. Chem., 671-696 (1996).
Willard, "Rapid directional translocations in virus replication", J Virol., 10:5220-32 (2002).
Williamson, et al., "Epigallocatechin gallate, the main polyphenol in green tea, binds to the T-cell receptor, CD4: Potential for HIV-1 therapy", J. Allergy Clin Immunol 118:1369-74 (2006).
Wood and Earnshaw, "Mitotic chromatin condensation in vitro using somatic cell extracts and nuclei with variable levels of endogenous topoisomerase II", J. Cell Biol., 111 (6 Pt 2):2839-50 (1990).
Xia, et al., "Transgenic delivery of VEGF to mouse skin leads to an inflammatory condition resembling human psoriasis", Blood, 102(1):161-8 (2003).
Yamamoto, et al., "Green tea polyphenol causes differential oxidative environments in normal vs. malignant cells", J. Pharmacol. Exp. Ther., 307(1):230-6 (2003).
Yamamoto, et al., "EGCG-targeted p57/KIP2 reduces tumorigenicity of oral carcinoma cells: role of c-Jun N-terminal kinase", Toxicol. Appl. Pharmacol., 224(3):318-25 (2006).
Yang, et al, "Inhibition of carcinogenesis by tea", Annu. Rev. Pharmacol. Toxicol., 42:25-54 (2002).
Yoneda, et al., "p53 gene mutations and p21 protein expression induced independently of p53, by TGF-beta and gamma-rays in squamous cell carcinoma cells", Eur. J. Cancer, 35:278-83 (1999).
Yoshimo, et al., "Inhibitory effects of the C-2 epimeric isomers of tea catechins on mouse type IV allergy", J AgricFood Chem., 52:4660-3 (2004).
Yu, et al., "Prodrugs of fluoro-substituted brnzoates of EGC as tumor cellular proteasome inhibitors and apoptosis inducers", Intl. J Mol Sci., 9(6):951-61 (2008).
Zenz, et al., "Psoriasis-like skin disease and arthritis caused by inducible epidermal deletion of Jun proteins", Nature, 437(7057):369-75 (2005).
Zhao, et al., "Apoptosis of mouse liver nuclei induced in the cytosol of carrot cells", FEBS Lett., 448(1):197-200 (1999).
Zollner, et al., "Animal models of T-cell-mediated skin diseases", Bioessays, 26(6):693-6 (2004).
Azuma et al. "Immortalization of normal human salivary gland cells with duct-, myoepithelial-, acinar-, or squamous phenotype by transfection with SV40 ori-mutant deoxyribonucleic acid," Lab Invest. 69(I):24-42(1993).
Banker, et al., "Modern Pharmaceutics, 3rd ed", Marcel Dekker, New York, 451 and 596 (1995).
Baudouin, et al. "Current treatments of xerophthalmia in Sjögren's syndrome," Rev Med Interne. 25(5):376-82(2004).
Billings, et al. "Xerostomia and associated factors in a community-dwelling adult population," Community Dent Oral Epidemiol. (5):3 12-6(1996).
Bolstad et al. "Increased salivary gland tissue expression of Fas, Fas ligand, cytotoxic T lymphocyte-associated antigen 4, and programmed cell death 1 in primary Sjögren's syndrome," Arthritis Rheum 48:174-85(2003).
Borchardt, et al. "improvement in peptide bioavailability: Peptidomimetics and Prodrug Strategies", Adv. Drug. Delivery Rev. 27:235-256(1997).
Callen, "Update on the management of cutaneous lupus erythematosus," Br. J. Dematol. 151(4):731-6) (2004).
Carsons, "A review and update of Sjögren's syndrome: manifestations, diagnosis, and treatment," Am J Manag Care. 7(14 Suppl):S433-43.24(2001).
Cassolato, et al. "Xerostomia: clinical aspects and treatment." Gerodontology. 20(2):64-77(2003).
Cha, et al. "Progress in understanding autoimmune exocrinopathy using the non-obese diabetic mouse: an update," Crit. Rev. Oral Biol. Med. 13:4-16(2002).
Chen, et al., "A novel catechin analog antioxidant for edible vegetable oils", Zhongguo Liangyou Zuebae, 18(5):77-9 (2003e) Abstract Only.
Daniels and Fox, "Salivary and oral components of Sjögren's syndrome," Rheum. Dis. Clin. North Am. 18(3):571-89(1992).
Daniels and Wu, "Xerostomia—clinical evaluation and treatment in general practice," Calif Dent Assoc. 28(12):933-41(2000).
Fox, "Sjogren's syndrome: evolving therapies," Expert Opin Investig Drugs. 12(2):247-54(2003).
Fox, "Sjögren's syndrome. Controversies and progress," Clin Lab Med. 17(3):431-44(1997).
Ikebe, et al. "Perception of dry mouth in a sample of community-dwelling older adults in Japan," Spec Care Dentist. 21(2):52-9(2001).
Khurshudian, "A pilot study to test the efficacy of oral administration of interferon-alpha lozenges to patients with Sjögren's syndrome," Oral Surg Oral Med Oral Pathol Oral Radiol Endod. 95(1):38-44(2003).
Medical College of Georgia (Apr. 25, 2003). "Green Tea Linked to Skin Cell Rejuvenation." ScienceDaily. Retrieved Feb. 5, 2008, from http://www.sciencedaily.com¬ /releases/2003/04/030425071800.htm.
Miyasaka, "Epidemiology and pathogenesis of Sjögren's syndrome," Nippon Rinsho 53(10):2367-70 (1995).
Oral Cancer News, (Oct. 8, 2004): "Green tea research lead to gum and other products", http://oralcancernews.org/wp/green-tea-research-leads-to -gum-and-other-products-2/.Downloaded Dec. 17, 2012.
Porter, et al. "An update of the etiology and management of xerostomia," Oral Surg Oral Med Oral Pathol Oral Radiol Endod. 97(I):28-46(2004).
Rehman,"Sjögren's syndrome,"Yonsei Med J. 44(6):947-54) (2003).
Schein, et al. "Dry eye and dry mouth in the elderly: a population-based assessment" Arch Intern Med. 159(12): 1359-63(1999).
Stinton, et al. "Autoantibodies to protein transport and messenger RNA processing pathways: endosomes, lysosomes, Golgi complex, proteasomes, assemblyosomes, exosomes, and GW bodies," Clin Immunol. 110(I):30-44(2004).
Uchida, et al., "Identification of specific autoantigens in sjögren\s syndrome by serex", Immunology, 116:53-63 (2005).

(56) References Cited

OTHER PUBLICATIONS

Vitali, et al, "Classification criteria for Sjögren's syndrome: a revised version of the European criteria proposed by the American-European Consensus Group," Ann Rheum Dis. 61(6):554-8(2002).
Vivino, et al., "Pilocarpine tablets for the treatment of dry mouth and dry eye symptoms in patients with Sjögren syndrome: a randomized, placebo-controlled, fixed-dose, multicenter trail", Arch Intern Med., 159:174-81 (1999).
Wolff, "Burger\s Medicinal Chemistry, 5th ed, Part 1" John Wiley & Sons, 975-977 (1995).
Yoshida, "Sjögren's syndrome," Nippon Rinsho 57(2):360-3(1999).
Zhang, "Epidemiological study of primary Sjogrne's syndrome in China," Chin Med J (Engl). 108(10):787-8(1995).
Zhao, et al., "A proprietary topical preparation containing EGCG-stearate and glycerin with inhibitory effects on herpes simplex virus: case study", Inflam. Allergy Drug Targets, 11(5):1-5 (2012).

* cited by examiner

COMPOSITIONS AND METHODS FOR TREATING HERPES SIMPLEX VIRUS

CROSS REFERENCE TO RELATED APPLICATIONS

This application claims benefit of U.S. Provisional Application No. 61/361,752, filed Jul. 6, 2010, and is a continuation-in-part of U.S. patent application Ser. No. 12/063,139, filed on Feb. 7, 2008, which is a national phase of PCT/US2006/031120 filed on Aug. 6, 2006, which claims priority to U.S. Provisional Patent Application No. 60/707,234 filed on Aug. 11, 2005, all of which are hereby incorporated herein by reference in there entireties where permissible.

REFERENCE TO SEQUENCE LISTING

The Sequence Listing submitted herewith as a text file named "MCG_2009_017_Sequence_Listing_Text_File.txt," created on Jun. 23, 2011, and having a size of 14,471 bytes is hereby incorporated by reference pursuant to 37 C.F.R. §1.52 (e)(5).

FIELD OF THE INVENTION

The invention is generally related to compositions and methods for treating virus infections, more particularly to green tea polyphenol compositions and methods of their use in the treatment or prophylaxis of herpes simplex virus.

BACKGROUND OF THE INVENTION

The herpes simplex virus (HSV) is a virus that manifests itself in two common viral infections, each marked by painful, watery blisters in the skin or mucous membranes (such as the mouth or lips) or on the genitals. The disease is contagious, and there is currently no cure or vaccine for HSV. An infection on the lips is commonly known as a "cold sore" or "fever blister." When asymptomatic, HSV lies dormant in the bodies of the nerve cells, replicating within the axons towards the skin during an outbreak. When the outbreak has passed, the virus "dies back" along the nerve until it is only present in the nerve body. The dormancy of the virus within the nerve bodies contributes to the difficulty of treatment.

Currently available treatments include orally-administered antiviral medications such as acyclovir, famciclovir, pancyclovir, valacyclovir, or the like, which reduce the duration of symptoms and accelerates healing. Treatment typically begins at the first symptoms of an outbreak. Another option is the use of daily suppressive therapy, in which antivirals are taken every day over the course of years. Suppressive therapy may reduce frequency of symptoms and recurrence of outbreaks. In addition, suppressive therapy reduces subclinical shedding, lowering the risk of transmission through sexual contact or kissing.

Nonprescription treatments for cold sores are typically effective for short periods of time an often include toxic ingredients.

A substantial problem with taking any antiviral medication can be side effects such as confusion, hallucinations, increased thirst, redness, blistering, peeling or loosening of the skin, including inside the mouth, reduced amount of urine passed, seizures, skin rash or hives, stomach pain, tremor, unusual weakness or tiredness, diarrhea, dizziness, headache, increased sensitivity to the sun, loss of appetite, nausea, or vomiting.

It is therefore an object of the invention to provide improved compositions and methods for treating one or more symptoms of a viral infection with reduced side effects in a subject.

It is still another object of the invention to provide methods and compositions for treating HSV infection in a subject.

SUMMARY OF THE INVENTION

Compositions and methods for treating viral infections, in particular herpes simplex virus (HSV) are provided. One embodiment provides therapeutic compositions for treating lesions caused by HSV. Useful compositions include compositions containing one or more green tea polyphenols (GTPs) or derivatives thereof. The compositions inhibit the formation of a lesion resulting from HSV when administered in the prodormal stage and greatly reduces the duration of a lesion resulting from infection with HSV when administered after the lesion has appeared relative to a control. Exemplary methods include inhibiting HSV replication in a cell by contacting the cell with a composition containing one or more GTPs or derivatives thereof. Another method includes treating one or more symptoms of HSV in a subject by topically administering to the subject a composition containing one or more GTPs or derivatives thereof.

Representative green tea polyphenols include, but are not limited to (−)-epigallocatechin-3-gallate, (−)-epicatechin, (−)-epigallocatechin, and (−)-epicatechin-3-gallate. Also included are proanthocyanidins, enantiomers, isomers, pharmaceutically acceptable salts, and prodrugs of these GTPs. Preferred GTPs are modified to contain one or more hydrocarbon chains having $C_1$ to $C_{30}$ groups.

DETAILED DESCRIPTION OF THE INVENTION

I. Definitions

Figure 1:
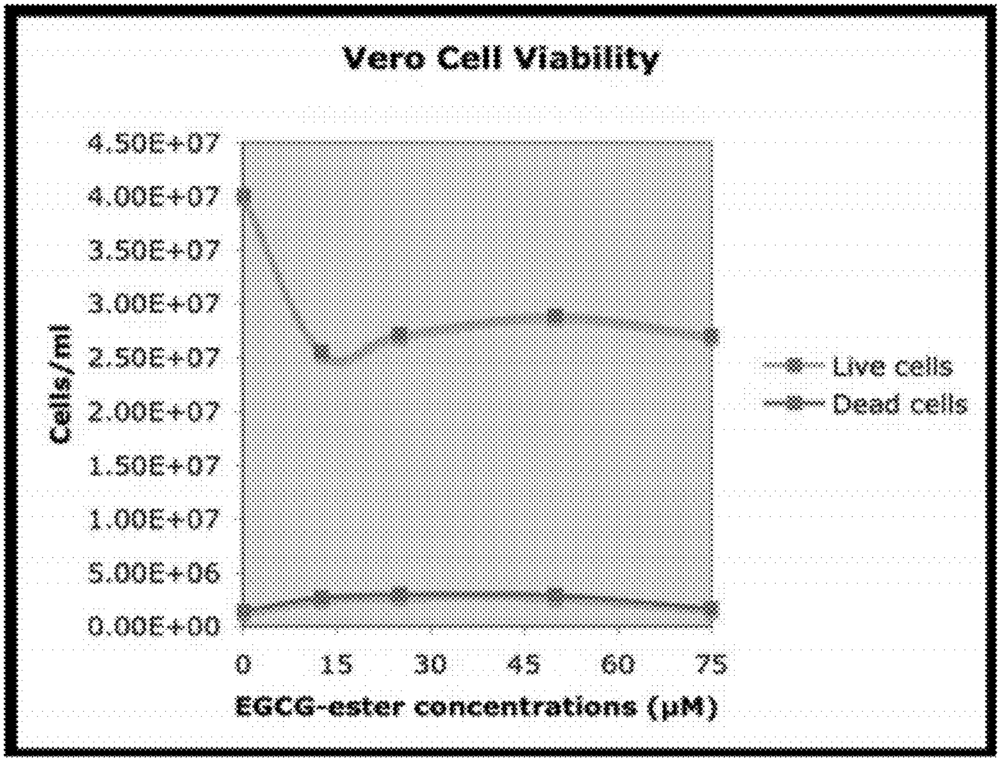
FIG. 1 is a line graph of Vero cells/ml versus EGCG-ester concentrations (μM). The upper trace represents live cells and the lower trace represents dead cells.

Before explaining the various embodiments of the disclosure, it is to be understood that the invention is not limited in its application to the details of construction and the arrangement of the components set forth in the following description. Other embodiments can be practiced or carried out in various ways. Also, it is to be understood that the phraseology and terminology employed herein is for the purpose of description and should not be regarded as limiting.

Throughout this disclosure, various publications, patents and published patent specifications are referenced. Where permissible, the disclosures of these publications, patents and published patent specifications are hereby incorporated by reference in their entirety into the present disclosure to more fully describe the state of the art.

To facilitate understanding of the disclosure, the following definitions are provided:

As used herein, the singular forms "a," "an," and "the" include plural referents unless the context clearly dictates otherwise. Thus, for example, reference to "a factor" refers to one or mixtures of factors, and reference to "the method of treatment" includes reference to equivalent steps and methods known to those skilled in the art, and so forth.

"Acyloxy", as used herein, refers to a substituent having the following chemical formula:

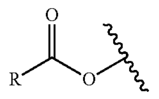

wherein R is a linear, branched, or cyclic alkyl, alkenyl, or alkynyl group.

"Alkoxy carbonyl", as used herein, refers to a substituent having the following chemical formula:

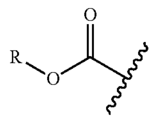

wherein R is a linear, branched, or cyclic alkyl group.

The term "alkenyl" refers to a monovalent, unbranched or branched hydrocarbon chain having one or more double bonds therein. The double bond of an alkenyl group can be unconjugated or conjugated to another unsaturated group.

The term "alkynyl" refers to a monovalent, unbranched or branched hydrocarbon chain having one or more triple bonds therein. The triple bond of an alkynyl group can be unconjugated or conjugated to another unsaturated group.

The term "cell" refers to a membrane-bound biological unit capable of replication or division.

The term "emulsion" refers to a mixture prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions. In oil-in-water emulsions the lipophilic phase is dispersed in the aqueous phase, while in water-in-oil emulsions the aqueous phase is dispersed in the lipophilic phase. Commonly known emulsion based formulations that are applied to the skin include cosmetic products such as creams, lotions, washes, cleansers, milks and the like as well as dermatological products comprising ingredients to treat skin conditions, diseases or abnormalities.

The term "Green Tea Polyphenols or GTP" refers to polyphenolic compounds present in the leaves of *Camellia sinensis*. Green tea polyphenols include, but are not limited to (−)-epicatechin (EC), (−)-epigallocatechin (EGC), (−)-epicatechin-3-gallate (ECG), (−)-epigallocatechin-3-gallate (EGCG), proanthocyanidins, enantiomers thereof, epimers thereof, isomers thereof, combinations thereof, and prodrugs thereof. Modified green tea polyphenols refers to a green tea polyphenol having one or more hydrocarbon chains, for example $C_1$ to $C_{30}$ and the compounds according to Formula I and II disclosed herein.

The term "host" refers to a living organism, including but not limited to a mammal such as a primate, and in particular a human.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

The term "isolated," when used to describe the various compositions disclosed herein, means a substance that has been identified and separated and/or recovered from a component of its natural environment. For example an isolated polypeptide or polynucleotide is free of association with at least one component with which it is naturally associated. Contaminant components of its natural environment are materials that would typically interfere with diagnostic or therapeutic uses for the polypeptide or polynucleotide and may include enzymes, and other proteinaceous or non-proteinaceous solutes. An isolated substance includes the substance in situ within recombinant cells. Ordinarily, however, an isolated substance will be prepared by at least one purification step.

"Lipid soluble" as used herein refers to substances that have a solubility of greater than or equal to 5 g/100 ml in a hydrophobic liquid such as castor oil.

The term "lipid-soluble green tea polyphenol" refers to a green tea polyphenol having one or more hydrocarbon chains having for example $C_1$ to $C_{30}$ groups linked to the polyphenol. $C_1$ to $C_{30}$ groups include for example cholesterol. Representative lipid-soluble green tea polyphenols include those according to Formula I and Formula II disclosed herein. The term is used interchangeably with "modified green tea polyphenol".

The term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

The term "pharmaceutically acceptable carrier" refers to a carrier or diluent that does not cause significant irritation to an organism and does not abrogate the biological activity and properties of the administered compound.

The term "pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the green tea polyphenols described herein, or a pharmaceutically acceptable salts thereof, with other chemical components, such as physiologically acceptable carriers and excipients. The purpose of a pharmaceutical composition is to facilitate administration of a compound to an organism.

The term "prodrug" refers to an agent, including nucleic acids and proteins, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "substituted $C_1$ to $C_{30}$" refers to an alkyl, alkenyl, or alkynyl chain of one to thirty carbons wherein one or more carbons are independently substituted with one or more groups including, but not limited to, halogen, hydroxy group, aryl group, heterocyclic group, or alkyl ester. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{28}$, etc. The range also includes less than $C_{30}$, less than $C_{19}$, etc.

The term "treating or treatment" refers to alleviating, reducing, or inhibiting one or more symptoms or physiological aspects of a disease, disorder, syndrome, or condition.

"Water soluble" as used herein refers to substances that have a solubility of greater than or equal to 5 g/100 ml water.

The term "treating or treatment" refers to alleviating, reducing, or inhibiting one or more symptoms or physiological aspects of a disease, disorder, syndrome, or condition.

It will be appreciated that a numerical range provided herein includes each intervening integer II. Herpes Simplex Virus Herpes simplex virus (HSV) types 1 and 2 belong to the family Herpesviridae, subfamily Alphaherpesviridae, and the genus *Simplexvirus*.

A. HSV Structure

HSV viruses measure approximately 200 nm in diameter. HSV 1 and 2 are enveloped, double stranded DNA viruses of about 152 Kb in length, containing two segments of DNA, known as unique long (Ul) and unique short (Us) regions. (Garner, Advanced Drug Delivery Reviews. 2003; 55:1497-1513). The virion has 3 major structures; an outer portion called the envelope, which includes 11 glycoproteins (gB gC, gD, gE, gG, gH, gI, gJ, gK, gL, gM), a tegument layer composed of 15 proteins, and an icosahedral capsid enclosing the viral DNA as well as 4 structural proteins. (Foster, et al., Journal of Virological Methods. 1998; 75:151-160; Garner, Advanced Drug Delivery Reviews. 2003; 55:1497-1513; Willard, Journal of Virology. 2002; 10:5220-5232).

B. HSV Life Cycle

As soon as a person is exposed to HSV, a critical series of events within cellular, molecular and immune system biology takes place. Several glycoproteins located on the virus envelope are responsible for cell recognition, cell fusion, and eventually cell entry (Spear, et al., Journal of Virology. 2005; 344:17-24; Subramanian, et al., PNAS. 2006; 104 (8):2903-2908). The first contact of HSV with its host cell is by binding to heparin sulfate chains contained on the cell surface proteoglycans. The viral glycoproteins B and C assist this binding reaction as glycoprotein D is recruited to bind to one the host cell receptors. Once glycoprotein D binds to the cell receptor, glycoproteins B, H and L form a fusion complex along with glycoprotein D and the cell receptor. This fusion complex is what allows the virion's plasma membrane to fuse to the host cell plasma membrane and subsequently viral nucleocapsid and tegument entry. Consequently, although glycoprotein D is essential for cell recognition and receptor binding, all five glycoproteins are needed for successful virus adsorption and fusion (Carfi, et al. Molecular Cell. 2001; 8:169-179; Spear, et al., Journal of Virology. 2005; 344:17-24).

When a short lysine-rich region (KPKKNKKPK (SEQ ID NO:1)) within glycoprotein B of HSV-1 was removed in an experiment with Vero cells, heparin sulfate could not be bound by the receptors. Although glycoproteins B and C are not required during the first binding at heparan sulfate chains, they do make the process more efficient. Thus, not only gD, but also this lysine-rich region within gB seems to be indispensable for competent viral entry into the host cell (Carfi, et al. Molecular Cell. 2001; 8:169-179; Spear, et al., Journal of Virology. 2005; 344:17-24).

Glycoprotein D recognizes and can bind to one of several host receptors. These include, HVEM (Herpesvirus entry mediator), a member of the TNF-receptor family; nectin-1 or nectin-2, members of the immunoglobulin superfamily; and locations on the cell surface made by the reaction of heparin sulfate and 3-O-sulfotransferases (Shukla, et al., Journal of Clinical Investigations. 2001; 108:503-510; Spear et al., Journal of Virology. 2005; 344:17-24). The structure of HSV-1 glycoprotein D has been obtained by x-ray crystallography, and several amino acid residues within gD were seen to be critical for the binding of the receptors HVEM and nectin-1 (Carfi, et al., Molecular Cell. 2001; 8:169-179; Manoj et al., PNAS. 2004; 101(34): 12414-12421; Whitebeck, et al., Journal of Virology. 1997; 71(8):6083-6093). HSV-1 and HSV-2 glycoprotein D have been shown to contain 82% amino acid similarity.

Once inside the cell, HSV takes over the cellular transport machinery in order to have access to the internal cellular compartments. Viral particles move throughout different regions of the cytoplasm in an extremely fast manner allowing viral components to reach their destinations in a very efficient way (Willard, M., Journal of Virology. 2002; 10:5220-5232). The viral particles are sent to the nucleus through the nucleopores where the viral genome will enter and viral transcription and replication will begin. HSV uses microtubules to travel by retrograde transport to the nucleus with the help of the dynein motor system (Bearer, et al., Proceedings of the National Academy of Science. 2000; 97(14): 8146-8150. Garner, Advanced Drug Delivery Reviews. 2003; 55:1497-1513. Stanberry, University Press of Mississipi. 2nd Ed. 2006.). Being able to enter the nucleus is essential for viral transcription, translation, replication, and packaging of the DNA into progeny nucleocapsids. Interestingly, in flat cells such as Vero cells, the process of transporting viral particles through the usage of microtubules may not be necessary in order to achieve a successful infection. Vero cells can make use of diffusion to transport the virion to the nucleus (Newcomb, et al., Journal of Molecular Biology. 2007; 370:633-642.).

HSV-1 and HSV-2 infect epithelial cells during lytic infection and move to sensory neurons in latent infections. During the latent infection, viruses stay in a dormant state within nerve cells until they are triggered into the lytic cycle (Kang, et al., Virology. 2003; 312: 233-244; Stanberry, University Press of Mississipi. 2nd Ed. 2006.). This allows HSV to permanently survive and replicate for the lifetime of the HSV infected patient (Kang, et al., Virology. 2003; 312: 233-244; Wysocka, et al., Trends in Biochemical Sciences. 2003; 28(6):294-304.). For the virus to become latent, viral particles have to travel from nerve axons at the initial site of infection to the sensory ganglia$_3$. The latently infected nerve cells do not replicate HSV's DNA, but they make mRNA of a short sequence of the genome known as the latency associated transcript (LAT). A study done in which this sequence was removed showed that viruses were not able to cause recurrent infections. (Kang, et al., Virology. 2003; 312: 233-244.)

These latently infected cells may be unreactive for a long period of time, but can reactivate at anytime during one's life course. There are several factors that can be associated with virus reactivation, such as stress, heat, cold, ultraviolet light, emotional responses, and pituitary or adrenal hormones. When the virus is reactivated, the viral genome travels by anterograde transport in axons, to the epithelium where, viral replication will occur (Fatahzadeh, et al. American Academy of Dermatology. 2007; 6(27):737-763; Spear, et al., Journal of Virology. 2005; 344:17-24).

Although the only known natural host for HSV infection is humans, cultured cells from a variety of different animals, such as Vero cells from green monkey kidney cells, can also be infected by HSV in the laboratory (Foster, et al., Journal of Virological Methods. 1998; 75:151-160). In vitro experiments with HSV virions do not involve the immune system of an animal, allowing the virus to infect cells efficiently. Thus, several cells contain at least one of the receptors necessary for viral entry by the envelope glycoprotein gD of HSV (Spear, et al., Journal of Virology. 2005; 344:17-24.).

There are five stages of a cold sore, from initial manifestation to complete healing. The first sign is the prodromal stage which consists of tingling, itching, inflammation, erythema, hypersensitivity, and/or soreness in the exact location where the lesion will erupt. The prodrome usually lasts for one to two days and ends when blisters appear, signaling the onset of the blister stage. The blisters are filled with clear, yellow fluid. Several separate blisters may appear to coalesce as more blisters appear in the intervening spaces. After approximately two days, the blisters begin to rupture, exposing an erythematous open wound that becomes gray in color. This is the weeping stage. Highly infective yellowish fluid oozes from the wounds for a day or so. The wounds are covered with yellowish crusts in the scabbing stage, which lasts for two to three days. The skin beneath the scabs continues to be painful and pruritic, and the scabs begin to break and bleed. As this stage slowly resolves, the patient enters the healing stage. Secondary scabs become progressively smaller and slowly slough to reveal pink skin that gradually assumes the appearance of the surrounding unaffected epidermis. The usual duration of the condition is seven to 10 days, but it may persist as long as two weeks.

C. Treatment of HSV

Most over-the-counter topical treatments for cold sores are topical anesthetics to decrease pain, skin protectants (petroleum or zinc oxide), or antiseptics. Most of these topical treatments attempt to reduce the pain, discomfort and appearance of the cold sore but usually have little effect on the duration of the lesion. In addition, antiviral medications have been developed in an attempt to reduce the occurrence of lesion outbreaks and attempt to subvert the viral activity in the body. Many of these antiviral medications are administered orally. Antiviral medications have also been developed as topical treatments in an attempt to slow down the activity of the virus within the lesion and are usually most effective if administered prior to the formation of the vesicles.

Current antiviral drugs of preference for the treatment of oral or genital HSV infections are acyclovir (Zovirax, Glaxo SmithKline, Research Triangle Park, N.C.), valacyclovir (Valtrex, Glaxo SmithKline, Research Triangle Park, N.C.), penciclovir (Denavir, Novaris Pharma GmbH, Wehr, Germany), and famiciclovir (Famvir, Novartis Pharmaceuticals Corporation, East Hanover, N.J.). These drugs are often given orally for 7 to 10 days. Both valacyclovir and famciclovir break down in the body into active forms of the medicine (acyclovir and penciclovir). By being analogs of nucleosides, these drugs are able to shut off viral replication (Brady, et al. Antiviral Research. 2003; 61: 73-81; Fatahzadeh, et al. American Academy of Dermatology. 2007; 6(27):737-763; Morfin, et al, Journal of Clinical Virology. 2002; 26: 29-37).

The HSV thymine kinase phosphorylates acyclovir, and the host cell further phosphorylates it resulting in an active acyclovir triphosphate. Active acyclovir can then inhibit viral DNA polymerase, preventing viral DNA elongation. One problem with using these drugs is that the drugs are efficient only until HSV begins to alter its thymine kinase and becomes resistant to acyclovir and the other drugs that work as analogs of nucleosides (Froben, et al., Antiviral Research. 2008; 7928-7936; Lebel, et al., Journal of Clinical Virology. 2006; 37:34-37).

The mode of action of famiciclovir is also by inhibiting viral DNA polymerase in a process similar to acyclovir, although with less efficacy. Famiciclovir is able to obtain higher concentrations within cells and has a longer-half life compared to acyclovir. It can also be given less frequently than acyclovir. Lastly, Cidofovir, an acyclic nucleoside 5'-monophosphate, is phosphorylated by the host cell kinases and is able to inhibit the viral DNA polymerase in this manner. HSV resistance to cidofovir may also arise when the DNA polymerase gene is mutated (Brady, et al. Antiviral Research. 2003; 61: 73-81; Stanberry, University Press of Mississipi. 2nd Ed. 2006). Because of the great resistance that arises from taking these different drugs, new and more effective medications need to be developed in order to prevent the shedding of HSV (Morfin, et al, Journal of Clinical Virology. 2002; 26: 29-37).

III. Green Tea Polyphenols

One embodiment provides a composition having one or more green tea polyphenols, preferably one or more green tea polyphenols modified with one or more hydrocarbon chains having $C_1$ to $C_{30}$ groups, or a combination thereof. Representative green tea polyphenols include, but are not limited to (−)-epigallocatechin-3-gallate, (−)-epicatechin, (−)-epigallocatechin, and (−)-epicatechin-3-gallate. Preferred modified GTPs include modified (−)-epigallocatechin-3-gallate, a pharmaceutically acceptable salt, prodrug, or derivative thereof, in an amount effective to treat herpes simplex virus (HSV) infection compared to a control. Experimental controls or control groups are known in the art. Generally, the effect of the green tea polyphenol composition on the inhibition of HSV replication can be compared to the effect of the composition without the green tea polyphenol on the inhibition of HSV. Representative hosts include mammals such as humans or cells from mammals such as humans.

A modified GTP, a derivative or a variant of a green tea polyphenol includes green tea polyphenols having chemical modifications to increase solubility or bioavailability in a host. In certain embodiments, these chemical modifications include the addition of chemical groups having a charge under physiological conditions. In other embodiments the modifications include the conjugation of the green tea polyphenol to other biological moieties such as polypeptides, carbohydrates, lipids, or a combination thereof. Preferred modifications include modifications with one or more hydrocarbon chains having $C_1$ to $C_{30}$ groups.

Another embodiment provides a pharmaceutical composition including one or more green tea polyphenols, modified green tea polyphenols, optionally in combination with a pharmaceutically acceptable carrier, diluent, or excipient. The one or more green tea polyphenols and/or modified green tea polyphenols are in an amount effective to treat one or more symptoms of viral infection for example the inhibition of HSV replication in a host. Preferred compositions contain an antiviral amount of a modified green tea polyphenol. In other embodiments, the active ingredient in the composition consists essentially of (−)-epigallocatechin-3-gallate, (−)-epigallocatechin-3-gallate modified with one or more hydrocarbon chains having $C_1$ to $C_{30}$ groups, or a combination thereof, a pharmaceutically acceptable salt or prodrug thereof. The active ingredient can be in the form a single optical isomer. Typically, one optical isomer will be present in greater than 85%, 90%, 95%, or 99% by weight compared to the other optical isomer. It will be appreciated that the composition can also include at least one additional active ingredient, for example a second therapeutic. Additional description of the disclosed pharmaceutical compositions is provided below.

A. Epigallocatechin Gallate (EGCG)

Green tea is made from the *Camellia sinensis* plant. It is rich in catechin polyphenols, in particular, epigallocatechin gallate (EGCG). EGCG has not been found in any other plant, but is the main catechin found in tea (Sharangi, Food Research International 2009; 42: 5-6.). EGCG is on the FDA's list as a safe consumption product. (Paterson, et al., Science 2005; 310: 451-453.) Scientists have shown that EGCG is able to inhibit HIV by inhibiting the binding of an envelope glycoprotein (gp120) to its receptor (CD4) (Williamson, et al., Journal of Allergy Clinical Immunology. 2006; 118: 1369-1374). Influenza is also inhibited by EGCG through interaction with the hemagglutinin envelope glycoprotein, which may lead to an alteration in the envelope structure (Song, et al., Antivirus Response. 2005; 68: 66-74). In addition, EGCG also inhibits hepatitis B by interfering with viral DNA synthesis and thus stopping viral replication. (He, et al., World Journal of Gastroenterology. 2011; 17(11): 1507-1514).

While green tea has also been the subject of several other studies, virologists have tried to focus on whether it has the ability to inhibit different viral infections. In a study conducted with Vero cells and both HSV-1 and HSV-2, researchers concluded that EGCG successfully inhibited HSV infection in a concentration dependent manner. Other green tea catechins were also tested, but only EGCG produced the inhibitory effect. Results also showed that treating Vero cells treated with EGCG following adsorption and entry of HSV-1 does not inhibit the viral production. EGCG has to be applied before the virus is adsorbed in order for an effect to be seen. Also, after treatment of Vero cells with EGCG, the envelope of HSV virions was damaged. As a result, EGCG seemed to have a direct effect on the inhibition of HSV (Isaacs, et al., Antimicrobial Agents and Chemotherapy. 2008; 52(3):962-970).

When ECGC treated HSV-1 and non-treated HSV-1 were immunogold labeled with antibodies against gB, gD, and a capsid protein, there was a 30% and a 40% drop in the treated compared to untreated virions. Therefore, once the virus is treated with EGCG its envelope glycoproteins have a decreased ability to bind to the monoclonal antibodies (Isaacs, et al., Antimicrobial Agents and Chemotherapy. 2008; 52(3):962-970).

There is no doubt now that the EGCG compound in green tea inhibits HSV, but a problem one would face when preparing a topical application with EGCG is that it is highly unstable and oxidizes very quickly, losing its antiviral abilities long before one would be able to apply it. Most of the studies done with EGCG, have to be done with freshly prepared EGCG, otherwise it loses it potent antiviral activity (Chen, et al., Journal of Zhejiang University Science. 2003; 6:714-718; Chen, et al., Handbook of Green Tea and Health Research. ISBN 978-1-60741-045-4 Editor: H. McKinley and M. Jamieson, pp. © 2009 Nova Science Publishers, Inc.). Also, since EGCG is water soluble, one would not be able to benefit from it as a topical application B. Modified Green Tea Polyphenol Compositions Green tea polyphenols have poor solubility in lipid medium. Therefore, lipophilic tea polyphenols are also disclosed for use in lipid-soluble medium. Lipophilic tea polyphenols (LTP or Modified green tea polyphenols) can be prepared by catalytic esterification of a green tea polyphenols (GTP).

Compositions containing green tea polyphenols modified to increase the permeability of the green tea polyphenols to skin and cell membranes or increase their solubility in hydrophobic media relative to unmodified green tea polyphenols are therefore provided. Green tea polyphenols that can be modified include, but are not limited to (−)-epicatechin (EC), (−)-epigallocatechin (EGC), (−)-epicatechin-3-gallate (ECG), (−)-epigallocatechin-3-gallate (EGCG), proanthocyanidins, enantiomers thereof, epimers thereof, isomers thereof, combinations thereof, and prodrugs thereof. One embodiment provides a green tea polyphenol having an ester-linked $C_1$ to $C_{30}$ hydrocarbon chain, for example a fatty acid, at one or more positions. Another embodiment provides a green tea polyphenol having one or more cholesterol groups linked to the polyphenol. The cholesterol group can be linked for example by an ether linkage directly to the polyphenol or a $C_1$ to $C_{10}$ linker can connect the cholesterol group to the polyphenol.

Another embodiment provides a green tea polyphenol compound having one or more acyloxy groups, wherein the acyl group is $C_1$ to $C_{30}$. It is believed that the addition of alkyl, alkenyl, or alkynyl chains, for example via fatty acid esterification, to green tea polyphenols increases the stability of the green tea polyphenols and increases the solubility of the green tea polyphenols in hydrophobic media including lipids, fats, soaps, detergents, surfactants or oils compared to unmodified green tea polyphenols. Green tea polyphenols having one or more hydrocarbon chains, for example ester-linked $C_1$ to $C_{30}$ groups or $C_1$ to $C_{30}$ acyloxy groups are believed to more permeable to skin or cell membranes and thereby enable the ester-linked hydrocarbon chain containing or acyloxy containing green tea polyphenol to readily enter a cell and have a biological effect on the cell, for example modulating gene expression, compared to unmodified green tea polyphenols. It will be appreciated that one or more hydrocarbon chains can be linked to the green tea polyphenol using linkages other than ester linkages, for example thio-linkages. Esterified green tea polyphenols can be combined with oils, detergents, surfactants, or combinations thereof to produce compositions which clean the skin and deliver green tea polyphenols to the skin. The oils, detergents, or surfactants advantageously increase the stability of green tea polyphenols by reducing contact of the green tea polyphenols with aqueous media. Certain embodiments provide single optical isomers, enantiomers, or epimers of the disclosed modified green tea polyphenols. Other embodiments provide compositions containing single optical isomers, enantiomers, or epimers or the disclosed modified green tea polyphenols.

One embodiment provides a compound according to Formula I:

Formula I

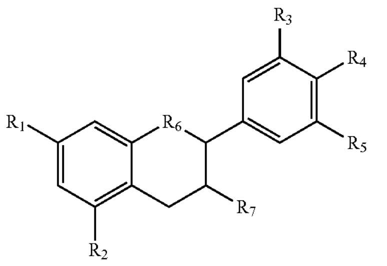

wherein $R_1$, $R_2$, $R_3$, $R_4$, $R_5$, and $R_7$ are each independently H, OH,

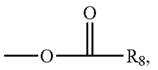 or 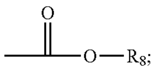

wherein $R_8$ is a linear, branched or cyclic, saturated or unsaturated, substituted or unsubstituted $C_1$-$C_{30}$ group, wherein if $R_8$ is cyclic, $R_8$ is a $C_3$-$C_{30}$ group; and $R_6$ is O, —$NR_9R_{10}$, or S, wherein $R_9$ and $R_{10}$ are independently hydrogen, or a linear, branched, or cyclic, saturated or unsaturated, substituted or unsubstituted $C_1$-$C_{30}$ group, wherein if $R_9$ and/or $R_{10}$ are cyclic, $R_9$ and/or $R_{10}$ are $C_3$-$C_{30}$ groups;

wherein at least one of $R_1$, $R_2$, $R_3$, $R_4$, $R_5$, $R_7$, $R_9$, or $R_{10}$ is

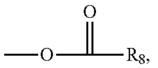 or 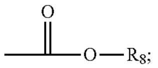

or a pharmaceutically acceptable salt or prodrug thereof, optionally in combination with an excipient.

In preferred embodiments of Formula I, $R_8$ is a linear or branched alkyl chain. In more preferred embodiments of Formula I, $R_8$ is a linear or branched $C_{16}$-$C_{25}$ alkyl group. In particularly preferred embodiments of Formula I, $R_8$ is a $C_{17}H_{35}$ group.

One embodiment provides a compound according to Formula I as described above, provided $R_4$ is not

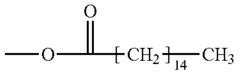

when $R_1$, $R_2$, $R_3$, $R_5$, and $R_7$ are OH;
or a pharmaceutically acceptable salt or prodrug thereof, optionally in combination with an excipient.

One embodiment provides a compound according to Formula I as described above wherein at least two of $R_1$, $R_2$, $R_3$, $R_4$, $R_5$, or $R_7$ are independently

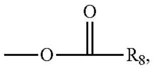 or 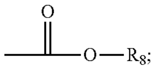

provided $R_4$ is not

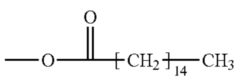

when $R_1$, $R_2$, $R_3$, $R_5$ are OH, and $R_7$ is

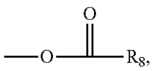 or 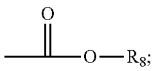

or a pharmaceutically acceptable salt or prodrug thereof, optionally in combination with an excipient.

Another embodiment provides a compound according to Formula I as described above wherein at least three of $R_1$, $R_2$, $R_3$, $R_4$, $R_5$, or $R_7$ are independently

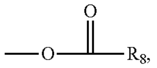 or 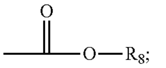

or a pharmaceutically acceptable salt or prodrug thereof, optionally in combination with an excipient.

Still another embodiment provides a compound according to Formula I as described above wherein at least four of $R_1$, $R_2$, $R_3$, $R_4$, $R_5$, or $R_7$ are independently

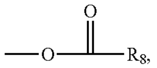 or 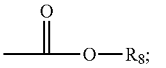

or a pharmaceutically acceptable salt or prodrug thereof, optionally in combination with an excipient.

Another embodiment provides a compound according to Formula II:

Formula II

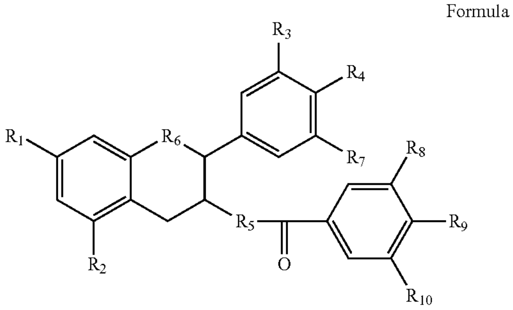

wherein $R_1$, $R_2$, $R_3$, $R_4$, $R_7$, $R_8$, $R_9$, and $R_{10}$ are each independently H, OH,

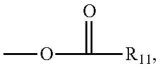 or 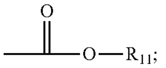

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

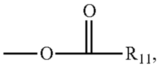 or 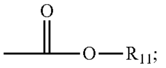

or a pharmaceutically acceptable salt or prodrug thereof, optionally in combination with an excipient.

In preferred embodiments of Formula II, $R_1$, is a linear or branched alkyl chain. In more preferred embodiments of Formula II, $R_{11}$ is a linear or branched $C_{16}$-$C_{25}$ alkyl group. In particularly preferred embodiments of Formula II, $R_{11}$ is a $C_{17}H_{35}$ group.

Another embodiment provides a compound according to Formula II wherein at least two of $R_1$, $R_2$, $R_3$, $R_4$, $R_7$, $R_8$, $R_9$, and $R_{10}$ are independently

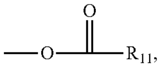 or 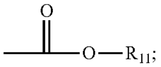

or a pharmaceutically acceptable salt or prodrug thereof, optionally in combination with an excipient.

Another embodiment provides a compound according to Formula II as described above wherein at least three of $R_1$, $R_2$, $R_3$, $R_4$, $R_7$, $R_8$, $R_9$, and $R_{10}$ are independently

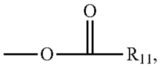 or 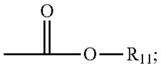

optionally in combination with an excipient.

Another embodiment provides a compound according to Formula II as described above wherein at least four of $R_1$, $R_2$, $R_3$, $R_4$, $R_7$, $R_8$, $R_9$, and $R_{10}$ are independently

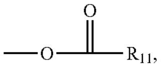 or 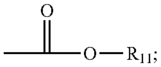

optionally in combination with an excipient.

Another embodiment provides a compound according to Formula II wherein $R_1$, $R_2$, $R_3$, $R_4$, $R_7$, $R_8$, $R_9$, and $R_{10}$ are each independently H, OH,

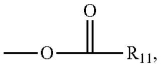 or 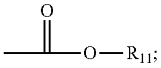

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

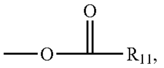 or 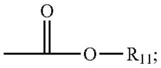

and wherein $R_4$ is not

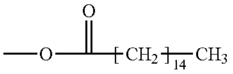

when $R_1$, $R_2$, $R_3$, $R_7$, $R_8$, $R_9$, and $R_{10}$ are OH;

or a pharmaceutically acceptable salt or prodrug thereof, optionally in combination with an excipient.

Another embodiment provides a composition including a compound according to Formula II wherein at least two of $R_1$, $R_2$, $R_3$, $R_4$, $R_7$, $R_8$, $R_9$, and $R_{10}$ are independently

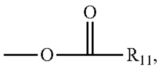 or 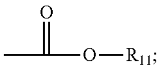

or a pharmaceutically acceptable salt or prodrug thereof, optionally in combination with an excipient.

Another embodiment provides a composition including a compound according to Formula II as described above wherein at least three of $R_1$, $R_2$, $R_3$, $R_4$, $R_7$, $R_8$, $R_9$, and $R_{10}$ are independently

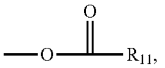 or 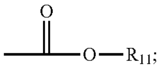

optionally in combination with an excipient.

Another embodiment provides a composition including a compound according to Formula II as described above wherein at least four of $R_1$, $R_2$, $R_3$, $R_4$, $R_7$, $R_8$, $R_9$, and $R_{10}$ are independently

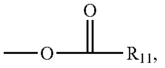 or 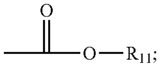

optionally in combination with an excipient.

Another embodiment provides a composition including a compound according to Formula II wherein $R_1$, $R_2$, $R_3$, $R_4$, $R_7$, $R_8$, $R_9$, and $R_{10}$ are each independently H, OH,

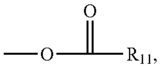 or 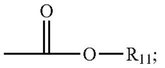

$R_{11}$ is a linear, branched, or cyclic, saturated or unsaturated, substituted or unsubstituted $C_1$-$C_{30}$ group, wherein if $R_{11}$ is cyclic, $R_{11}$ is a $C_3$-$C_{30}$ group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

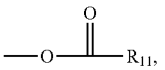 or 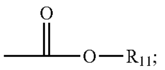

and wherein $R_4$ is not

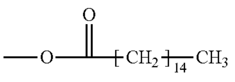

when $R_1$, $R_2$, $R_3$, $R_7$, $R_8$, $R_9$, and $R_{10}$ are OH;

or a pharmaceutically acceptable salt or prodrug thereof, optionally in combination with an excipient.

One embodiment provides a compound according to Formula III:

Formula III

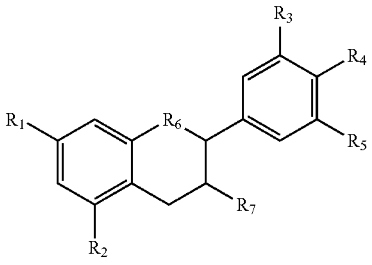

wherein $R_1$, $R_2$, $R_3$, $R_4$, $R_5$, and $R_7$ are each independently H, OH,

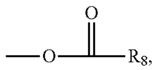 or 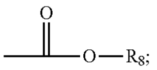

wherein $R_8$ is a linear or branched $C_{16}$-$C_{25}$ alkyl group.

$R_6$ is O, —$NR_9R_{10}$, or S, wherein $R_9$ and $R_{10}$ are independently hydrogen, or a linear, branched, or cyclic, saturated or unsaturated, substituted or unsubstituted $C_1$-$C_{30}$ group, wherein if $R_9$ and/or $R_{10}$ are cyclic, $R_9$ and/or $R_{10}$ are $C_3$-$C_{30}$ groups;

wherein at least one of $R_1$, $R_2$, $R_3$, $R_4$, $R_5$, $R_7$, $R_9$, or $R_{10}$ is

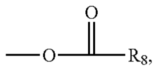 or 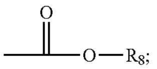

or a pharmaceutically acceptable salt or prodrug thereof, optionally in combination with an excipient.

In particularly preferred embodiments of Formula III, $R_8$ is a $C_{17}H_{35}$ group.

One embodiment provides a compound according to Formula III as described above, wherein one or more of $R_1$, $R_2$, $R_3$, $R_4$, $R_5$, or $R_7$ is

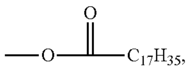 or 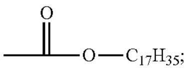

or a pharmaceutically acceptable salt or prodrug thereof, optionally in combination with an excipient.

One embodiment provides a compound according to Formula III as described above, wherein at least two of $R_1$, $R_2$, $R_3$, $R_4$, $R_5$, or $R_7$ are independently

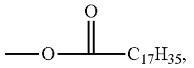 or 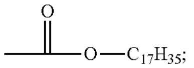

or a pharmaceutically acceptable salt or prodrug thereof, optionally in combination with an excipient.

Another embodiment provides a compound according to Formula III as described above wherein at least three of $R_1$, $R_2$, $R_3$, $R_4$, $R_5$, or $R_7$ are independently

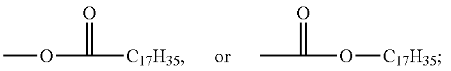

or a pharmaceutically acceptable salt or prodrug thereof, optionally in combination with an excipient.

Still another embodiment provides a compound according to Formula III as described above wherein at least four of $R_1$, $R_2$, $R_3$, $R_4$, $R_5$, or $R_7$ are independently

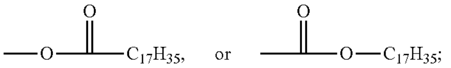

or a pharmaceutically acceptable salt or prodrug thereof, optionally in combination with an excipient.

Another embodiment provides a compound according to Formula IV:

Formula IV

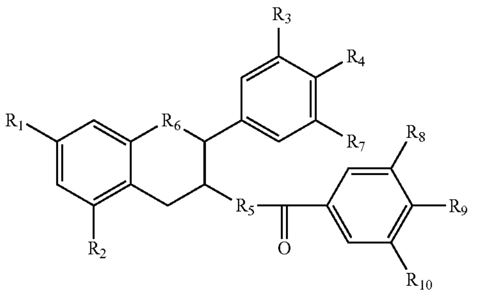

wherein $R_1$, $R_2$, $R_3$, $R_4$, $R_7$, $R_8$, $R_9$, and $R_{13}$ are each independently H, OH,

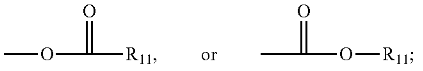

$R_{11}$ is a linear or branched $C_{16}$-$C_{25}$ alkyl group;

$R_5$ and $R_6$ are independently O, —$NR_{12}R_{13}$ or S, wherein $R_{12}$ and $R_{13}$ are independently hydrogen, or a linear, branched, or cyclic, saturated or unsaturated, substituted or unsubstituted $C_1$-$C_{30}$ group, wherein if $R_{12}$ and/or $R_{13}$ are cyclic, $R_{12}$ and/or $R_{13}$ are $C_3$-$C_{30}$ groups; and wherein at least one of $R_1$, $R_2$, $R_3$, $R_4$, $R_7$, $R_8$, $R_9$, and $R_{10}$ are independently

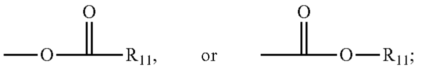

or a pharmaceutically acceptable salt or prodrug thereof, optionally in combination with an excipient.

In particularly preferred embodiments of Formula IV, $R_{11}$ is a $C_{17}H_{35}$ group.

One embodiment provides a compound according to Formula IV as described above, wherein one or more of $R_1$, $R_2$, $R_3$, $R_4$, $R_7$, $R_8$, $R_9$, and $R_{10}$ is

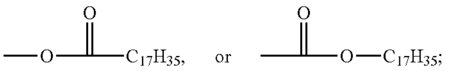

or a pharmaceutically acceptable salt or prodrug thereof, optionally in combination with an excipient.

Another embodiment provides a compound according to Formula IV wherein at least two of $R_1$, $R_2$, $R_3$, $R_4$, $R_7$, $R_8$, $R_9$, and $R_{10}$ are independently

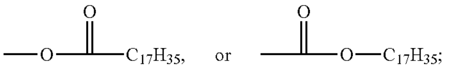

or a pharmaceutically acceptable salt or prodrug thereof, optionally in combination with an excipient.

Another embodiment provides a compound according to Formula IV as described above wherein at least three of $R_1$, $R_2$, $R_3$, $R_4$, $R_7$, $R_8$, $R_9$, and $R_{10}$ are independently

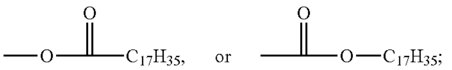

optionally in combination with an excipient.

Another embodiment provides a compound according to Formula IV as described above wherein at least four of $R_1$, $R_2$, $R_3$, $R_4$, $R_7$, $R_8$, $R_9$, and $R_{10}$ are independently

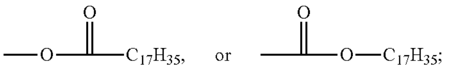

optionally in combination with an excipient.

Another embodiment provides a composition including a compound according to Formula IV wherein at least one of $R_1$, $R_2$, $R_3$, $R_4$, $R_7$, $R_8$, $R_9$, and $R_{10}$ are independently

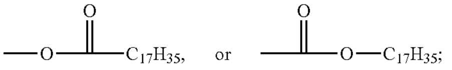

or a pharmaceutically acceptable salt or prodrug thereof, optionally in combination with an excipient.

Another embodiment provides a composition including a compound according to Formula IV wherein at least two of $R_1$, $R_2$, $R_3$, $R_4$, $R_7$, $R_8$, $R_9$, and $R_{10}$ are independently

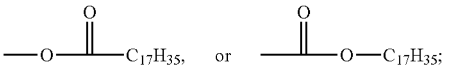

or a pharmaceutically acceptable salt or prodrug thereof, optionally in combination with an excipient.

Another embodiment provides a composition including a compound according to Formula IV as described above wherein at least three of $R_1$, $R_2$, $R_3$, $R_4$, $R_7$, $R_8$, $R_9$, and $R_{10}$ are independently

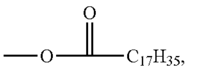 or 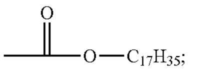

optionally in combination with an excipient.

Another embodiment provides a composition including a compound according to Formula IV as described above wherein at least four of $R_1$, $R_2$, $R_3$, $R_4$, $R_7$, $R_8$, $R_9$, and $R_{10}$ are independently

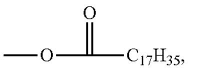 or 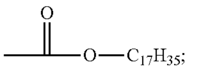

optionally in combination with an excipient.

In one embodiment, a green tea polyphenol esterified with one fatty acid is provided. Another embodiment provides a green tea polyphenol esterified with at least two fatty acids. Certain embodiments provide a green tea polyphenol esterified with one or more fatty acids having a hydrocarbon chain greater than 16 carbons. Preferred embodiments provide a green tea polyphenol esterified with one or more fatty acids having a hydrocarbon chain of between 17 and 25 carbons in length. Particularly preferred embodiments provide a green tea polyphenol esterified with one or more stearic acid chains. Representative green tea polyphenols include, but are not limited to (−)-epicatechin (EC), (−)-epigallocatechin (EGC), (−)-epicatechin-3-gallate (ECG), (−)-epigallocatechin-3-gallate (EGCG). Representative fatty acids include, but are not limited to butanoic acid; hexanoic acid, octanoic acid, decanoic acid, dodecanoic acid, tetradecanoic acid, hexadecanoic acid, 9-hexadecenoic acid, octadecanoic acid (stearic acid), 9-octadecenoic acid, 11-octadecenoic acid, 9,12-octadecadienoic acid, 9,12,15-octadecatrienoic acid, 6,9,12-octadecatrienoic acid, eicosanoic acid, 9-eicosenoic acid, 5,8,11,14-eicosatetraenoic acid, 5,8,11,14,17-eicosapentaenoic acid, docosanoic acid, 13-docosenoic acid, 4,7,10,13,16,19-docosahexaenoic acid, and tetracosanoic acid.

EGCG Esterification

Both HSV1 and HSV2 pose a serious threat to human populations around the world, and the number of people infected with the disease each year has been shown to increase. The therapeutic usage of EGCG has been suggested previously, but EGCG in its original form would not be adequate to be implemented in a topical application without rapid oxidation and lost of antiviral activity. EGCG-ester, on the other hand, would be an ideal candidate for this purpose. Lipid esters of EGCG can be formed either enzymatically or chemically (Chen, et al., Journal of Zhejiang University Science. 2003; 6:714-718).

EGCG-ester was purified previously by Chen et al in China. This was accomplished from a catalytic esterification between green tea polyphenols and C 16-fatty acid. The esterification was obtained by mixing 4 grams of green tea polyphenols and 6.5 grams of hexadecanoyl chloride. Next, 50 mLs of ethyl acetate and a catalyst at 40° C. were added to the mixture. After 3 hours of stirring, the solution was washed three times with 30 mLs of deionized water. The organic layer was then allowed to evaporate and further dried by using a vacuum at 40° C. This resulted in 8.7 g of powder product. A schematic of the synthesis of a likely esterification between GTP and Hexadecanoyl Chloride is shown below. (Chen, et al., Journal of Zhejiang University Science. 2003; 6:714-718.)

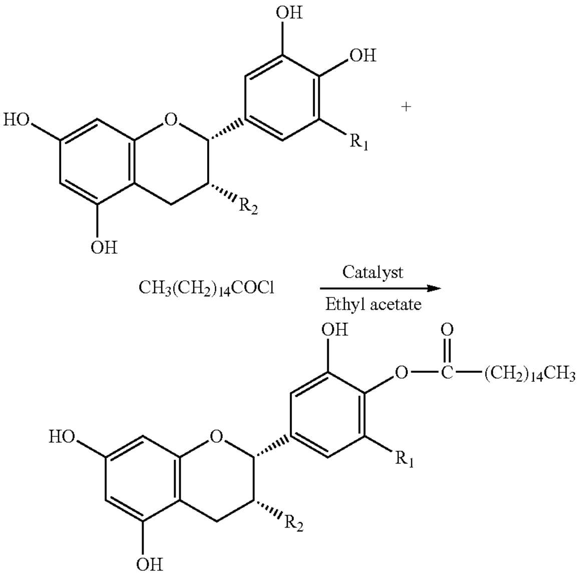

EGCG: $R_1$ = OH, $R_2$ = galloyl
EC: $R_1$ = H, $R_2$ = OH
EGC: $R_1$ = OH, $R_2$ = OH
ECG: $R_1$ = H, $R_2$ = galloyl Galloyl:

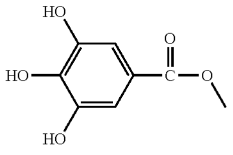

Next, high current chromatography separation was used to purify the EGCG-ester product. A two-phase solvent composed of (1:1) n-hexane-ethyl acetate-methanol-water was used in the separation column. Five grams of EGCG-ester was dissolved in 50 mL of the upper phase solution. After purification and HPLC analysis, it was seen that EGCG ester was successfully purified. The structure of an EGCG acyl-derivative is shown below. (Chen, et al., Journal of Zhejiang University Science. 2003; 6:714-718.)

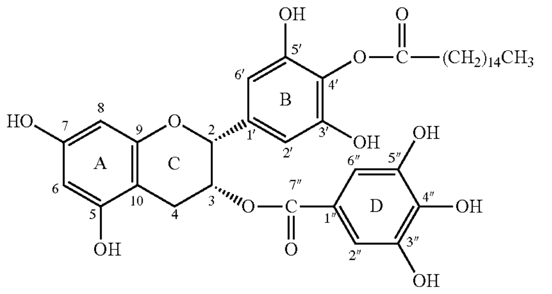

In a preferred embodiment, EGCG is esterified at the 4' position according to the structure above with stearic acid.

C. Bioactive Ingredients and Combination Therapies

Compositions containing the disclosed green tea polyphenols optionally include one more bioactive agents or additional therapeutic agents. In certain embodiments, one or more bioactive agents can be conjugated to the green tea polyphenol. Bioactive agents include therapeutic, prophylactic and diagnostic agents. These may be organic or inorganic molecules, proteins, peptides, sugars, polysaccharides, tea saponin, vitamins, cholesterol, or nucleic acid molecules. Representative vitamins include, but are not limited to lipid soluble vitamins such as vitamin D, vitamin E, or combinations thereof. Examples of therapeutic agents include proteins, such as hormones, antigens, and growth effector molecules; nucleic acids, such as antisense molecules; and small organic or inorganic molecules such as antimicrobials, antihistamines, immunomodulators, decongestants, neuroactive agents, anesthetics, amino acids, and sedatives. Examples of diagnostic agents include radioactive isotopes and radiopaque agents.

1. Anti-Psoriasis Agents

In addition to the modified green tea polyphenols, suitable anti-psoriasis agents include without limitation salicylic acid; mometasone furoate; steroids including corticosteroids such as cortisone and oluxclobetasol propionate; 5-fluorouracil; epinephrine; anthralin; vitamin D3 analogs, such as calcipotriene; methotrexate; masprocol; trimethaxate gluconate; retinoids; cyclosporin; paclitaxel; 5-amino levulinic acid; bergasol; tin-ethyl etio purpurin; benzoporphyrin derivatives; antibodies, such as ABX-IL8 antibody, CD11a monoclonal antibody and ICM3 monoclonal antibody; enzyme inhibitors, including tryptase inhibitor and phospholipase A-2 inhibitors; angiogenesis blocking agents; T-cell blocking agents and mixtures thereof.

2. Anti-Fungal Agents

A variety of known antifungal agents can be used to prepare the described compositions. A list of potential antifungal agents can be found in "Martindale—The Complete Drug Reference", 32nd Ed., Kathleen Parfitt, (1999) on pages 367-389. Suitable antifungals include, without limitation, amphotericin, amorolfine, bifonazole, bromochlorosalicyanilide, buclosamide, butenafine, butoconazole, candicidin, chlordantoin, chlormidazole, chlorphenesin, chlorxylenol, ciclopirox olamine, cilofungin, clotrimazole, croconazole, eberconazole, econazole, enilconazole, fenticlor, fenticonazole, fluconazole, flucytosine, griseofulvin, hachimycin, haloprogin, hydroxystilbamine, isethionate, iodochlorohydroxyquinone, isoconazole, itraconazole, ketoconazole, lanoconazole, luflucarban, mepartricin, miconazole, naftifine, natamycin, neticonazole, nifuroxime, nystatin, omoconazole, oxiconazole, pentamycin, propionic acid, protiofate, pyrrolnitrin, ravuconazole, saperconazole, selenium sulfide, sertaconazole, sulbentine, sulconazole, terbinafine, terconazole, tioconazole, tolciclate, tolnaftate, triacetin, timidazole, undecenoic acid, voriconazole and combinations thereof. Some of these agents are known to have antibacterial activity as well.

In one embodiment, the anti-fungal agent(s) is an azole. Suitable imidazole and triazole antifungal agents are fluconazole, timidazole, secnidazole, miconazole nitrate, econazole, haloprogin, metronidazole, itraconazole, terconazole, posaconazole, ravuconazole, ketoconazole, clotimazole, sapirconazole and combinations thereof.

In an alternative embodiment, the anti-fungal agent(s) is chlorxylenol, undecyclenic acid, selenium sulfide, iodochlorohydroxyquinone, bromochlorosalicyanilide, triacetin or combinations thereof.

Other antifungal agents include bensuldazic acid, benzoic acid, biphenamine, cloconazole, cloxyquin, dermostatin, halethazole, monensin, oxiconazole, nitrate, pecilocin, pyrithione, rubijervine, terbinafine, ticonazole, and undecylinic acid.

3. Antibacterial Agents

A variety of known antibacterial agents can be used to prepare the described compositions. A list of potential antibacterial agents can be found in "Martindale—The Complete Drug Reference", 32nd Ed., Kathleen Parfitt, (1999) on pages 112-270. Classes of useful antibacterials include aminoglycosides, antimycobacterials, cephalosporins and beta-lactams, chloramphenicols, glycopeptides, lincosamides, macrolides, penicillins, quinolones, sulphonamides and diaminopyridines, tetracyclines, and miscellaneous. In a preferred embodiment, the antibacterial agent is selected from the group consisting of metronidazole, timidazole, secnidazole, erythromycin, bactoban, mupirocin, neomycin, bacitracin, cicloprox, fluoriquinolones, ofloxacin, cephalexin, dicloxacillin, minocycline, rifampin, famciclovir, clindamycin, tetracycline and gentamycin.

Suitable aminoglycosides include antibiotics derived from *Streptomyces* and other actinomycetales, including streptomycin, framycetin, kanamycin, neomycin, paramomycin, and tobramycin, as well as gentamycin, sissomycin, netilmycin, isepamicin, and micronomycin.

Suitable antimycobacterials include rifamycin, rifaximin, rifampicin, rifabutinisoniazid, pyrazinamide, ethambutol, streptomycin, thiacetazone, aminosalicylic acid, capreomycin, cycloserine, dapsone, clofazimine, ethionamide, prothionamide, ofloxacin, and minocycline.

Cephalosporins and beta-lactams generally have activity against gram-positive bacteria and newer generations of compounds have activity against gram-negative bacteria as well. Suitable cephalosporins and beta-lactams include:

First generation; cephalothin, cephazolin, cephradine, cephaloridine, cefroxadine, cephydroxil, cefatrizine, cephalexin, pivcephalexin, cefaclor, and cefprozil.

Second generation; cephamandole, cefuroxime axetil, cefonicid, ceforanide, cefotiam, and cephamycin.

Third generation; cefotaxime, cefinenoxime, cefodizime, ceftizoxime, ceftriaxone, cefixime, cefdinir, cefetamet, cefpodoxime, ceftibuten, latamoxef, ceftazidime, cefoperazone, cefpiramide, and cefsulodin.

Fourth generation: cefepime and cefpirome

Other cephalosporins include cefoxitim, cefinetazole, cefotetan, cefbuperazone, cefminox, imipenem, meropenem, aztreonam, carumonam, and loracarbef.

Chloramphenicols inhibit gram positive and gram negative bacteria. Suitable cloramphenicols include chloramphenicol, its sodium succinate derivative, thiamphenicol, and azidamfenicol.

Suitable glycopeptides include vancomycin, teicoplanin, and ramoplanin. Suitable lincosamides include lincomycin and clindamycin, which are used to treat primarily aerobic infections.

Macrolides have a lactam ring to which sugars are attached. Suitable macrolides include erytjhromycin, as well as spiromycin, oleandomycin, josamycin, kitamycin, midecamycin, rokitamycin, azithromycin, clarithromycin, dirithromycin, roxithromycin, flurithromycin, tylosin; and streptgramins (or synergistins) including pristinamycin, and virginiamycin; and combinations thereof.

Suitable penicillins include natural penicillin and the semi-synthetic penicillins F, G, X, K, and V. Newer penicillins include phenethicillin, propicillin, methicilin, cloxacillin, dicloxacillin, flucloxacillin, oxacillin, nafcillin, ampicillin, amoxicillin, bacampicillin, hetacillin, metampicillin, pivampicillin, carbenecillin, carfecillin, carindacillin, sulbenecillin, ticarcillin, azlocillin, mezlocillin, piperacillin, temocillin, mecillinam, and pivemecillinam. Lactamase inhibitors such as clavulanic acid, sulbactam, and tazobacytam are often co-administered.

Suitable quinolones include nalidixic acid, oxolinic acid, cinoxacin, acrosoxacin, pipemedic acid, and the fluoroquinolones flumequine, ciprofloxacin, enoxacin, fleroxacin, grepafloxacin, levofloxacin, lomefloxacin, nadifloxacin, norfloxacin, ofloxacin, pefloxacin, rufloxacin, sparfloxacin, trovafloxacin, danofloxacin, enrofloxacin, and marbofloxacin.

Sulphonamides and diaminopyridines include the original of the “,sulfa” drugs, sulphanilamide, and a large number of derivatives, including sulfapyridine, sulfadiazine, sulfafurazole, sulfamethoxazole, sulfadimethoxine, sulfadimethoxydiazine, sulfadoxine, sulfametopyrazine, silver sulfadiazine, mafenide acetate, and sulfasalizine, as well as related compounds including trimethoprim, baquiloprim, brodimoprim, ormetoprim, tetroxoprim, and in combinations with other drugs such as co-trimoxazole.

Tetracyclines are typically broad-spectrum and include the natural products chlortetracycline, oxytetracycline, tetracycline, demeclocycline, and semisynthetic methacycline, doxycycline, and minocycline.

Suitable antibacterial agents that do not fit into one of the categories above include spectinomycin, mupirocin, newmycin, fosfomycin, fusidic acid, polymixins, colistin, bacitracin, gramicidin, tyrothricin, clioquinol, chloroquinaldol, haloquinal, nitrofurantonin, nitroimidazoles (including metronizole, timidazole and secnidazole), and hexamine.

The antibiotic and antifungal agents may be present as the free acid or free base, a pharmaceutically acceptable salt, or as a labile conjugate with an ester or other readily hydrolysable group, which are suitable for complexing with the ion-exchange resin to produce the resinate.

4. Antiseptic Agents

Antiseptic agents can be included in compositions formulated for topical administration. Suitable antiseptic agents include iodine, iodophores including cadexomer iodine, chlorhexidine, gluconate, thimerosal, hydrogen peroxide, and peroxides and perchlorates including organic peroxides and perchlorate salts.

5. Skin Protectants

Skin protectants can be included in compositions formulated for topical administration. Such agents not only soothe the skin but may also aide in maintaining the integrity of the skin to prevent damage. Suitable skin protectants include allantoin; cocoa butter; dimethicone; kaolin; shark liver oil; petrolatum; lanolin; vegetable oils; ethoxylated oils and lipids; polymers such as polyalkylene oxides, polyvinylpyrrolidone, polyvinyl alcohol, poly(meth)acrylates, ethylvinyl acetate, polyalkylene glycols; polysaccharides and modified polysaccharides such as hyaluronic acid, cellulose ehers, cellulose esters, hydroxypropyl methylcellulose, crosscarmelose, and starch; natural gums and resins which may be gelling or non-gelling such as alginates, carrageenans, agars, pectins, glucomannans (guar, locust bean, etc.), galactomannans (e.g. konjac), gum arabic, gum traganth, xanthan, schleroglucan and shellac; and colloidal insolubles such as zinc oxide and other insoluble zinc salts, talcum powder and other micronized natural minerals; and colloidal silicas, aluminas and other metal oxides. Additional protectants include phenolic or non-phenolic phytochemicals including, but not limited to lycopene, beta-carotene, alpha-carotene, lutein, zeaxanthin, astaxanthin, non-carotenoid, erpeniods, perillyl alcohol, saponins, terpeneol, terpene limonoids, anthocyanins, catechins, isoflavones, hesperetin, naringin, rutin, quercetin, silymarin, tangeretin, tannins, phenolic acids, ellagic acid, chlorogenic acid, p-coumaric acid (para-coumeric acid), phytic acid, ferulic acid, vanillin, cinnamic acid, hydroxycinnamic acids, curcumin, resveratrol, lignans, glucosinolates, isothiocyanates, phenethyl, sothiocyanate, benzyl isothiocyanate, sulforaphane, indoles, indole-3-carbinol, thiosulfonates, phytosterols, beta-sitosterol, anthraquinones, senna, barbaloin, hypericin, capsaicin, piperine, chlorophyll, betaine and combinations thereof.

A wide variety of sunscreen actives are suitable. The exact amount and type of sunscreen that is used depends on the level of photoprotection that is desired. Generally any agent offering protection against ultraviolet radiation by absorbing, scattering or reflecting the ultraviolet radiation may be used herein. The sunscreen agents used herein may offer protection against one or more of the following forms of sunlight radiation UVA, UVB, UVC, visible light and infrared radiation. Generally the sunprotection factor (SPF) in the final formulation varies between 2 and 30, although products with SPFs up to 100 may be formulated. The sunscreen used herein may offer chemical or physical photoprotection.

Suitable sunscreen agents include those selected from the group comprising amino benzoic acid and derivatives, such as para-amino benzoic acid (PABA), glyceryl-PABA (Lisadimate), Padimate O, Roxadimate; anthrinalates, including methylanthrynilate; benzophenones, including dioxybenzone, oxybenzone and sulisobenzone, 3-benzophenone (Uvinul M40) 4-N,N-dimethylaminobenzoic acid ester with 2,4-dihydroxybenzophenone; camphor derivatives including 3-(4-methylbenzylidene) camphor, 3-benzylidene camphor; cinnamates including DEA-p-methoxycinnamate, ethylhexyl p-methoxy cinnamate, octocrylene, octyl methoxy cinnamate; dibenzoyl methanes including butylmethoxydibenzoylmethane, salicylates including, homomethyl salicylate, octyl salicylate, trolamine methyl salicylate; metal oxides including titanium dioxide, zinc oxide and iron oxide; 2-phenylbenzimidazole-5-sulfonic acid; 4,4-methoxy-t-butyldibenzoylmethane; and mixtures thereof.

Further non-limiting examples of sunscreens useful in accordance with the present invention are described in U.S. Pat. No. 5,087,445 to Haffey et al., U.S. Pat. No. 5,073,372 to Turner et al. and U.S. Pat. No. 5,160,731 to Sabatelli et al., all of which are incorporated herein by reference in their entirety.

6. Local Anesthetics

Local anesthetics may also be employed in the topical formulation in order to lessen the pain and itching caused by the local infection. Suitable local anesthetics include benzocaine, lidocaine, dibucaine, etidocaine, benzyl alcohol, camphor, resorcinol, and menthol.

7. Antihistamines

Suitable antihistamines that can be included in the disclosed compositions include, but are not limited to diphenhdramine hydrochloride, chlorpheniramine, dimenhydrinate, loratidine, cetirizine, fexofenadine, and combinations thereof.

8. Antioxidants

The disclosed compositions can also include one or more antioxidants. Suitable antioxidants include, but are not limited to zinc, vitamin A, vitamin C, vitamin E, alpha-carotene, beta-carotene, cryptoxanthin, lycopene, lutein, zeaxathin, catechins, reserveratrol, proanthocyanidins, coenzyme Q10, and combinations thereof.

In certain embodiments, the compositions contain benzalkonium chloride, a corticosteroid, or a combination thereof.

D. Formulations

Formulations of the compounds disclosed herein including the lipid soluble green tea polyphenols according to Formula I, Formula II, or both may be prepared using pharmaceutically acceptable excipients composed of materials that are considered safe and effective and may be administered to an individual without causing undesirable biological side effects or unwanted interactions. The excipients are all components present in the pharmaceutical formulation other than the one or more lipid soluble green tea polyphenol compounds disclosed herein. As generally used herein "excipient" includes, but is not limited to, surfactants, emulsifiers, emulsion stabilizers, emollients, buffers, solvents and preservatives.

1. Excipients

Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

a. Emollients

Suitable emollients include those generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

b. Surfactants

Suitable surfactants include anionic surfactants, nonionic surfactants, cationic surfactants and ampholytic surfactants. Anionic surfactants include alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates. The alkyl or acyl group in these various compounds generally consists of a carbon-based chain containing from 8 to 30 carbon atoms.

Suitable anionic surfactants include fatty acid salts such as oleic, ricinoleic, palmitic and stearic acid salts; coconut oil acid or hydrogenated coconut oil acid; acyl lactylates, in which the acyl group contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

Suitable amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; ($C_8$-$C_{20}$) alkylbetaines, sulphobetaines, ($C_8$-$C_{20}$) alkyl-amido ($C_1$-$C_6$) alkylbetaines or ($C_8$-$C_{20}$) alkyl-amido ($C_1$-$C_6$) alkylsulphobetaines. The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Disodium cocoamphodiacetate, disodium lauroamphodiacetate, disodium capryloamphodiacetate, disodium caproamphodiacetate, disodium cocoamphodipropionate, disodium lauroamphodipropionate, disodium caproamphodipropionate, disodium capryloamphodipropionate, lauroamphodipropionate acid, and cocoamphodipropionate acid can also be used.

Representative cationic surfactants are chosen in particular from optionally polyoxyalkylenated primary, secondary or tertiary fatty amine salts; quaternary ammonium salts; imidazoline derivatives; or amine oxides of cationic nature.

Suitable quaternary ammonium salts are tetraalkylammonium halides (for example chlorides) such as, for example, dialkyldimethylammonium or alkyltrimethylammonium chlorides, in which the alkyl radical contains from about 12 to 22 carbon atoms, in particular behenyltrimethylammonium, distearyl-dimethylammonium, cetyltrimethylammonium or benzyl-dimethylstearylammonium chloride or alternatively the stearamidopropyldimethyl(myristyl acetate)ammonium chloride.

Diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chlorides or methyl sulphate in particular) and mixtures thereof can also be used. The acyl groups preferably contain 14 to 18 carbon atoms and are more particularly obtained from a plant oil such as palm oil or sunflower oil.

Additional surfactants that can be used include, but are not limited to sodium dodecylsulfate (SDS), sodium cholate, sodium deoxycholate (DOC), N-lauroylsarcosine sodium salt, lauryldimethylamine-oxide (LDAO), cetyltrimethylammoniumbromide (CTAB), and bis(2-ethylhexyl)sulfosuccinate sodium salt.

Additional non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

Representative detergents include but are not limited to alkylbenzyldimethylammonium chloride, alkyldimethylbenzylammonium chloride, sodium bis(2-ethylhexyl) sulfosuccinate, bis(2-ethylhexyl) sulfosuccinate sodium salt, 3-[(3-Cholamidopropyl)dimethylammonio]-1-propanesulfonate.

c. Emulsifiers

Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

d. Buffers

Buffers preferably buffer the composition from a pH of about 4 to a pH of about 7.5, more preferably from a pH of about 4 to a pH of about 7, and most preferably from a pH of about 5 to a pH of about 7.

The disclosed compositions can also contain at least one adjuvant chosen from the adjuvants usually used in cosmetics, such as fragrances, preserving agents, sequestering agents, wetting agents, sugars, amphoteric polymers, menthol, nicotinate derivatives, agents for preventing hair loss, foam stabilizers, propellants, dyes, vitamins or provitamins, acidifying or basifying agents or other well-known cosmetic adjuvants.

2. Encapsulation

In another embodiment, the green tea polyphenols can be incorporated into a polymeric component by encapsulation in a microcapsule. The microcapsule can be fabricated from a material different from that of the bulk of the carrier, coating, or matrix. Suitable microcapsules are those which are fabricated from a material that undergoes erosion in the host, or those which are fabricated such that they allow the green tea polyphenol to diffuse out of the microcapsule. Such microcapsules can be used to provide for the controlled release of the encapsulated green tea polyphenol from the microcapsules.

Numerous methods are known for preparing microparticles of any particular size range. In the various delivery vehicles of the present invention, the microparticle sizes may range from about 0.2 μm up to about 100 μm. Synthetic methods for gel microparticles, or for microparticles from molten materials are known, and include polymerization in emulsion, in sprayed drops, and in separated phases. For solid materials or preformed gels, known methods include wet or dry milling or grinding, pulverization, size separation by air jet, sieve, and the like.

Microparticles can be fabricated from different polymers using a variety of different methods known to those skilled in the art. Exemplary methods include those set forth below detailing the preparation of polylactic acid and other microparticles. Polylactic acid microparticles are preferably fabricated using one of three methods: solvent evaporation, as described by Mathiowitz, et al. (1990) J. Scanning Microscopy 4:329; Beck, et al. (1979) Fertil. Steril. 31: 545; and Benita, et al. (1984) J. Pharm. Sci. 73: 1721; hot-melt microencapsulation, as described by Mathiowitz, et al., Reactive Polymers 6: 275 (1987); and spray drying. Exemplary methods for preparing microencapsulated bioactive materials are set forth below.

In the solvent evaporation method, the microcapsule polymer is dissolved in a volatile organic solvent, such as methylene chloride. The green tea polyphenol (either soluble or dispersed as fine particles) is added to the solution, and the mixture is suspended in an aqueous solution that contains a surface active agent such as poly(vinyl alcohol). The resulting emulsion is stirred until most of the organic solvent has evaporated, leaving solid microparticles. The solution is loaded with the green tea polyphenol and suspended in vigorously stirred distilled water containing poly(vinyl alcohol) (Sigma). After a period of stirring, the organic solvent evaporates from the polymer, and the resulting microparticles are washed with water and dried overnight in a lyophilizer. Microparticles with different sizes (1-1000 μm) and morphologies can be obtained by this method. This method is useful for relatively stable polymers like polyesters and polystyrene. Labile polymers such as polyanhydrides, may degrade during the fabrication process due to the presence of water. For these polymers, the following two methods, which are performed in completely anhydrous organic solvents, are preferably used.

In the hot melt encapsulation method, the polymer is first melted and then mixed with the solid particles of biologically active material that have preferably been sieved to less than 50 microns. The mixture is suspended in a non-miscible solvent (like silicon oil) and, with continuous stirring, heated to about 5° C. above the melting point of the polymer. Once the emulsion is stabilized, it is cooled until the polymer particles solidify. The resulting microparticles are washed by decantation with a solvent such as petroleum ether to give a free-flowing powder. Microparticles with sizes ranging from about 1 to about 1000 microns are obtained with this method. The external surfaces of capsules prepared with this technique are usually smooth and dense. This procedure is preferably used to prepare microparticles made of polyesters and polyanhydrides.

The solvent removal technique is preferred for polyanhydrides. In this method, the green tea polyphenol is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range from about 1 to about 300 μm can be obtained by this procedure. The external morphology of spheres produced with this technique is highly dependent on the type of polymer spray drying, the polymer is dissolved in methylene chloride. A known amount of the green tea polyphenol is suspended or co-dissolved in the polymer solution. The solution or the dispersion is then spray-dried. Microparticles ranging between about 1 to about 10 μm are obtained with a morphology which depends on the type of polymer used.

In one embodiment, the green tea polyphenol is encapsulated in microcapsules that comprise a sodium alginate envelope. Microparticles made of gel-type polymers, such as alginate, are produced through traditional ionic gelation techniques: The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for about twenty to thirty minutes in order to allow sufficient time for gelation to occur. Microparticle size is controlled by using various size extruders or varying either the nitrogen gas or polymer solution flow rates.

Liposomes can aid in the delivery of the green tea polyphenol to a particular tissue and also can increase the half-life of green tea polyphenol. Liposomes are commercially available from a variety of suppliers. Alternatively, liposomes can be prepared according to methods known to those skilled in the art, for example, as described in Eppstein et al., U.S. Pat. No. 4,522,811. In general, liposomes are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al., Ann. Rev. Biophys. Bioeng. 9: 467 (1980); and U.S. Pat. Nos. 4,235,871, 4,501,728, 4,837,028, and 5,019,369. In one embodiment, the liposomes encapsulating the green tea polyphenol include a ligand molecule that can target the liposome to a particular cell or tissue at or near the site of HSV infection.

In one embodiment, the liposomes encapsulating the green tea polyphenols of the present disclosure are modified so as to avoid clearance by the mononuclear macrophage and reticuloendothelial systems, for example by having opsonization-inhibition moieties bound to the surface of the structure. In one embodiment, a liposome can comprise both opsonization-inhibition moieties and a ligand. Opsonization-inhibiting moieties for use in preparing the liposomes in one embodiment are large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016. Liposomes modified with opsonization-inhibition moieties thus remain in the circulation much longer than unmodified liposomes. For this reason, such liposomes are sometimes called "stealth" liposomes. Stealth liposomes are known to accumulate in tissues fed by porous or "leaky" microvasculature. In addition, the reduced uptake by the RES lowers the toxicity of stealth liposomes by preventing significant accumulation in the liver and spleen.

Opsonization inhibiting moieties suitable for modifying liposomes are preferably water-soluble polymers with a molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG; and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; laminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes." The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH3 and a solvent mixture such as tetrahydrofuran and water in a 30:12 ratio at 60° C.

The disclosed microparticles and liposomes and methods of preparing microparticles and liposomes are offered by way of example and are not intended to define the scope of microparticles or liposomes of use in the present disclosure. It will be apparent to those of skill in the art that an array of microparticles or liposomes, fabricated by different methods, are of use in the present invention.

E. Pharmaceutical Compositions

Another embodiment provides pharmaceutical compositions and dosage forms which include a pharmaceutically acceptable salt of one or more green tea polyphenols, modified green tea polyphenols, in particular, (−)-epigallocatechin-3-gallate or a pharmaceutically acceptable polymorph, solvate, hydrate, dehydrate, co-crystal, anhydrous, amorphous form thereof, and combinations thereof. Specific salts of disclosed compounds include, but are not limited to, sodium, lithium, potassium salts, and hydrates thereof.

Pharmaceutical unit dosage forms of green tea polyphenols are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the green tea polyphenols of the disclosure will typically vary depending on their use. A parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient, for example a green tea polyphenol, will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of green tea polyphenol in a dosage form may differ depending on factors such as, but not limited to, the route by which it is to be administered to patients. However, typical dosage forms of the green tea polyphenol compounds of the disclosure include a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Topical dosage forms of the disclosure include, but are not limited to, creams, lotions, ointments, gels, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the green tea polyphenols of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a green tea polyphenol of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a tight junction modulator can be used to further adjust the properties of the resulting composition.

The disclosed green tea polyphenol compositions can also be formulated as extended or delayed release formulations. Extended and delayed release formulations for various active ingredients are known in the art, for example by encapsulation.

Still another embodiment provides a green tea polyphenol topical dermatological spray.

The green tea polyphenol compounds, in particular the green tea polyphenols esterified with $C_1$ to $C_{30}$ hydrocarbon chain, are present in about 0.001% to about 50% w/v, typically from about 0.25% to about 20% w/v, more typically about 1% to about 15% w/v. In certain embodiments, the green tea polyphenols are present in about 10% w/v.

III. Methods of Use

The disclosed compositions containing one or more GTPs, modified GTPs, or combinations thereof are useful for the treatment of one more symptoms of a viral infection. Preferably, the disclosed compositions are formulated for topical application to the surface area of the human or animal body, including skin, hair, teeth, nails and lips.

One embodiment provides compositions including one or more of the disclosed GTPs or modified GTPs, for example those according to Formulas I or II, for treating HSV. Such compositions are formulated for topical application to the skin as described above. The formulations can be applied directly to the skin in the form of lotions, creams, salves, ointments, fluids, hydrogels, foams, colloids, suspensions, or dry powder.

The GTP composition includes an amount of one or more green tea polyphenols, modified GTPs, pharmaceutically acceptable salts, prodrugs, or derivatives thereof in an amount effective to treat one or more symptoms of a viral infection such as HSV.

The green tea polyphenol compositions can be administered to a subject, preferably a human subject, topically for 1, 2, 3, 4, 5, 6, 7 days or more as needed. The compositions can be topically applied 1, 2, 3, or more times per day as needed.

IV. Method of Making the Compositions

A. Modified Green Tea Polyphenols

Modified green tea polyphenols, preferably modified green tea polyphenols having increased lipid solubility compared to unmodified green tea polyphenols can be produced for example, by the method described in Chen and Du, (2003) Chinese J Chem, 21:979-981, which where permissible is incorporated by reference in its entirety. Briefly, a green tea polyphenol is reacted with an acyl chloride having a desired number of carbons in ethyl acetate. The reaction is filtered and the reaction solution is washed with deionized water. The upper organic layer is evaporated and dried under vacuum. The lipid soluble green tea polyphenol can be isolated using high-speed counter-current chromatography as described for example in Chen et al. (2002) J. Chromatography, 982:163-165, which where permissible is incorporated by reference in its entirety. The isolated lipid soluble green tea polyphenol can then be formulated into a composition, for example topical formulations.

The water in oil topical compositions may be in the form of emulsions such as creams, lotions, ointments, powders, micro emulsions, liposomes, or in the form of gels, liquids, and foams. They may also be presented in dry powder formulations.

B. Emulsions

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscible phase into the other and assist in stabilizing the emulsion. A comprehensive overview of emulsifying agents and their applications may be found in Becher, P. Encyclopedia of Emulsion Technology, Dekker Ed., 1983.

In one embodiment, the oil phase is prepared by mixing together one or more surfactant(s), optionally, one or more emulsifier(s), and one or more of the disclosed lipid soluble green tea polyphenols to melt if necessary. The aqueous phase is prepared separately by dissolving the preservatives in water with heating as needed. The aqueous phase is added to the oil phase, for example with continuous high shear mixing to produce a milky emulsion. The emulsion is cooled and the pH is adjusted by the addition of a buffer. The formulation is brought to the final weight by the addition of water.

The surfactants or detergents are optionally used in the compositions in proportions of between 0.01% and 50% by weight, relative to the total weight of the composition. When the compositions are in the form of shampoos, they are generally used in a proportion of at least 1% by weight, preferably between 5% and 50% by weight, relative to the total weight of the composition and in particular between 8% and 35%.

The concentration of the emulsifier(s) is from about 0.5% to about 50% by weight of the final composition. The concentration of the buffer(s) is from about 1% to about 25% by weight of the final composition and the concentration of the stabilizer(s) is from about 1% to about 25% by weight of the final composition.

The concentration of the green tea polyphenol compound or compounds is about 0.001% to about 40% by weight of the final composition, in particular about 0.001% to about 0.01% by weight. Other embodiments include concentrations of about 1.0%, 5%, 10%, 15%, 20%, 25%, 30%, or 35% of the green tea polyphenol compound or compounds. In certain embodiments one or more green tea polyphenols are present in an amount effective to reduce inflammation of the skin or treat dandruff when administered. In another embodiment one or more green tea polyphenols are present in an amount effective to reduce virus replication in a subject. The amount of the green tea polyphenol will vary according to the disorder to be treated.

The concentration of an optional topical anesthetics is from about 1% to about 10% by weight and the concentration anti-fungals and other antibiotics is from about 0.3% to about 5% by weight.

EXAMPLES

Example 1

Cell Viability Study of EGCG-Ester on Vero Cells

Materials and Methods

Green Tea Polyphenols Solutions

The two different polyphenols tested were EGCG and EGCG-ester. The concentration span we used was 12.5, 25, 50, 75, and 100

Cell Viability Assay

Vero cells were plated in 6 well plates and after a period of 24 hours different concentrations of EGCG or EGCG-ester (12.5, 25, 50, 75, 100 μM) were added to each well, respectively. After one hour, the polyphenols were aspirated and the cells were washed with PBS. DMEM media was put back into each well and cells were incubated for 24 hrs. Cells were then counted using a hemocytometer and trypan blue which stains the dead cells blue and leaves the live cells white.

Cells Culture Maintenance

Vero cells were purchased from ATCC (Manassas, Va.) and were cultured in T25 flasks containing Dulbecco Minimal Essential Media (DMEM) with 5% Fetal Bovine Serum (FBS) and 1 ug/mL gentamycin at 37° C. and 5% $CO_2$ until confluent. Cell growth was carefully monitored using an ACCU-SCOPE phase contrast microscope with attached Micrometrics digital camera and Micrometric SE Premium software. To maintain the cultures, confluent monolayers of Vero cells were trypsinized with 5004 of Trypsin/EDTA for 5 minutes. 4.5 mLs of media was then added to the T-25 flask and cells were subcultured into 6 well plates or other T-25 flasks and incubated until confluent.

Results

HSV plaque assays using Vero cells were conducted with and without the addition of epigallocatechin gallate (EGCG). Untreated HSV plaques resulted in a viral titer of $1.03\times10^7$ PFU/ml. When 100 μM EGCG was applied, no viral plaques were observed. These results show that EGCG inhibited HSV infection.

Additionally, cell viability assays were conducted with and without the addition of epigallocatechin gallate (EGCG) and Lipophilic tea polyphenols (LTP). The results of those assays are shown in Table 1.

TABLE 1

Results of Cell Viability Assay

| | Cells | Cells dead |
|---|---|---|
| Control | 218 | 67 |
| | 145 | 39 |
| | 396 | 159 |
| 100 μM EGCG | 292 | 134 |
| | 347 | 184 |
| | 167 | 119 |
| 100 μM LTP | 79 | 45 |
| | 71 | 41 |
| | 94 | 49 |

The cytotoxicity study indicated that EGCG and EGCG-ester at concentrations of 12.5 to 75 μM do not induce a change cell morphology. The cell viability was determined by using trypan blue and hemacytometer direct cell count to detect the effect of EGCG-ester on Vero cells. The results are shown in FIG. 1 and Table 2. As the concentration of EGCG-ester is increased, the percentage of cell death is not changed. Therefore, the maximum nontoxic concentration, 75 μM EGCG-ester, can be used to treat HSV 1 and study its inhibitory effects.

TABLE 2

Cell viability data of vero cells treated with different concentrations of EGCG-ester

| | 0 μM | 12.5 μM | 25 μM | 50 μM | 75 μM |
|---|---|---|---|---|---|
| Live cells | 4.01E+07 | 2.56E+07 | 2.72E+07 | 2.89E+07 | 2.71E+07 |
| Dead cells | 1.45E+06 | 2.7E+06 | 2.95E+06 | 2.90E+06 | 1.70E+06 |
| % of death | 3.60% | 10% | 10% | 10% | 10% |

The percentage of cell death did not change much when cells were treated with EGCG-ester compared to control.

Example 2

Cytotoxicity Study for EGCG and EGCG-Ester

Methods and Materials

Cytotoxicity Assay

Vero cells were plated in 6 well plates with different concentrations (12.5, 25, 50, 75, 100 μM), of EGCG or EGCG-ester. Cells were studied for morphological and proliferation changes 48 hrs later using an ACCU-Scope 3002 microscope with a camera attached.

Alternatively, Vero cells were plated in 6 well plates and after a period of 24 hours, different concentrations (12.5, 25, 50, 75, 100 μM) of EGCG or EGCG-ester were added to each well respectively. After one hour, the polyphenols were aspirated and the cells were washed with PBS. Cells were studied for morphological and proliferation changes 24 hrs later using an ACCU-Scope 3002 microscope with a camera attached.

Cells Culture Maintenance

Vero cells were purchased from ATCC (Manassas, Va.) and were cultured in T25 flasks containing Dulbecco Minimal Essential Media (DMEM) with 5% Fetal Bovine Serum (FBS) and 1 ug/mL gentamycin at 37° C. and 5% $CO_2$ until confluent. Cell growth was carefully monitored using an ACCU-SCOPE phase contrast microscope with attached Micrometrics digital camera and Micrometric SE Premium software. To maintain the cultures, confluent monolayers of Vero cells were trypsinized with 500 μL of Trypsin/EDTA for 5 minutes. 4.5 mLs of media was then added to the T-25 flask and cells were subcultured into 6 well plates or other T-25 flasks and incubated until confluent.

Results

The cells were not significantly affected by using the higher concentration of EGCG and EGCG-ester.

In order to determine the proper concentrations of EGCG and EGCG-ester to be used for treating HSV1, the effect of polyphenols on the cells were studied. Different concentrations of EGCG and EGCG-ester (12.5, 25, 50, 75, 100 μM) were evaluated and both the growth and morphology of the cells were observed at 48 hrs. In this experiment, the polyphenols were added at the same time as the cells were plated and were not removed subsequently.

Experiments to assess the cytotoxicity of green tea polyphenols for cultured eukaryotic cells indicate a moderate toxic behavior of these polyphenols in cell cultures. The results indicate that when EGCG is added to Vero cells, there are no morphological changes seen in the concentrations used. In the presence of EGCG-ester the maximum nontoxic concentration was evaluated to be 75 μM. At the concentration of 100 μM, cell morphology is affected to a certain extent.

The effect of different concentrations of EGCG-ester on Vero cells was also observed at 24 hrs. Since in the procedures for HSV1 infected cultures, after 1 hr adsorption, the media and unabsorbed virus are aspirated, it is important to determine the effect of polyphenols under similar conditions. In this study, Vero cells were plated first for 24 hours and then different concentrations of EGCG-ester (12.5, 25, 50, 75, 100 μM) were added to the cells and allowed to adsorb for 1 hour. EGCG-ester was then aspired, and cells were observed 24 hours later.

As the concentration of EGCG-ester is increased, cell morphology was not greatly affected. This is therefore the method used for subsequent experiments.

The effect of EGCG and EGCG-ester on HSV1 and Vero cells have been studied using different approaches to establish the concentrations that do not affect the host cells but efficiently inhibits the virus. First, in the cell cytotoxicity assay, as the concentration of polyphenols increased, cell morphology did change a little. This was seen when polyphenols were added at the same time as cells were plated. On the other hand, when the polyphenols were added for 1 hr after the cells had already been plated for 24 hrs, and then consequently removed, cell morphology did not seem to be affected.

Example 3

Effects of EGCG-Ester on HSV Infection

Methods and Materials

Cells Culture Maintenance

Vero cells were purchased from ATCC (Manassas, Va.) and were cultured in T25 flasks containing Dulbecco Minimal Essential Media (DMEM) with 5% Fetal Bovine Serum (FBS) and 1 ug/mL gentamycin at 37° C. and 5% $CO_2$ until confluent. Cell growth was carefully monitored using an ACCU-SCOPE phase contrast microscope with attached Micrometrics digital camera and Micrometric SE Premium software. To maintain the cultures, confluent monolayers of Vero cells were trypsinized with 5004, of Trypsin/EDTA for 5 minutes. 4.5 mLs of media was then added to the T-25 flask and cells were subcultured into 6 well plates or other T-25 flasks and incubated until confluent.

Fluorescence Microscopy

Green fluorescence HSV biosynthesis was observed in control Vero cells using fluorescence microscopy and Differential Interference Contrast (DIC) microscopy. Cells were grown on glass cover slips and allowed to reach confluence. They were then infected with either control HSV or previously treated HSV for 1 hour. Time course studies were performed in which the virus was allowed to adsorb for 1 hour and then aspirated. Cells were washed with PBS and media was added to each well. After a period of 8, 10, and 12 hours, cells were then fixed with a 1:1 acetone and methanol solution and visualized under a Zeiss Axiovision fluorescence microscope using differential interference contrast settings.

The lytic cycle of HSV1/Vero cells was observed at 8, 10, 12 hours postinfection to study the molecular changes within the infected cells. HSV1/Vero cells were used as positive controls and Vero cells were used as negative control. 75 μM EGCG ester-HSV1/Vero cells were also monitored and compared to controls. GFP-HSV1, DAPI stained nucleus and lysosome stain were used to identify cytopathic effects on Vero cells. The course study was performed in triplicates.

A single cell was treated without HSV1 infection and EGCG-ester treatment. The untreated cell was used as a reference to compare to all the treated samples. The cells with DAPI stained nuclei have very smooth margin and no granules within the nucleus. In the green fluorescence image, there is an obvious green background, but no green fluorescence particles. In the lysosome stain, although there is a red background, there are no obvious fluorescence red particles inside the cells.

Next, uninfected Vero cells in a monolayer without any treatment were observed under 400× magnification. Images were taken of the phase contrast microscopy, DAPI, GFP, DAPI+GFP, DAPI+GFP+*Lysosome* stains and an all stain-overlay. Overall, the experiment provides information of the cell morphology and the background for all the fluorescence staining.

Results

HSV1/Vero cells and EGCG-ester-HSV1/Vero cells were observed 8 hrs post infection. Phase contrast image for HSV1/Vero cells are very different from EGCG-ester-HSV1/Vero cells. The cell morphology was greatly changed, indicating lytic viral infection in the HSV1/Vero cells. Cell morphology of EGCG-ester-HSV1/Vero is very similar to the cells alone image. Virus treated with 100 μM EGCG or 100 μM EGCG-ester were not able to replicate and form more virions. The results imply that HSV1 was not able to continue with its lytic cycle when treated with EGCG ester. When staining the HSV1/Vero cells with DAPI stain, there is an obvious difference in the cell nucleus compared to the EGCG-ester-HSV1/Vero cells. Significant granulation as well as demargination is only seen in the HSV1/Vero cells, demonstrating a normal occurrence of viral infection.

EGCG-ester-HSV1/vero cells still maintained their nuclear integrity and show similar appearance to the cells only image. Green fluorescence images clearly indicate a significant amount of GFP expression in the HSV1/Vero cells but almost none in the EGCG-ester-HSV1/Vero cells. In addition, the lysosome stain demonstrates lysosome activation in the HSV1/vero cells but not in the EGC-ester-HSV1/vero cells.

In the 10 hours post infection images, the cell morphology is significantly changed in HSV1/Vero cells, even more so than 8 hours post infection. EGCG-ester-HSV1/Vero cells look very similar to the cells only image. In the HSV1/Vero cells DAPI stain, there is even further granulation and demargination in the cell nucleus. Green fluorescence particles are also observed in the HSV1/Vero cells only. *Lysosome* stain showed no significant activation for HSV1/Vero cells in the 10 hours post infection. On the contrary, EGCG-ester-HSV1/Vero cells demonstrate similar results to the 8 hours post infection in all of the fluorescence images.

In the 12 hours post infection experiment, the cell morphology remained similar to cells at 8 and 10 hrs post infection. More granulation and demargination are seen at this stage of infection in the HSV1/Vero cells when stained with DAPI. Green fluorescence particles are also observed. No lysosome activation was observed. EGCGester HSV1/Vero cells shows similar results to the 8 and 10 hours post infection cells in all the fluorescence images as well as similar to the cells only images.

In summary, when comparing and contrasting the results of the fluorescence microscopy, it is clear to the observer the differences between HSV1/Vero cells and 75 μM EGCG-ester HSV1/Vero cells. There are visible viral particles in the cells infected with HSV1 and almost no virions in the cells infected with EGCG-ester-HSV1.

The nucleus of the cells is also very different. In the cells infected with HSV1, the margin of cells is lost, and there is granulation of the chromosomes. In the cells infected EGCG-ester-HSV1, the nucleus of the cells were not affected.

Green fluorescence particles are seen from 8 to 12 hours post infection in the HSV1/Vero cells. The amount of nuclear granulation and demargination are increased from 8 to 10 hours post infection in the HSV1/Vero cells. *Lysosome* activation can be seen at 8 hours but decreases at 10 hours post infection in HSV1/Vero cells. These results correlate well with reported events in HSV1/Vero cells lytic infection. None of this was observed in the EGCG-ester HSV1/Vero cells indicating that EGCG-ester at 75 μM is able to inhibit HSV1 infections.

In the fluorometer experiment, GFP expression is much lower at 75 EGCGester HSV1/Vero cells compared to HSV1/Vero cells. Thus, expression of GFP as part of viral biosynthesis is decreased when HSV1 is treated with EGCG-ester. In addition, the fluorescent microscopy analyses showed remarkable results with both the GFP and DAPI stain. GFP expression was reduced in the 75 μM-EGCG-ester HSV1/Vero cells as compared to HSV1/Vero cells. Also, when evaluating the morphology of the nuclei of the HSV1/Vero cells to the EGCG-ester-HSV1/Vero cells several differences are seen. The nuclei of the HSV1/Vero cells lose their margins during infection, and there is major granulation of the chromosomes. On the contrary, the nuclei of the EGCG-ester-HSV1/Vero cells keep their integrity throughout infection.

Example 4

EGCG-Ester Does Not Inhibit Cell Proliferation

Materials and Methods

Cell Proliferation Assay

A cell proliferation kit (G5421, Promega Corp.) was used. This is a colorimetric method for determining cell proliferation. This kit contains a tetrazolium compound and an electron-coupling reagent (phenazine methosulfate). Only live cells will be able to bioreduce the tetrazolium compound into soluble formazan. Thus, the amount of formazan formed and measured at 490 nm absorbance is directly proportional to the number of live cells. Cells were plated into 96 well plates and after 24 hrs they were treated with different concentrations (12.5, 25, 50, 75, 100 μM) of polyphenols and allowed to adsorb for 1 hour. Polyphenols were then aspirated and 100 μL of fresh DMEM was added back to each well. 24 hours later, 20 μL of the MTS reagent was added to every 100 μL of cells in media. The plates were incubated at 37° C. and 5% $CO_2$ for 4 hours, and then the absorbance was read using a plate reader.

Results

Figure 2:
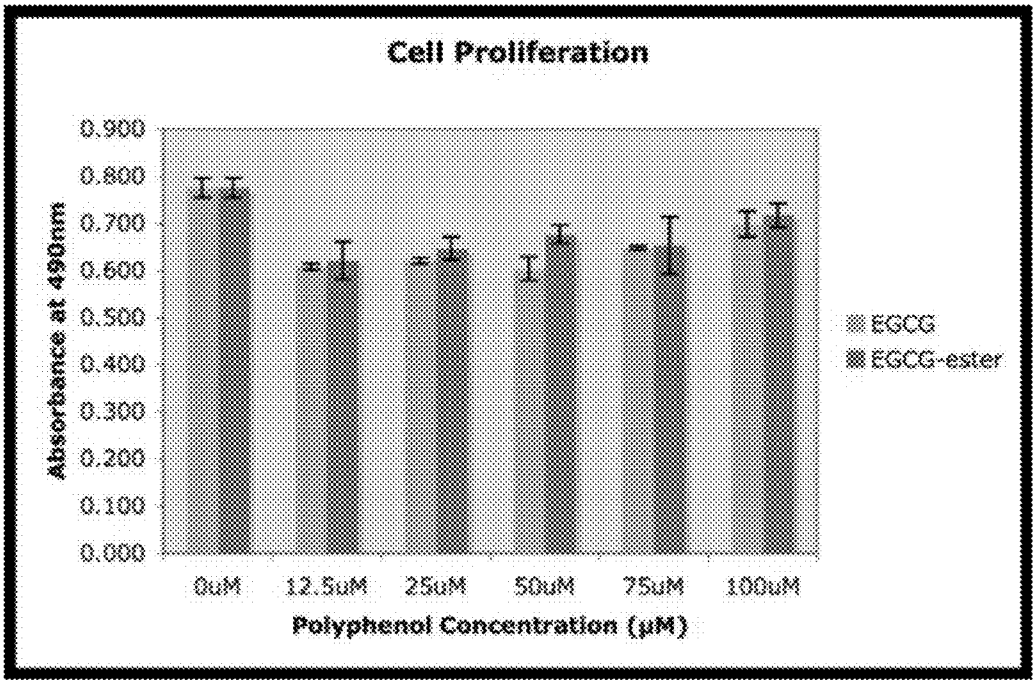
FIG. 2 is a bar graph of absorbance at 490 nm versus polyphenol concentration (μM). The bar on the left of each set represents EGCG. The bar on the right of each set represents EGCG-ester.

The previous results indicated that EGCG-ester does not show significant effect on Vero cell cytotoxicity and viability. In this study, cell proliferation was examined under the same conditions as described before. Each experiment was assayed in triplicates, and absorbance of this colorimetric assay was recorded at 490 nm using a 96 well ELISA plate reader. The results are shown in table 3 and FIG. 2.

Figure 4:
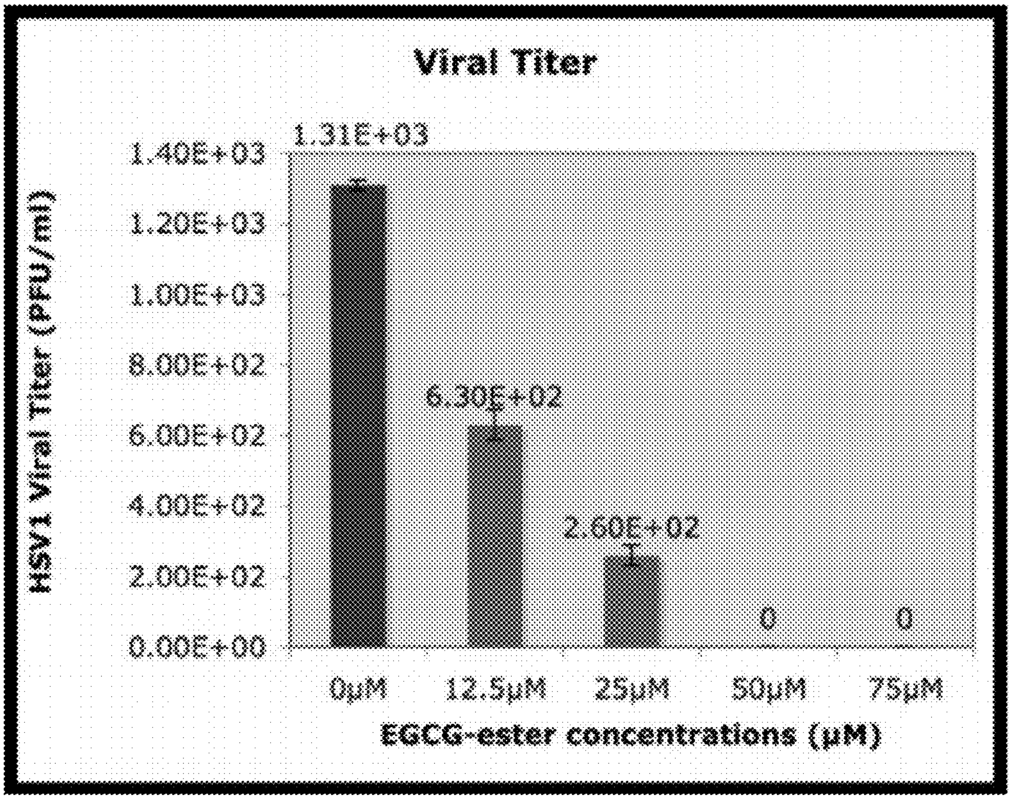
FIG. 4 is a bar graph of viral titer of HSV1 viral titer (PFU/ml) versus EGCG-ester concentrations (μM).

The proliferation assay results in table 3 and FIG. 4 indicate that both EGCG and EGCG-ester are not inhibiting cell proliferation to a great extent. In comparison to controls, cells exhibited only a small decrease in levels of 490 nm absorbance. This indicates that most of the cells are inducing high reduction of MTS tetrazolium to formazan and therefore retain high cell viability. Increases in the concentrations of EGCG and EGCG-ester up to 75 μM do not lead to a significant reduction in cell proliferation.

TABLE 3

Cell proliferation data with mean and standard deviation of Vero cells treated with different concentrations of EGCG and EGCG-Ester (A) EGCG/Vero (B) EGCG-ester/Vero.

| A | EGCG 12.5 μM | EGCG 25 μM | EGCG 50 μM | EGCG 75 μM | EGCG 100 μM | Control |
|---|---|---|---|---|---|---|
| | 0.601 | 0.616 | 0.589 | 0.652 | 0.730 | 0.780 |
| | 0.615 | 0.628 | 0.632 | 0.645 | 0.688 | 0.793 |
| | 0.606 | 0.620 | 0.587 | 0.645 | 0.677 | 0.752 |
| Mean | 0.607 | 0.621 | 0.603 | 0.647 | 0.698 | 0.775 |

| B | EGCG-ester 12.5 μM | EGCG-ester 25 μM | EGCG-ester 50 μM | EGCG-ester 75 μM | EGCG-ester 100 μM | Control |
|---|---|---|---|---|---|---|
| | 0.642 | 0.668 | 0.663 | 0.582 | 0.691 | 0.780 |
| | 0.647 | 0.651 | 0.698 | 0.689 | 0.741 | 0.793 |
| | 0.574 | 0.621 | 0.667 | 0.687 | 0.719 | 0.752 |
| Mean | 0.627 | 0.647 | 0.676 | 0.653 | 0.717 | 0.775 |

Example 5

The Effect of EGCG and EGCG-Ester on the Production of HSV1 Particles

Materials and Methods

Viral Titer Study Using Plaque Assay

Vero cells were plated on 6 well plates and allowed to reach confluence. HSV virions were treated for 1 hour with the respective concentration of polyphenols (12.5, 25, 50, 75, 100 μM) prior to cell infection. Cells were then infected with HSV and allowed to adsorb for 1 hour. Viruses that had not been absorbed were then aspirated. Plates were then overlaid with a nutrient medium-containing agar. Plaques were visualized by staining cells with crystal violet, observed, and counted within 50 hours.

Cells Culture Maintenance

Vero cells were purchased from ATCC (Manassas, Va.) and were cultured in T25 flasks containing Dulbecco Minimal Essential Media (DMEM) with 5% Fetal Bovine Serum (FBS) and 1 ug/mL gentamycin at 37° C. and 5% $CO_2$ until confluent. Cell growth was carefully monitored using an ACCU-SCOPE phase contrast microscope with attached Micrometrics digital camera and Micrometric SE Premium software. To maintain the cultures, confluent monolayers of Vero cells were trypsinized with 500 μL of Trypsin/EDTA for 5 minutes. 4.5 mLs of media was then added to the T-25 flask and cells were subcultured into 6 well plates or other T-25 flasks and incubated until confluent.

Results

Figure 3:
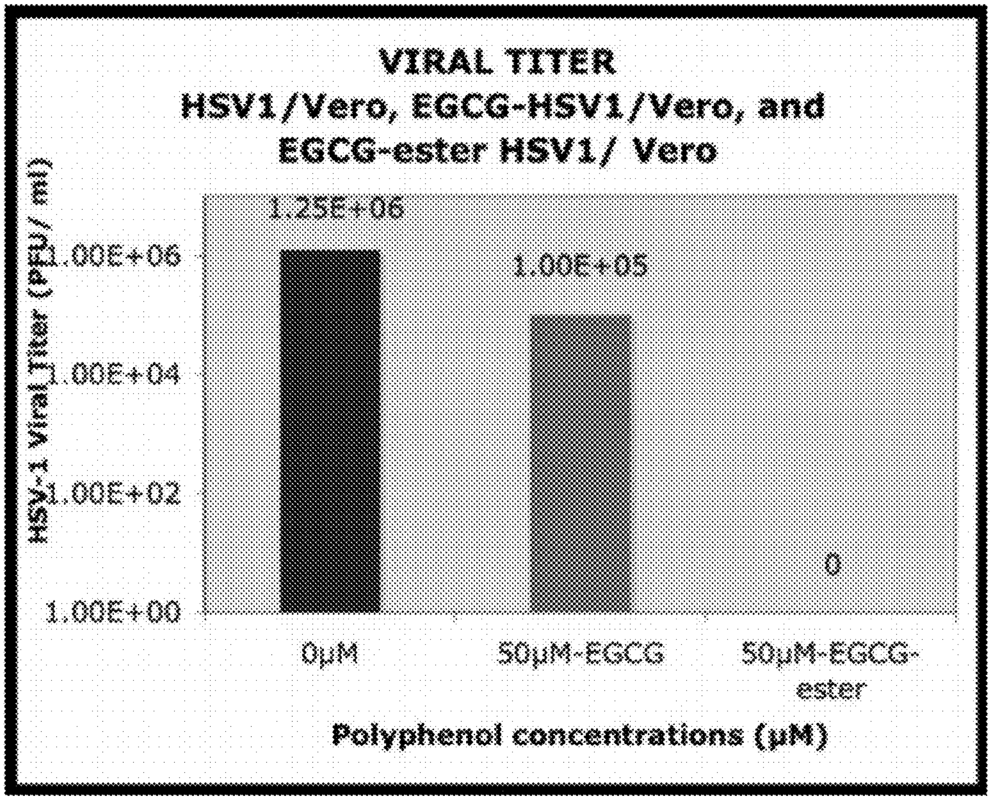
FIG. 3 is a bar graph of HSV-1 viral titer (PFU/ml) versus polyphenol concentrations (μM).

Viral titer was determined to study the effect of 50 μM of EGCG and EGCG-ester on the viral particle production by using plaque assay. Serial dilutions of viral lysates were performed from $10^{-1}$ to $10^{-7}$ and cells were then infected respectively with the dilutions. In the HSV1/Vero cells experiment, plaques were observed from $10^{-3}$ to $10^{-5}$ viral lysate dilution and the viral titer was $1.25\times10^6$ PFU/ml. In the 50 μM EGCG-HSV1/Vero cells experiment, plaques were only observed from $10^{-3}$ to $10^{-4}$, and the viral titer was $1\times10^5$ PFU/ml. Lastly, in the 50 μM EGCG-ester-HSV1/Vero cells experiment, there was no plaque formation seen in any of the viral lysate dilutions. The results are summarized in FIG. 3, which demonstrates, a 10-fold decrease when comparing HSV1/Vero titer to EGCG-HSV1/Vero titer. It also shows an even larger decrease in EGCG-ester HSV1/Vero titer compared to HSV1/Vero titer. This indicates that EGCG-ester is more potent in inhibiting HSV1 when compared to EGCG.

Figure 6:
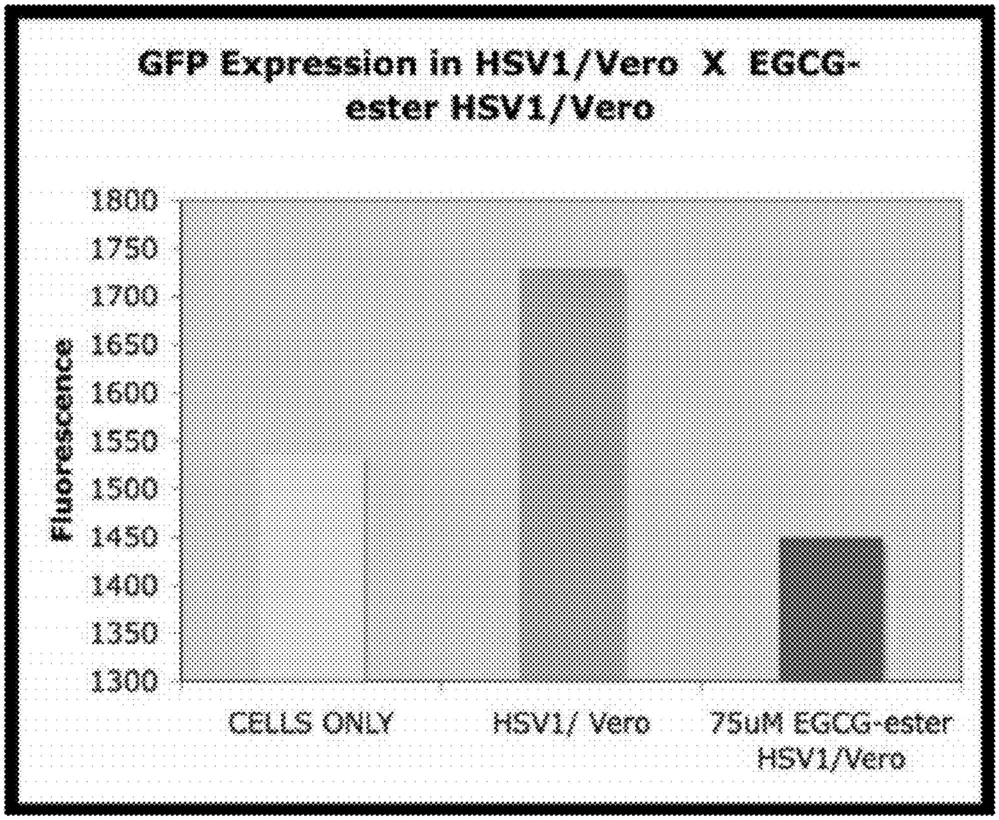
FIG. 6 is a bar graph of fluorescence versus cells only, HSV1/Vero or 75 μM EGCG-ester HSV1/Vero. GFP expression was measured.

In order to obtain the minimum inhibitory concentration of EGCG-ester on HSV1, different concentrations (12.5, 25, 50, 75 μM) of EGCG-ester were used at lower dilution of viral lysate ($10^{-1}$ and $10^{-2}$). The results indicated that as the concentration of EGCG-ester is increased, HSV1 titer is decreased. As seen in FIG. 6, at a concentration of 50 μM EGCG-ester and above, the HSV1 ability to form plaques is reduced by >99%.

The maximum nontoxic concentration was identified to be 75 μM for both EGCG and EGCG-ester and these concentrations were then used to study their effect on HSV1 viral production. In the plaque assay, the results showed that when the virus is previously treated with 50 μM EGCG, there is a 10-fold decrease in plaque formation. On the other hand, when HSV is treated with EGCG-ester at a concentration of 50 μM and above, there are no plaques observed. Different concentrations of EGCG-ester were then used to determine the minimum HSV1 inhibitory concentration. The results indicated that at a concentration of 50 μM and above, EGCG-ester completely inhibits PFU formation.

Example 6

Study of Green Fluorescence Protein Expression in HSV1/Vero Cells and EGCGester-HSV1/Vero Cells Materials and Methods

*Esherichia coli* Ampicillin-Resistant Plasmids with Green Fluorescent Protein (GFP)

An ampicillin-resistant strain of *Esherichia coli* was isolated froth a pure colony that was originally grown on Luria Broth (LB) in the presence of ampicillin and Larabinose. The colonies were transferred onto new LB that had been supplemented with 100 μl of ampicillin and 100 μl of L-arabinose prior to transferring the colonies. The concentration of ampicillin used was 100 ng/mL. The concentration of L-arabinose was created using serial dilutions and set in a 1:10 ratio to create a solution of 5% percent.

GFP Expression Study Using a Fluorometer

GFP expression was studied in *Escherichia coli* that contained GFP plasmid, and *Escherichia coli* without GFP plasmid. The fluorometer used was a Tuner Digital Fluorometer-Model 450. Samples were put into 3 mLs of $H_2O$ and serial dilutions were performed from the first 3 mLs of each sample. A standard dilution curve was obtained from the serial dilutions. Next, Vero cells were grown on T-75 flasks and allowed to reach confluence. HSV1 virions were treated for 3 hours with 75 μM of polyphenols prior to cell infection. Cells were then infected with treated and non-treated HSV1-UL46 and allowed to adsorb for 1 hour. Viruses that had not been absorbed were then removed by washing the cells twice with PBS. The cells were then incubated at 37° C. for 12 hrs. Cells were then trypsinized and pelleted. Finally, cells were resuspended with 3 mLs of $H_2O$ and analyzed for GFP expression using a fluorometer. 3 ml of water was used as the blank sample. The Gain knob was set to 1000 for higher fluorescence sensitivity.

GHSV-UL46

With a green fluorescence protein tagged HSV, it is possible to study the HSV viral life cycle, and study potential effects of lipophilic tea polyphenol on in vitro HSV infections (Willard, M. Journal of Virology. 2002; 10:5220-5232). If ester-modified EGCG is proven to have similar or better results against HSV infections, future animal and human studies can then be conducted toward a stable, and effective topical application to prevent human herpes simplex viral infection. Sexually transmitted HSV infects the host cell very quickly; therefore, an efficient antiviral drug needs to be made in order to inhibit HSV prior to the initial viral infection (Isaacs C E, et al. Antimicrobial Agents and Chemotherapy. 2008; 52(3):962-970).

Figure 7:
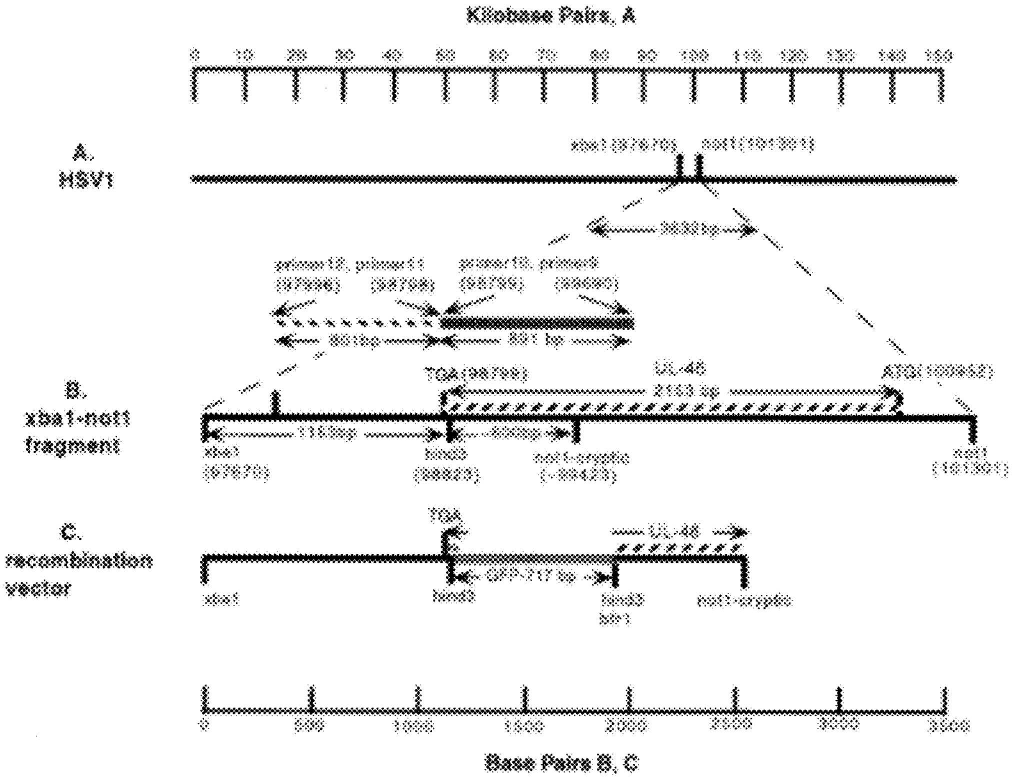
FIG. 7 is a schematic of the cloning strategy for introducing GFP to the gene UL46 of HSV 1.

A HSV 1 virus model has been modified by a team of researchers at Washington University School of Medicine. A green fluorescent protein was attached to the viral gene UL46 that encodes tegument protein VP 11/12. A schematic representation can be seen in FIG. 7. The GFP sequence was added to the UL46 gene by using homologous recombination vectors and primers designed to amplify the desired sequences (Willard, M. Journal of Virology. 2002; 10:5220-5232).

Cells Culture Maintenance

Vero cells were purchased from ATCC (Manassas, Va.) and were cultured in T25 flasks containing Dulbecco Minimal Essential Media (DMEM) with 5% Fetal Bovine Serum (FBS) and 1 ug/mL gentamycin at 37° C. and 5% $CO_2$ until confluent. Cell growth was carefully monitored using an ACCU-SCOPE phase contrast microscope with attached Micrometrics digital camera and Micrometric SE Premium software. To maintain the cultures, confluent monolayers of Vero cells were trypsinized with 500 μL of Trypsin/EDTA for 5 minutes. 4.5 mLs of media was then added to the T-25 flask and cells were subcultured into 6 well plates or other T-25 flasks and incubated until confluent.

HSV1-UL46 Virus Maintenance

HSV1-UL46 virus was purchased from ATCC (Manassas, Va.). Passage of virus was done in T-25 flasks and cells were allowed to reach complete cytopathic effect (CPE). The media was then collected into 15 mLs tornado tubes and it was centrifuged at 1000 rpm for 10 minutes to remove cellular debris. The supernatant containing virus was then kept under −80° C. until needed.

Results

Figure 5:
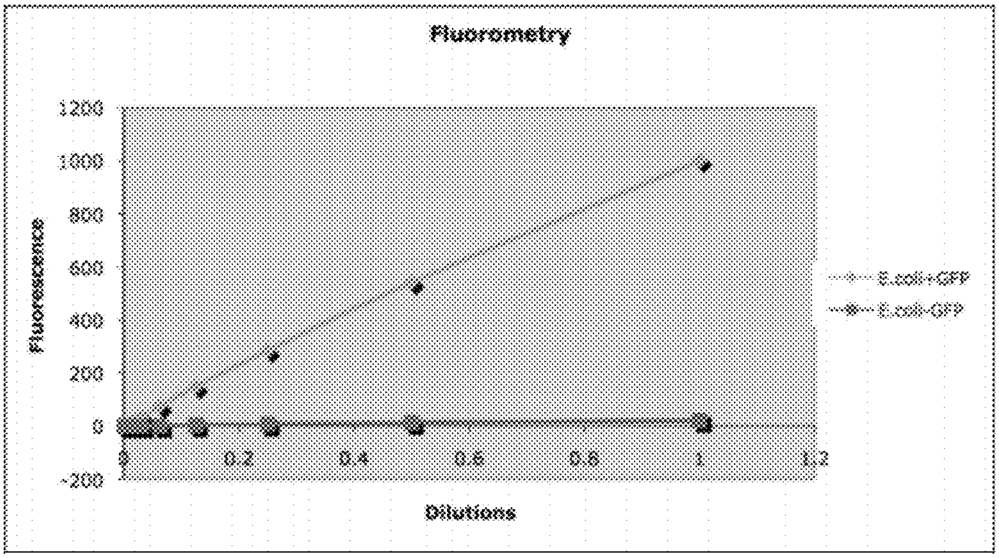
FIG. 5 is a line graph of fluorescence versus dilutions. The diamonds represent *E. coli*+GFP. The squares represent *E. coli*−GFP. The readings were taken on a Fluorometer.

The viral model system used in this study, HSV-GFPUL46, carries a green fluorescence protein (GFP) tag on the HSV1 UL46 gene. In this study, a fluorometer was used to measure the expression of green fluorescence protein in infected Vero cells. In order to quantitatively determine the GFP expression in cells, a standard dilution curve was generated with *Escherichia coli* (*E. coli*) containing a GFP insert. *Escherichia coli* with no GFP insert was also used as a negative control. Serial dilutions of *E. coli* cultures were prepared as described in the Materials and Methods section. The results are shown in table 4 and FIG. 5. As seen in the results, a linear dilution curve was successfully generated with serial diluted cultures of *E. coli* with GFP. The negative control shows very low readings. This experiment demonstrated that the use of the fluorometer is appropriate to provide a quantitative measure for GFP expression.

TABLE 4

Fluorometer data of GFP expression in *E. coli* with a GFP plasmid insert and *E. coli* with no GFP plasmid insert

| *Ecoli* + GFP | *Ecoli* − GFP | Dilutions |
|---|---|---|
| 1000 | 22 | 1/1 |
| 541 | 13 | 1/2 |
| 284 | 7 | 1/4 |
| 148 | 4 | 1/8 |
| 75 | 1 | 1/16 |
| 35 | 0 | 1/32 |
| 17 | 0 | 1/64 |
| 8 | 0 | 1/128 |
| 4 | 0 | 1/356 |
| 2 | 0 | 1/712 |

This experiment demonstrates that the fluorometer can be used to study and quantitatively measure GFP expression in both HSV1/Vero cells and EGCG-ester-HSV1/Vero cells. In this experiment, Vero cells only, HSV1/Vero cells, and 75 μM EGCG-ester-HSV1/Vero cells were used to quantitatively measure GFP expression. The results are shown in FIG. 6.

GFP expression is much lower in 75 μM-EGCG-ester HSV I/Vero cells compared to HSV1/Vero cells. Thus, expression of GFP as part of viral biosynthesis is decreased when HSV 1 is treated with EGCG-ester.

Example 7

Comparison of Amplicons of Glycoprotein D, GFP, and VP11/12 in HSV1/Vero Cells and EGCG-ester-HSV1/Vero Cells Using PCR-Based Assay Methods and Materials

TABLE 5

Primers used in PCR for analysis of HSV1/Vero cells DNA

| Primers | Nucleotide sequence (5' to 3') | Tm | amplicon |
|---|---|---|---|
| gD1 | F. AGACGTCCGGAAACAACCCTACAA (SEQ ID NO: 2)<br>R. ACACAATTCCGCAAATGACCAGGG (SEQ ID NO: 3) | 64.6<br>64.6 | 752 |
| gD2 | F. TTGTTTGTCGTCATAGTGGGCCTC (SEQ ID NO: 4)<br>R. TGGATCGACGGTATGTGCCAGTTT (SEQ ID NO: 5) | 64.6<br>64.6 | 938 |
| gB1 | F. AGATTCTGCGGTACTGCGATCACT (SEQ ID NO: 6)<br>R. ACGGAACACAAACAAGCACGGATG (SEQ ID NO: 7) | 64.6<br>64.6 | 986 |
| gB2 | F. AGCTGATTATCGCCACCACACTCT (SEQ ID NO: 8)<br>R. TGGCGTTGATCTTGTCGATCACCT (SEQ ID NO: 9) | 64.6<br>64.6 | 910 |
| gB3 | F. ATTCTCCTCCGACGCCATATCCACCTT (SEQ ID NO: 10)<br>R. AGAAAGCCCCCATTGGCCAGGTAGT (SEQ ID NO: 11) | 67.6<br>67.9 | 191 |
| GFP1 | F. GTCAAAGCTTAAGATGGTGAGCAAGG (SEQ ID NO: 12)<br>R. CTTGAAGCTTCTTGTACAGCTCGTCC (SEQ ID NO: 13) | 64.6<br>66.2 | 544 |
| GFP2 | F. TGACCCTGAAGTTCATCTGCACCA (SEQ ID NO: 14)<br>R. AACTCCAGCAGGACCATGTGAT (SEQ ID NO: 15) | 64.6<br>62.7 | 717 |
| VP11/12-1 | F. ACCAAGCCTTGATGCTCAACTCCA (SEQ ID NO: 16)<br>R. ACAACACGGITCCCGAGAG'TTTGA (SEQ ID NO: 17) | 64.6<br>64.6 | 957 |
| VP11/12-2 | F. ACCAAGCCTTGATGCTCAACTCCA (SEQ ID NO: 18)<br>R. ACACAACACGGTTCCCGAGAGTTT (SEQ ID NO: 19) | 64.6<br>64.6 | 959 |

The primer sets were used to prime DNA isolated from HSV1/Vero and EGCGester HSV1/Vero cells. The PCR product was analyzed using 1% gel electrophoresis. All the primers were able to prime the DNA samples and the amplicons have the expected sizes.

Sequencing of PCR Products

The PCR products for each primer set 1-9 have been sequenced and analyzed using NCBI homology search. The results suggested high homology to the reported HSV1 sequence. Tables 6-14 show the results from the Blast searches performed on each sequence. Therefore, the designed primers can be used to successfully study the molecular mechanisms of inhibition of EGCG-ester on HSV1/Vero cells. The sequences of the primers are as follows:

Glycoprotein D-Primer 1F-733 bps (SEQ ID NO: 22)

GTCATGCCATGCTCGGATGGGAGGCACTGTGCTATCCCCATCACGGTCAT
GGAGTACACCGAATGCTCCTACAACAAGTCTCTGGGGGCCTGTCCCATCC
GAACGCAGCCCCGCTGGAACTACTATGACAGCTTCAGCGCCGTCAGCGAG
GATAACCTGGGGTTCCTGATGCACGCCCCCGCGTTTGAGACCGCCGGCAC
GTACCTGCGGCTCGTGAAGATAAACGACTGGACGGAGATTACACAGTTTA
TCCTGGAGCACCGAGCCAAGGGCTCCTGTAAGTACGCCCTCCCGCTGCGC
ATCCCCCCGTCAGCCTGCCTCTCCCCCCAGGCCTACCAGCAGGGGGTGAC
GGTGGACAGCATCGGGATGCTGCCCCGCTTCATCCCCGAGAACCAGCGCA
CCGTCGCCGTATACAGCTTGAAGATCGCCGGGTGGCACGGGCCCAAGGCC
CCATACACGAGCACCCTGCTGCCCCCGGAGCTGTCCGAGACCCCCAACGC
CACGCAGCCAGAACTCGCCCCGGAAGACCCCGAGGATTCGGCCCTCTTGG
AGGACCCCGTGGGGACGGTGGCGCCGCAAATCCCACCAAACTGGCACATC
CCGTCGATCCAGGACGCCGCGACGCCTTACCATCCCCCGGCCACCCCGAA
CAACATGGGCCTGATCGCCGGCGCGGTGGGCGGCAGTCTCCTGGCAGCCC
TGGTCATTGGGGAAATTTTTTGTATATAAAAAAA

Glycoprotein D-Primer 2F -947 bps (SEQ ID NO: 23)

AGGCTGCGCGATATGCTTGGCGGATGCTCTCTCAGATGGCCGACCCCAAT
CGCTTTCGCGGCAAAGACCTTCCGGTCCTGGACCAGCTGACCGACCCTCC
GGGGGTCCGGCGCGTGTACCACATCCAGGCGGGCCTACCGGACCCGTTCC
AGCCCCCCAGCCTCCCGATCACGGTTTACTACGCCGTGTTGGAGCGCGCC
TGCCGCAGCGTGCTCCTAAACGCACCGTCGGGAGGCCCCCCCAGATTGTC
CGGCGGGGGCCCTCCGAAGGACGTTCCGGAAACAACCCTACAACCTGACC
ATCGCTTGGTTTCGGATGGGAGGCAACTGTGCTATCCCCATCACGGTCAT
GGAGTACACCGAAATGCTCCTACAACAAGTCTCTGGGGGCCTGTCCCATC
CGAAAACGGGCCCCGCGGGAAAAATAAAAAAAAAAATTTTCCGGGGCCGG
AGGAAAAAAAACCGGGGGTTTTATAAAGGGGGGGGGGTTGAAAAAATAC
GCCGGCACGTACCTGCGGTTCGTGGAAGATAAAAAGTGACGGAGATTAAT
TTTATTGGGCCGGCCGGGCCCGTAGTACGCCCTCCGCTGCGCATCCCCCC
CGTCAGCCTTGCCTCTCCCCCCCAGGCCTAACAGCAAGGGGGGTGAACGG
TGGGAACAGCAATCGGAATGGCTGGCCCCGCTTTCAATCCCCCGAGAAAA
CCAAGCCGCAACCGGTCGCCCGGTAATTACAGGCTTGGAAAGGATCGCCG
GGTAGACAACGGGGCCCCAAAGGCCCCATACAACGTAGTCACCCTTGGCT
TGCCGCCCGGAGCTGTTCCGAGAACTTCTCAATGGCTCACGCGCAGCCGG
GAAAGTTCGTCTCCGGCAAGAACACGAGAGAATTCGTCCCATCATTGGAA
GAGGCCTAGTGCGCTACGGTGTTGCGCGCTGTCATCATGATTATGTC

Glycoprotein B-Primer 1F-425 bps (SEQ ID NO: 24)

CAGGCATCACACCATCACAGACCATCATCGTAGAGTACCGCCGTCCCCCA
GCGTGCAGGCGGCGGCCGCGTGGTAGAGCAGGCGGGGGGGCGTGGAGCGT
GGCAGACCGCCATGGACGCGTGGACGCGCATCCGTGCGCGTTTTCCTCCA
TGTAGGGGAACCTGAAACTGGTAGCGGCCCGTAAGGCCGCCCGCCCAGGA

-continued

ACATGTGGGGGTTAAGCATAGCAAGTACTACGGCAGTGCCGGGTAACACC
GTGTGTTTCAGCGCGGCAACTGGCGCAGCCTTGTGGGTAGCAAACACGCC
GTGCCCGGCCTTTATTTTTGACGGACCCGGCAGATCGTTCAAGCCGGACG
CGGGCCGGGTTTAGTAGCGCGGCAGGGACCTCGGCGAGGAGACAGGAAGC
TCGCTATCAGACTATCCGGGTAATT

Glycoprotein B-Primer 2F-967 bps
(SEQ ID NO: 25)
TTCTCCTAACGGGTGCGCGGACTCGAGAGCGCCGCCCGGACTGCAGCCGC
CGACCTCCGAAGTCGTTACAGCAAGACGCGCGGCGAATATCTCACGTACG
ACTCCGACTGTCCGCTGTTGGCCATCGTCGAGAGCGCCCCCGACGGCTGT
ATCGGCCCCCGGTCGGTCGTGGTCTACGACCGCGAAGTTTTTCTCGATCC
TCTACTCGGTCCTCCAGCACCTCGCCCCCAGGCTACCTGACGGGGGTTAC
GACGGGCCCCGTAGCCCCGGCATTGCACAAGGCCCCCCCCTCGGGGGGGC
CGCCGGGGGTTCGCCGTTAGGGTCCCTTTGGGGGTGGAGGGGGGGGTTTG
GGTTTTTCGGGTTTTTTGCCCATTTTCCCGTTACGGCTTGGGGTTGGGGG
CGGCCCCAGGGGGGGGGAGGGGGGGGGATTGGAAATTCCGCCGGCCCCCC
CCCTTGTGGCCCCCCCCCAAGGGGGGGGGGCGGGAAGGGGAAAAAAAAAA
AAAAACCAAAAAAACCCGGGGCCCCCCCCCCCCCCACCCGAAAAAAGCCA
AATTGGTGGAGGGGGGGGGGCCCCCCTGGGGGGGGACCCCGTGGGGGAAA
TTGGGGGGTAAAAAAACCCCTTTTATTTTCTTGGGGGGGGCCCCCCCCCC
AGGGGGCCTGGGGGGTCCAATTTAAGAAACCCACAAAATTTTCCGTACCG
GCCCAAGGATACAAAAATTTACCGAGGACCCCCGGGGGGGTTTTTTTAGA
AAAAAAACCCCCCCCCAAAAAATTTCGAGGGCCCAAAGTGTAAAAAAAAA
ACGCCCTGCCGTTTTTTACAGAATATTTTTCTTTGCCGAAACCTTAACTC
CTCCAATTTTTAAGGGGAGATTTTTTTAAAGACACGCCCCCTCTCTTCCT
TTTTTCGAGGAGGGGGTAAATAGAACATAAGTATCGCGCCCATAAAAAAA
AAGATAGAATAAAAAGG Glycoprotein B-Primer 3F-156 bps
(SEQ ID NO: 26)
CCACCAGACCGAGTACCCGCTCTCGCGCGTGACCTGGGGGACTGCATCGG
CAAGGACGCCCGCGACGCCATGGACCGCATCTTCGCCCGCAGGTACAACG
CGACGCACATCAAGGTGGGCCAGCCGCAGTACTACCTGGCCAATGGGGGC
TTTCTT GFP-Primer 1F-714 bps
(SEQ ID NO: 27)
GAGGCCGGATCACGGGTGTGCCATCCTGGTCGAGCTGGACGGCGACGTAA
CGGCCACAAGTTCAGCGTGTCCGGCGAGGGCGAGGGCGATGCCACCTACG
GCAAGCTGACCCTGAAGTTCATCTGCACCACCGGCAAGCTGCCCGTGCCC
TGGCCCACCCTCGTGACCACCCTGACCTACGGCGTGCAGTGCTTCAGCCG
CTACCCCGACCACATGAAGCAGCACGACTTCTTCAAGTCCGCCATGCCCG
AAGGCTACGTCCAGGAGCGCACCATCTTCTTCAAGGACGACGGCAACTAC
AAGACCCGCGCCGAGGTGAAGTTCGAGGGCGACACCCTGGTGAACCGCAT
CGAGCTGAAGGGCATCGACTTCAAGGAGGACGGCAACATCCTGGGGCACA -continued AGCTGGAGTACAACTACAACAGCCACAACGTCTATATCATGGCCGACAAG
CAGAAGAACGGCATCAAGGTGAACTTCAAGATCCGCCACAACATCGAGGA
CGGCAGCGTGCAGCTCGCCGACCACTACCAGCAGAACACCCCCATCGGCG
ACGGCCCCGTGCTGCTGCCCGACAACCACTACCTGAGCACCCAGTCCGCC
CTGAGCAAAGACCCCAACGAGAAGCGCGATCACATGGTCCTGCTGGAGTT
CGTGACCGCCGCCGGGATCACTCTCGGCATGGACGAGCTGTACTGAAAAC
TCTCTTTGAGGAAA GFP-Primer 2F-513 bps
(SEQ ID NO: 28)
CGCCGCCGTCCTGGCCCACCCTCGTGACCACCCTGACCTACGGCGTGCAG
TGCTTCAGCCGCTACCCCGACCACAAGAAGCAGCACGACTTCTTCAAGTC
CGCCATGCCCGAAGGCTACGTCCAGGAGCGCACCATCTTCTTCAAGGACG
ACGGCAACTACAAGACCCGCGCCGAGGTGAAGTTCGAGGGCGACACCCTG
GTGAACCGCATCGAGCTGAAGGGCATCGACTTCAAGGAGGACGGCAACAT
CCTGGGGCACAAGCTGGAGTACAACTACAACAGCCACAACGTCTATATCA
TGGCCGACAAGCAGAAGAACGGCATCAAGGTGAACTTCAAGATCCGCCAC
AACATCGAGGACGGCAGCGTGCAGCTCGCCGACCACTACCAGCAGAACAC
CCCCATCGGCGACGGCCCCGTGCTGCTGCCCGACAACCACTACCTGAGCA
CCCAGTCCGCCCTGAGCAAAGACCCCAACGAGAAGCGCGATCACATGGTC
TGCCGGGAGTTAA VP11/12-Primer 1-964 bps
(SEQ ID NO: 29)
TCCGCGTGGGGGCGTCATCGTGGGGACAGGGGGGCGGTGGTCCGACAGAA
CGCTCCTGGCTGTCCACCGCGGCCCGCAGATACTCGTTGTTCAGGCTGTC
GGTGGCCCAGACGCCGTACCCGGTGAGGGTCGCGTTGATGATATACTGGG
CGTGGTGATGGACGATCGACAGAACCTCCACCGTGGATACCACGGTATCC
ACGGTCCCGTACGTACCGCCGCTCCGCTTGCCGGTCTGCCACAGGTTGGC
TAGGCACGTCAGGTGGCCCAGGACGTCGCTGACCGCCGCCCTGAGCGCCA
TGCACTGCATGGAGCCGGTCGTGCCGCTGGAACCCCGGTCCAAATGGCGC
GCGAACGTTTCCGCGGGCCCCTTCCGGGCTGCCGCCGAAGCGGAAGGAAC
CGGGCAATTGGAGGGACTCAGCCGGTGACATACGTGCTTGTCCGTCGTCA
ACGGCATCCAGGAGGCCCACCGGTACAGCACGGAAACGTAGGCCAGGAGC
TCCGTTAAGCCGCATTGCGGTGTCGGTCCTGGGACGTTTTGGGCCCCCCG
GGGCGCATAAGGAACATGTACTGCTGAATCCAATGGAGGGGCGTCGCGCA
GCCGGCCCACGGTGGCGGCTTATTTGGGCCCCCGCGCCCCCGCCTTTTAA
ACGGGGTGCCGCGCCAAGCCACTTTTGGGGCCGGGTTGGCCCGCAACAAC
CACGTGAAAGGCTGGGGCTCCGCAGTCGCCCACGGGGTCCTTCGGGAAAC
GTCAAGGCCGGCTGGGCCACAACCGTCTGCAGGTACTTCAAGTACTGCGT
GGAGGATGGCGCGCTCAAACTGGGCCGCTCTGGTCAGCTCCACCTTCGCC
CAGCGCTGGGTGTCGGTCTGAAGCGTACTGCCGGATGTACTCGTTAGTGC
AGGTCGCTTGGCGAGCCCGTCACGATCTAGACTATCGTGGGGAGAGAGTG
TGTAGTATATATAA -continued VP11/12-Primer 2-964 bps (SEQ ID NO: 30)

```
TTCAGCTGGGGGCGTCATCGTGCGGACAGGGGGGCGGTGGTCCGACAGAA
ACGCTCCTGGCTGTCCACCGCGGCCCGCAGATACTCGTTGTTCAGGCTGT
CGGTGGCCCAGACGCCGTACCCGGTGAGGGTCGCGTTGATGATATACTGG
GCGTGGTGATGGACGATCGACAGAACCTCCACCGTGGATACCACGGTATC
CACGGTCCCGTACGTACCGCCGCTCCGCTTGCCGGTCTGCCACAGGTTGG
CTAGGCACGTCAGGTGGCCCAGGACGTCGCTGACCGCCGCCCTGAGCGCC
ATGCACTGCATGGAGCCGGTCGTGCCGCTGGGACCCCGGTCCAGATGGGG
GCGCGAACGTTTCCGGGGGGCCCCTCCGGCCTGCCGCCGAGCGGAAGGAA
CCGGGCAATTGGAGGGACTCAGCCGGGGACATACGTGCTTTGTCCGTCGT
CCACAGCATCAGGGACGCCCACGGTTACAGCACGGAAACGTAGCCCAGGA
CCTCTTTGACCCGCAGTGCGGTTTCGGTCCTGGGGCGACTTGGTCCCCCC
GGGCCCCATAAGGAACATGTACTGCTGAATCCAATGGAAGGGCGTCGGCC
AGCCCGGCCAGGGTGGCGGCTAATTTGGGCCGCCGGCGCCCCCGCTTTTG
AACGGGGGTGCGCGCCAGCGTTTTTGGGGCCGGGGGTGGGCCCGCGCCAC
CACGTGAAGGCCGGGGTCCGCAGTCCCCCCACGGGGTCTTGGGGAATGTC
AGGGCGGTGGGAACCACCGTTCGGCGGTACTTTCCGGAACGGGCGTGAAG
GATGGCGCGGCTCAAACTGGACCGCGGGGCAGTCTCCACTTTCGCCCAAG
CGCCTGGGTGTGCGGCCGAAAGCATATGCCGGAATGTACTCGTAGTGACG
GTTCGCTGGCGAGCCGGTCACGATCAATCTCTCGGAGACGTGGTGTGATA
GTATATAA
```

Polymerase Chain Reaction

Nine sets of primers were designed to prime different regions of the HSV1 genome based on published sequences. Two sets of primers were designed to target HSV I glycoprotein D. These include 5'-AGACGTCCGGAAACAACCCTACAA-3' (SEQ ID NO:2) for the forward and 5'-ACACAATTCCGCAAATGACCAGGG-3' (SEQ ID NO:3) for the reverse. The second set includes 5'-TTGTTTGTCGTCATAGTGGGCCTC-3' (SEQ ID NO:4) for the forward and 5'TGGATCGACGGTATGTGCCAGTTT-3' (SEQ ID NO:5) for the reverse. Next, two sets of primers were designed to target HSV1 glycoprotein B. They are the following: 5'AGATTCTGCGGTACTGCGATCACT-3' (SEQ ID NO:6) for the forward and 5'-ACGGAACACAAACAAGCACGGATG-3' (SEQ ID NO:7) for the reverse. The second set includes 5'-AGCTGATTATCGCCACCACACTCT-3'(SEQ ID NO:8) for the forward and 5'-TGGCGTTGATCTTGTCGATCACCT-3' (SEQ ID NO:9) for the reverse. A third set of primers had been previously designed and published on the book *Herpes Simplex Virus Protocols* by S. Moira Brown and Alasdair R. MacLean. The set includes 5'ATTCTCCTCCGACGCCATATCCACCTT-3' (SEQ ID NO:10) for the forward and 5'-AGAAAGCCCCCATTGGCCAGGTAGT-3' (SEQ ID NO:11) for the reverse. A set of primers was designed to target the Green Fluorescent protein attached to the UL46 gene of HSV 1. It includes 5'-GACCCTGAAGTTCATCTGCACCA-3' (SEQ ID NO:14) for the forward and 5'-AACTCCAGCAGGACCATGTGAT-3' (SEQ ID NO:15) for the reverse. A second set of primers designed for the GFP had been previously designed 42. It includes 5'-GTCAAAGCTTAAGATGGTGAGCAAGG-3' (SEQ ID NO:12) for the forward and 5'-CTTGAAGCTTCTTGTACAGCTCGTCC-3' (SEQ ID NO:13) for the reverse. Finally, two sets of primers were designed to target HSV1 tegument protein VP11/12 that corresponds to the UL46 gene. They are the following: 5'-ACCAAGCCTTGATGCTCAACTCCA-3' (SEQ ID NO:16) for the forward and 5'-ACAACACGGTTCCCGAGAGTTTGA-3' (SEQ ID NO:17) for the reverse. The second set includes 5'-ACCAAGCCTTGATGCTCAACTCCA-3' (SEQ ID NO:18) for the forward and 5'ACACAACACGUTTCCCGAGAGTTT-3' (SEQ ID NO:19) for the reverse. The reaction mix included 1 μL of the extracted DNA, 1 μL of forward and 1 μL of reverse primers, 12.5 μL of Master Mix, and 9.5 μL of diH2O. The mix was put into PCR tubes and placed into a Labnet MultiGene II thermal cycler (Labnet International, Edison N.J.). The reaction profile was initial denaturation at 95° C. for 2 minutes followed by cycles of denaturation at 95° C. for 30 seconds, annealing at 60° C. for 1 minute and extension at 72° C. for 30 seconds. The last step included a final extension period at 72° C. for 10 minutes. Once the cycle was over, samples were cooled down to 4° and then stored at −20° C. freezer for future analysis via agarose gel electrophoresis.

Analysis of PCR Products

Polymerase chain reaction products were analyzed and visualized on 1% agarose gels. Each gel was made by weighing 0.5 g of agarose (USB Corporation, Cat No 32802) and combining it with 50 mLs of 1×TAE (Tris-Acetate-EDTA) buffer. The mixture was heated for 1 minute in a microwave until the agarose completely dissolved. The mixture was then poured into a gel rig and allowed to solidify. A gel comb was used on one end of the gel in order to produce the wells. Once the gel had solidified samples were loaded into each well (2 μL of 10X loading dye with 10 μL of PCR product). A Hi-Lo DNA marker was loaded into the first well. The gel was run at 115V for 1 hour. The gel was then stained with Ethidium Bromide for 15 minutes and washed with water for another 15 minutes. The gel was then analyzed under UV light using Kodak Image Station 440 CF (Perkin Elmer Life Sciences, Waltham, Mass.).

Real Time Polymerase Chain Reaction

A set of primer that primes HSV1 glycoprotein D was designed for use in Real time polymerase chain reaction. This set includes 5"-CAACCCTACAACCTGACCATC-3' (SEQ ID NO:20) for the forward and 5'TGTAGGAGCATTCGGTGTAC-3' (SEQ ID NO:21) for the reverse. Each tube (except the negative controls-no DNA) contained 104 of Fast SYBR green master mix (ABI Fast SYBR Green Master Mix), 1 μL of forward primer, 1 μL of reverse primer, 14 of genomic DNA and 6 μL of Di 1-120. The samples were run on an ABI StepOnePlus Real-Time PCR System. The Run methods were: a holding stage at 95° C. for 5 minutes followed by 40 cycles of denaturation at 95° C. for 1 minute, annealing at 60° C. for 1 minute and extension at 72° C. for 30 seconds. Next, the melting curve stage included 95° C. for 15 seconds, followed by 60° C. for 1 minute, and 95° C. for 15 seconds.

DNA Extraction from HSV1 Infected Cells

Cells were grown on 60 mm plates and allowed to reach confluency. Cells were then infected with HSV I treated and HSV1 non-treated for 1 hour at 37° C. and 5% $CO_2$. After absorption time, cells were washed with PBS and media was added to the plates. After 12 hours, cells were trypsinized and DNA was extracted using the DNeasy Blood and Tissue Handbook (Qiagen 2006). DNA concentration was then measured by using a Nanodrop Specrophotometer.

TABLE 6

Blast search results for retrieved sequence of Glycoprotein D Primer 1F
Sequences producing significant alignments:

| Accession | Description | Max score | Total Score | Query coverage | E value | Max ident |
|---|---|---|---|---|---|---|
| gi\|22831528\|EF177451.1 | Human herpesvirus 1 strain gC-39-R6 glycoprotein D | 1252 | 1252 | 96% | 0.0 | 99% |
| gil\|21277018\|EF157321.1 | Human herpesvirus 1 strain KOSc(AC4) glycoprotein D | 1252 | 1252 | 96% | 0.0 | 99% |
| gi\|121276 | Human herpesvirus 1 strain KOSc(AC3, AC6) glycoprotein D | 1252 | 1252 | 96% | 0.0 | 99% |
| gi\|12127698\|EF157319.1 | Human herpesvirus 1 strain KOSc glycoprotein D | 1252 | 1252 | 96% | 0.0 | 99% |
| gi\|330193\|L09244.1 | Herpes simplex virus type 1 glycoprotein D gene | 1252 | 1252 | 96% | 0.0 | 99% |

TABLE 7

Blast search results for retrieved sequence of Glycoprotein D Primer 2F
Sequences producing significant alignments:

| Accession | Description | Max score | Total Score | Query coverage | E value | Max ident |
|---|---|---|---|---|---|---|
| gi\|121277035\|EF157322.1 | Human herpesvirus 1 strain KOSc(C2) glycoprotein D (US6) | 744 | 744 | 85% | 0.0 | 83% |
| gi\|121276981\|EF157319.1 | Human herpesvirus 1 strain KOSc glycoprotein D (US6) | 744 | 744 | 85% | 0.0 | 83% |
| gi\|330100\|J02217.1 | HSV1 glycoprotein D | 744 | 744 | 85% | 0.0 | 83% |
| gi\|330066\|L09243.1 | Herpes simplex virus type 1 glycoprotein D | 744 | 744 | 85% | 0.0 | 83% |

TABLE 8

Blast search results for retrieved sequence of Glycoprotein B Primer 1F.

| Accession | Description | Max score | Total Score | Query coverage | E value | Max ident |
|---|---|---|---|---|---|---|
| gi\|330109\|M21629.1 | Herpes simplex virus type 1 glycoprotein B gene (gB-1), | 223 | 223 | 94% | 1e−54 | 75% |
| gi\|6572414\|Z86099.2 | Herpes simplex virus type 2 (strain HG52), | 149 | 149 | 85% | 2e−32 | 72% |

TABLE 9

Blast search results for retrieved sequence of Glycoprotein B Primer 2F.
Sequences producing significant alignments:

| Accession | Description | Max score | Total Score | Query coverage | E value | Max ident |
|---|---|---|---|---|---|---|
| gi\|330082\|KO1760.1 | HSV1 (KOS) glycoprotein B gene, complete cds | 407 | 407 | 35% | 1e−109 | 88% |
| gil\|14318788\|DQ889502.1 | Human herpesvirus 1 strain HF clone 10, partial sequence | 398 | 398 | 35% | 5e−107 | 87% |
| gi\|60416\|Y00453.1 | Herpes simplex virus type 1 late gene ICP 18.5 | 398 | 398 | 31% | 5e−107 | 90% |
| gi\|290766081\|GU734772.1 | Human herpesvirus 1 strain H129, complete genome | 394 | 394 | 35% | 6e−106 | 87% |
| gi\|222478328\|FJ593289.1 | Human herpesvirus 1 transgenic strain 17, complete genome | 394 | 394 | 35% | 6e−106 | 87% |
| gi\|1944536\|X14112.1 | Human herpesvirus 1 complete genome | 394 | 394 | 35% | 6e−106 | 87% |
| gi\|290766003\|GU734771.1 | Human herpesvirus 1 strain F, complete genome | 389 | 389 | 35% | 3e−104 | 86% |
| gi\|330089\|K03541.1 | HSV-1 (Patton) glycoprotein B Gene, complete cds | 389 | 389 | 35% | 3e−104 | 86% |

TABLE 10

Blast search results for retrieved sequence of Glycoprotein B Primer 3F.

| Accession | Description | Max score | Total Score | Query coverage | E value | Max ident |
|---|---|---|---|---|---|---|
| gi\|7839508\|AF259899.1 | Human herpesvirus 1 glycoprotien B (UL27) gene | 266 | 266 | 98% | 3e−68 | 98% |
| gi\|330109\|M21629.1 | Herpes simplex virus type 1 glycoprotien B gene (gB-1) | 266 | 266 | 98% | 3e−68 | 98% |
| gi\|330089\|K03541.1 | HSV-1 (Patton) glycoprotien B gene, complete cds | 266 | 266 | 98% | 3e−68 | 98% |
| gi\|330087\|K02720.1 | HSV-1 (mutant strain tsB5), glycoprotien B (gB) gene | 266 | 266 | 98% | 3e−68 | 98% |

TABLE 11

| Blast search results for retrieved sequence of GFP Primer 1F Sequences producing significant alignments: | | | | | | |
|---|---|---|---|---|---|---|
| Accession | Description | Max score | Total Score | Query coverage | E value | Max ident |
| gi\|193884059\|AB375115.1 | Cloning vector pInSRT-GFPhFDC.SP DNA, complete sequence | 1209 | 1209 | 94% | 0.0 | 99% |
| gi\|328672377\|HM367072.1 | Synthetic construct ArchT-GFP gene, complete cds | 1207 | 1207 | 94% | 0.0 | 99% |

TABLE 12

| Blast search results for retrieved sequence of GFP Primer 2F. Sequences producing significant alignments: | | | | | | |
|---|---|---|---|---|---|---|
| Accession | Description | Max score | Total Score | Query coverage | E value | Max ident |
| gi\|328672377\|HM367072.1 | Synthetic construct ArchT-GFP gene, complete cds | 883 | 883 | 97% | 0.0 | 99% |
| gi\|327360350\|FR846927.1 | Synthetic construct for ACTA2-BKbeta1-E gene | 883 | 883 | 97% | 0.0 | 99% |
| gi\|326910732\|JF275063.1 | Synthetic construct plasmid pBIT GST/EGFP fusion protein | 883 | 883 | 97% | 0.0 | 99% |
| gi\|325699378\|HQ895843.1 | Cloning vector pGEM/hM33_UL33-GFP, complete sequence | 883 | 883 | 97% | 0.0 | 99% |

TABLE 13

| Blast search results for retrieved sequence of VP11/12 Primer 1F. Sequences producing significant alignments: | | | | | | |
|---|---|---|---|---|---|---|
| Accession | Description | Max score | Total Score | Query coverage | E value | Max ident |
| gi\|222478328\|FJ593289.1 | Human herpesvirus 1 transgenic strain 17, complete genome | 1180 | 1180 | 96% | 0.0 | 90% |
| gi\|1944536\|X14112.1 | Human herpesvirus 1 complete genome | 1180 | 1180 | 96% | 0.0 | 90% |
| gi\|290766081\|GU734772.1 | Human herpesvirus 1 strain H129, complete genome | 1177 | 1177 | 96% | 0.0 | 90% |
| gi\|29076603\|GU734771.1 | Human herpesvirus 1 strain F, complete genome | 1177 | 1177 | 96% | 0.0 | 90% |
| gi\|330056\|M15621.1 | HSV1 (strain F) alpha-trans-inducing factor genes, complete | 1177 | 1177 | 96% | 0.0 | 90% |
| gi\|114318788\|DQ889502.1 | Human herpesvirus 1 strain HF clone 10, partial sequence | 1171 | 1171 | 96% | 0.0 | 90% |
| gi\|154744672\|EU029143.1 | Human herpesvirus 2 isolate subject ID VRC9154 specimen | 776 | 776 | 96% | 0.0 | 81% |
| gi\|154744670\|EU029142.1 | Human herpesvirus 2 isolate subject ID GW13901 specimen | 776 | 776 | 96% | 0.0 | 81% |
| gi\|154744668\|EU029141.1 | Human herpesvirus 2 isolate subject ID GW 20219 specimen | 776 | 776 | 96% | 0.0 | 81% |
| gi\|154744666\|EU029140.1 | Human herpesvirus 2 isolate subject ID VRC8339 specimen | 776 | 776 | 96% | 0.0 | 81% |
| gi\|154744664\|EU029139.1 | Human herpesvirus 2 isolate subject ID GW9821 specimen | 776 | 776 | 96% | 0.0 | 81% |
| gi\|154744662\|EU029138.1 | Human herpesvirus 2 isolate subject ID GW4317 specimen | 776 | 776 | 96% | 0.0 | 81% |
| gi\|154744660\|EU029137.1 | Human herpesvirus 2 isolate subject ID VRC11098 | 776 | 776 | 96% | 0.0 | 81% |
| gi\|161789583\|EU281624.1 | Human herpesvirus 2 strain 186 UL46 gene | 773 | 773 | 96% | 0.0 | 81% |

TABLE 14

| Blast search results for retrieved sequence of VP11/12 Primer 2F. Sequences producing significant alignments: | | | | | | |
|---|---|---|---|---|---|---|
| Accession | Description | Max score | Total Score | Query coverage | E value | Max ident |
| gi\|222478328\|FJ593289.1 | Human herpesvirus 1 transgenic strain 17, complete genome | 1144 | 1144 | 98% | 0.0 | 89% |
| gi\|1944536\|X14112.1 | Human herpesvirus 1 complete genome | 1144 | 1144 | 98% | 0.0 | 89% |
| gi\|290766081\|GU734772.1 | Human herpesvirus 1 strain H129, complete genome | 1139 | 1139 | 98% | 0.0 | 89% |
| gi\|114318788\|DQ889502.1 | Human herpesvirus 1 strain HF clone 10, partial sequence | 1135 | 1135 | 98% | 0.0 | 89% |
| gi\|290766003\|GU734771.1 | Human herpesvirus 1 strain F, complete genome | 1130 | 1130 | 98% | 0.0 | 88% |
| gi\|330056\|M15621.1 | HSV1 (strain F) alpha-trans-inducing factor genes, complete | 1130 | 1130 | 98% | 0.0 | 88% |
| gi\|154744674\|EU029144.1 | Human herpesvirus 2 isolate subject ID VRC7494 specimen | 728 | 728 | 99% | 0.0 | 79% |
| gi\|154744672\|EU029143.1 | Human herpesvirus 2 isolate subject ID VRC9154 specimen | 728 | 728 | 99% | 0.0 | 79% |
| gi\|154744670\|EU029142.1 | Human herpesvirus 2 isolate subject ID GW13893 specimen | 728 | 728 | 99% | 0.0 | 79% |
| gi\|154744668\|EU029141.1 | Human herpesvirus 2 isolate subject ID GW20219 specimen | 728 | 728 | 99% | 0.00 | 79% |
| gi\|154744666\|EU029140.1 | Human herpesvirus 2 isolate subject ID VRC8339 | 728 | 728 | 99% | 0.0 | 79% |
| gi\|154744664\|EU029139.1 | Human herpesvirus 2 isolate subject ID GW9821 | 728 | 728 | 99% | 0.00 | 79% |
| gi\|154744662\|EU029138.1 | Human herpesvirus 2 isolate subject ID GW4317 | 728 | 728 | 99% | 0.0 | 79% |
| gi\|154744660\|EU029137.1 | Human herpesvirus 2 isolate subject ID VRC 11098 | 728 | 729 | 99% | 0.0 | 79% |
| gi\|161789583\|EU281624.1 | Human herpesvirus 2 strain 186 UL46 (UL46) gene, complete | 724 | 724 | 99% | 0.0 | 79% |

Results

DNA extracted from HSV1/Vero cells and EGCG-ester HSV1/Vero cells was purified and isolated and the amount and purity was determined by Nanodrop spectrophotometer ND1000. The control sample contained 566.4 ng/μL, the 75 μM EGCG-ester sample contained 560.1 ng/μL, and the cells only sample contained 562.8 ng/μL. Since the concentration of DNA in each sample is similar in quantity, 1 μL was used from each sample with constant amount of primer for glycoprotein D to do a comparatively PCR-based assay. By using a Kodak Image analyzer 440CF, the band intensity of each experiment was measured. The readings of the control band were 445.92, 588.24, and 541.73 with an average of 525.29. The readings for the 75 μM EGCG-ester band were 353.87, 438.47, and 407.82 with an average of 400.05. 75 μM EGCG-ester HSV1/Vero intensity of PCR product was less than the intensity of HSV1/vero cells.

Further experiment was carried out using primers for glycoprotein D, GFP and VP11/12 to perform PCR-based assay. The results demonstrate that when HSV1 is treated with 75 μM EGCG, the DNA band intensity is decreased. When HSV 1 is treated with 75 μM EGCG-ester the DNA band intensity is further decreased. This implies that fewer HSV1 particles were able to infect Vero cells when treated with EGCG and even more when treated with EGCG-ester as compared to Vero cells infected with HSV1 only. However, in order to have a quantitative measure, further analyses needed to be carried out by using Real Time PCR.

Figure 8:
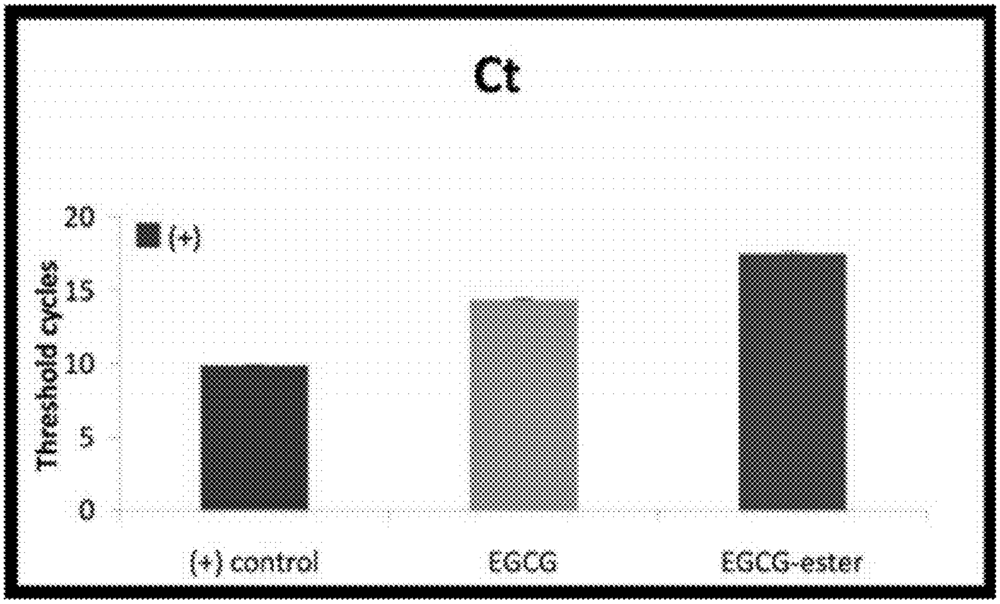
FIG. 8 is a bar graph of threshold cycles versus control, EGCG and EGCG-ester. The graph provides Real Time PCR data of HSV1 Glycoprotein D.
Figure 9:
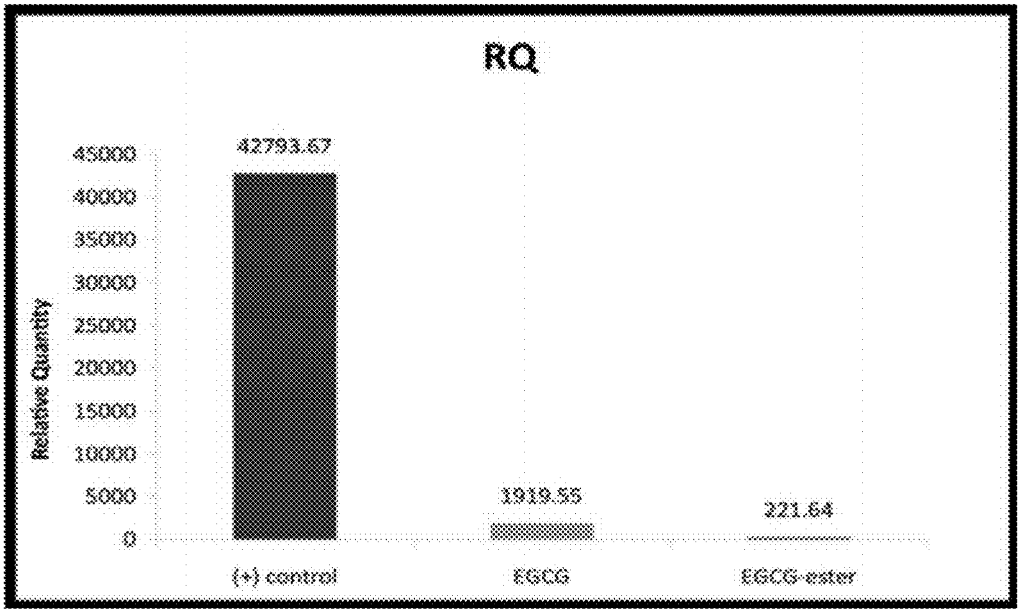
FIG. 9 is a bar graph of relative quantity versus control, EGCG and EGCG-ester. The data shows the HSV1 Glycoprotein D amplification in HSV1/Vero, EGCG-HSV1/Vero and EGCG-ester-HSV1/Vero Cells.

Previous experiments indicated that the amplification of Glycoprotein D is less in EGCG-ester-HSV1/Vero cells compared to HSV1/Vero cells, therefore it is important to carry out quantitative study of Glycoprotein by using Real time PCR. Special primers were designed for this study as shown in table 15. The process of real time PCR works by collecting fluorescence data at the end of each cycle of the reaction. The SYBR green dye used in the experiment binds to the double stranded PCR product causing the PCR product to fluoresce. As the reaction continues the instrument recalls the threshold for each sample. The threshold cycle (Ct) is the critical cycle at which the first significance increase in fluorescence is detected. Once the PCR cycles ended, the data were collected and the Ct values for each of the samples were analyzed and the relative quantity (RQ) of fluorescence was reported. The standard for comparing Ct values is that a difference in one Ct is equivalent to a two-fold difference in the amount of DNA. 100 ng/4 of DNA was used for all samples; cells only, HSV1/Vero, and EGCG-ester HSV1/Vero. The results are shown in FIGS. 8 and 9.

TABLE 15

Real time PCR primers for priming Glycoprotein D on HSV1

| Primers | Nucleotide sequence (5' to 3') | Tm | Amplicon |
|---|---|---|---|
| gD1 | F. CAACCCTACAACCTGACCATC (SEQ ID NO: 20) | 62.6 | 100 bps |
| | R. TTGTAGGAGCATTCGGTGTAC (SEQ ID NO: 21) | 60.6 | 100 bps |

Figure 10:
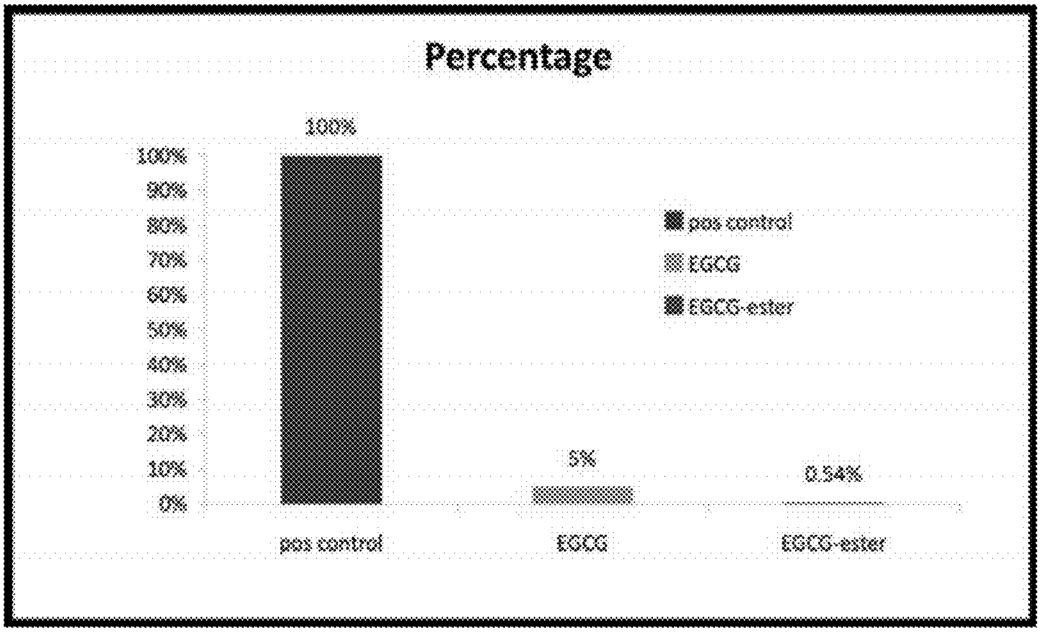
FIG. 10 is a bar graph of the percentage versus positive control, EGCG and EGCG-ester.
Figure 11:
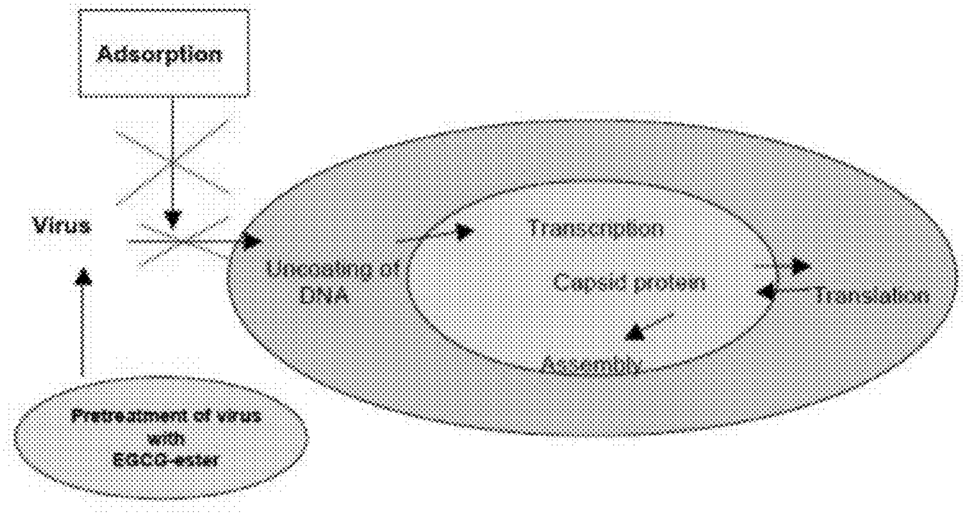
FIG. 11 is a schematic representation of possible mode of action of EGCG-ester on HSV1.

The results show a 32-fold difference in the amount of glycoprotein D of EGCGHSV1/Vero to HSV1/Vero and a 256-fold difference from HSV1/vero to EGCG-ester HSV1/Vero. The results indicate that EGCG inhibits HSV1 95% and EGCG-ester inhibits HSV1 99.46% (FIG. 10). Its mode of action seems to be by interfering with the virion envelope glycoproteins or by interfering with viral compounds for viral adsorption and cell entry (Song et al. Antivirus Response 68:66-74, 2005; Williamson et al. J. of Allergy Clinical Immunology 118:1369-1374, 2006). Apparently, inhibition appears to occur during adsorption but not after penetration of the virus (FIG. 11). By using a green fluorescent protein tag, it was confirmed that GFP expression is greatly decreased in treated virus compared to control virus.

The PCR based DNA assay of glycoprotein D of HSV1/Vero showed higher band intensity as compared to EGCG-ester-HSV1/Vero cells. This infers that there was more viral DNA in the cells infected with HSV1/Vero as compared to 75 μM EGCGester-HSV1/Vero.

Also, the real time PCR-based assay indicated that there is a 32-fold difference in the amount of DNA of glycoprotein D in EGCG-HSV1/Vero cells compared to the DNA of HSV1/Vero cells and a 256-fold difference from HSV1/Vero cells to EGCG-ester HSV1/Vero cells. These results indicate that EGCG-ester inhibits HSV1 to a great extent and is more effective against HSV1 when compared to EGCG alone.

In summary, both EGCG and EGCG-ester can inhibit HSV1, but EGCG-ester has proven to be more potent compared to EGCG in inhibiting the action against HSV1 infections in vitro. Contrary to EGCG, EGCG-ester is a stable compound and is also stable at vaginal pH and would be an ideal candidate for a topical application. An EGCG ester topical application against HSV1 and possibly HSV2 would benefit millions of people every year. Furthermore, by being able to stop the spread of the disease enables us to possibly stop the link between HSV and HIV. Although further studies need to be conducted in order to completely understand the mode of action of EGCG-ester in humans the results obtained in this study are very promising. The use of natural products can improve the lives of many and thus give patients hope for a better and healthier future.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method for treating herpes simplex virus (HSV) infection in a subject comprising administering to the subject a composition comprising 12.5 μM to 100 μM green tea polyphenol esterified with stearic or palmitic acid at the 4' position and glycerin to treat at least one symptom of HSV infection.

2. The method of claim 1, wherein the composition comprises 0.001% to about 50% w/v of the green tea polyphenol esterified with stearic or palmitic acid at the 4' position.

3. The method of claim 1 wherein the green tea polyphenol is (−)-epigallocatechin-3-gallate esterified at the 4' position with stearic acid.

4. The method of claim 1 wherein the subject is human.

5. The method of claim 1 wherein the composition further comprises an anesthetic.

6. The method of claim 1 wherein the composition is formulated for topical administration.

7. The method of claim 1, wherein the composition is formulated for oral administration.

8. The method of claim 1, wherein the green tea polyphenol is selected from the group consisting of (−)-epicatechin, (−)-epigallocatechin, (−)-epicatechin-3-gallate, enantiomers thereof, isomers thereof, and combinations thereof.

9. The method of claim 1, wherein the HSV is HSV-1.

10. The method of claim 1, wherein the green tea polyphenol is (−)-epigallocatechin -3-gallate esterified at the 4' position with palmitic acid.

* * * * *

SEQUENCE LISTING

```
<160> NUMBER OF SEQ ID NOS: 30

<210> SEQ ID NO 1
<211> LENGTH: 9
<212> TYPE: PRT
```

<213> ORGANISM: herpes simplex virus-1
<220> FEATURE:
<221> NAME/KEY: MISC_FEATURE
<222> LOCATION: (1)..(9)
<223> OTHER INFORMATION: lysine-rich region of glycoprotein B

<400> SEQUENCE: 1

Lys Pro Lys Lys Asn Lys Lys Pro Lys
1 5

<210> SEQ ID NO 2
<211> LENGTH: 24
<212> TYPE: DNA
<213> ORGANISM: Artificial Sequence
<220> FEATURE:
<223> OTHER INFORMATION: Forward primer for HSV1 glycoprotein D

<400> SEQUENCE: 2
agacgtccgg aaacaaccct acaa 24

<210> SEQ ID NO 3
<211> LENGTH: 24
<212> TYPE: DNA
<213> ORGANISM: Artificial Sequence
<220> FEATURE:
<223> OTHER INFORMATION: reverse primer for HSV1 glycoprotein D

<400> SEQUENCE: 3
acacaattcc gcaaatgacc aggg 24

<210> SEQ ID NO 4
<211> LENGTH: 24
<212> TYPE: DNA
<213> ORGANISM: Artificial Sequence
<220> FEATURE:
<223> OTHER INFORMATION: forward primer for HSV1 glycoprotein D

<400> SEQUENCE: 4
ttgtttgtcg tcatagtggg cctc 24

<210> SEQ ID NO 5
<211> LENGTH: 24
<212> TYPE: DNA
<213> ORGANISM: Artificial Sequence
<220> FEATURE:
<223> OTHER INFORMATION: reverse primer for HSV1 glycoprotein D

<400> SEQUENCE: 5
tggatcgacg gtatgtgcca gttt 24

<210> SEQ ID NO 6
<211> LENGTH: 24
<212> TYPE: DNA
<213> ORGANISM: Artificial Sequence
<220> FEATURE:
<223> OTHER INFORMATION: forward primer for HSV1 glycoprotein B

<400> SEQUENCE: 6
agattctgcg gtactgcgat cact 24

<210> SEQ ID NO 7
<211> LENGTH: 24
<212> TYPE: DNA
<213> ORGANISM: Artificial Sequence
<220> FEATURE:
<223> OTHER INFORMATION: reverse primer for HSV1 glycoprotein B

<400> SEQUENCE: 7
acggaacaca aacaagcacg gatg 24

<210> SEQ ID NO 8
<211> LENGTH: 24
<212> TYPE: DNA
<213> ORGANISM: Artificial Sequence
<220> FEATURE:
<223> OTHER INFORMATION: forward primer for HSV1 glycoprotein B

<400> SEQUENCE: 8
agctgattat cgccaccaca ctct 24

<210> SEQ ID NO 9
<211> LENGTH: 24
<212> TYPE: DNA
<213> ORGANISM: Artificial Sequence
<220> FEATURE:
<223> OTHER INFORMATION: reverse primer for HSV1 glycoprotein B

<400> SEQUENCE: 9
tggcgttgat cttgtcgatc acct 24

<210> SEQ ID NO 10
<211> LENGTH: 27
<212> TYPE: DNA
<213> ORGANISM: Artificial Sequence
<220> FEATURE:
<223> OTHER INFORMATION: forward primer for HSV1 glycoprotein B

<400> SEQUENCE: 10
attctcctcc gacgccatat ccacctt 27

<210> SEQ ID NO 11
<211> LENGTH: 25
<212> TYPE: DNA
<213> ORGANISM: Artificial Sequence
<220> FEATURE:
<223> OTHER INFORMATION: reverse primer for HSV1 glycoprotein B

<400> SEQUENCE: 11
agaaagcccc cattggccag gtagt 25

<210> SEQ ID NO 12
<211> LENGTH: 26
<212> TYPE: DNA
<213> ORGANISM: Artificial Sequence
<220> FEATURE:
<223> OTHER INFORMATION: forward primer for GFP

<400> SEQUENCE: 12
gtcaaagctt aagatggtga gcaagg 26

<210> SEQ ID NO 13
<211> LENGTH: 26
<212> TYPE: DNA
<213> ORGANISM: Artificial Sequence
<220> FEATURE:
<223> OTHER INFORMATION: reverse primer for GFP

<400> SEQUENCE: 13
cttgaagctt cttgtacagc tcgtcc 26

<210> SEQ ID NO 14
<211> LENGTH: 23

-continued

<212> TYPE: DNA
<213> ORGANISM: Artificial Sequence
<220> FEATURE:
<223> OTHER INFORMATION: forward primer for GFP

<400> SEQUENCE: 14
gaccctgaag ttcatctgca cca 23

<210> SEQ ID NO 15
<211> LENGTH: 22
<212> TYPE: DNA
<213> ORGANISM: Artificial Sequence
<220> FEATURE:
<223> OTHER INFORMATION: reverse primer for GFP

<400> SEQUENCE: 15
aactccagca ggaccatgtg at 22

<210> SEQ ID NO 16
<211> LENGTH: 24
<212> TYPE: DNA
<213> ORGANISM: Artificial Sequence
<220> FEATURE:
<223> OTHER INFORMATION: forward primer for HSV1 tegument protein
VP11/12

<400> SEQUENCE: 16
accaagcctt gatgctcaac tcca 24

<210> SEQ ID NO 17
<211> LENGTH: 23
<212> TYPE: DNA
<213> ORGANISM: Artificial Sequence
<220> FEATURE:
<223> OTHER INFORMATION: reverse primer for HSV1 tegument protein
VP11/12

<400> SEQUENCE: 17
caacacggtt cccgagagtt tga 23

<210> SEQ ID NO 18
<211> LENGTH: 24
<212> TYPE: DNA
<213> ORGANISM: Artificial Sequence
<220> FEATURE:
<223> OTHER INFORMATION: forward primer for HSV1 tegument protein
VP11/12

<400> SEQUENCE: 18
accaagcctt gatgctcaac tcca 24

<210> SEQ ID NO 19
<211> LENGTH: 24
<212> TYPE: DNA
<213> ORGANISM: Artificial Sequence
<220> FEATURE:
<223> OTHER INFORMATION: reverse primer for HSV1 tegument protein
VP11/12

<400> SEQUENCE: 19
acacaacacg gttcccgaga gttt 24

<210> SEQ ID NO 20
<211> LENGTH: 21
<212> TYPE: DNA
<213> ORGANISM: Artificial Sequence
<220> FEATURE:

-continued

<223> OTHER INFORMATION: forward primer for HSV1 glycoprotein D

<400> SEQUENCE: 20
caaccctaca acctgaccat c 21

<210> SEQ ID NO 21
<211> LENGTH: 21
<212> TYPE: DNA
<213> ORGANISM: Artificial Sequence
<220> FEATURE:
<223> OTHER INFORMATION: reverse primer for HSV1 glycoprotein D

<400> SEQUENCE: 21
ttgtaggagc attcggtgta c 21

<210> SEQ ID NO 22
<211> LENGTH: 734
<212> TYPE: DNA
<213> ORGANISM: Artificial Sequence
<220> FEATURE:
<223> OTHER INFORMATION: PCR fragment of HSV1 glycoprotein D

<400> SEQUENCE: 22
gtcatgccat gctcggatgg gaggcactgt gctatcccca tcacggtcat ggagtacacc 60
gaatgctcct acaacaagtc tctgggggcc tgtcccatcc gaacgcagcc ccgctggaac 120
tactatgaca gcttcagcgc cgtcagcgag gataacctgg ggttcctgat gcacgccccc 180
gcgtttgaga ccgccggcac gtacctgcgg ctcgtgaaga taaacgactg gacggagatt 240
acacagttta tcctggagca ccgagccaag ggctcctgta agtacgccct cccgctgcgc 300 atcccccccgt cagcctgcct ctccccccag gcctaccagc agggggtgac ggtggacagc 360
atcgggatgc tgccccgctt catccccgag aaccagcgca ccgtcgccgt atacagcttg 420
aagatcgccg ggtggcacgg gcccaaggcc ccatacacga gcaccctgct gcccccggag 480
ctgtccgaga cccccaacgc cacgcagcca gaactcgccc cggaagaccc cgaggattcg 540
gccctcttgg aggaccccgt ggggacggtg gcgccgcaaa tcccaccaaa ctggcacatc 600
ccgtcgatcc aggacgccgc gacgccttac catcccccgg ccaccccgaa caacatgggc 660
ctgatcgccg gcgcggtggg cggcagtctc ctggcagccc tggtcattgg ggaaattttt 720
tgtatataaa aaaa 734

<210> SEQ ID NO 23
<211> LENGTH: 947
<212> TYPE: DNA
<213> ORGANISM: Artificial Sequence
<220> FEATURE:
<223> OTHER INFORMATION: PCR fragment of HSV1 glycoprotein D

<400> SEQUENCE: 23
aggctgcgcg atatgcttgg cggatgctct ctcagatggc cgaccccaat cgctttcgcg 60
gcaaagacct tccggtcctg gaccagctga ccgaccctcc gggggtccgg cgcgtgtacc 120
acatccaggc gggcctaccg gacccgttcc agccccccag cctcccgatc acggtttact 180
acgccgtgtt ggagcgcgcc tgccgcagcg tgctcctaaa cgcaccgtcg ggaggccccc 240
ccagattgtc cggcgggggc cctccgaagg acgttccgga aacaacccta caacctgacc 300
atcgcttggt ttcggatggg aggcaactgt gctatcccca tcacggtcat ggagtacacc 360
gaaatgctcc tacaacaagt ctctgggggc ctgtcccatc cgaaaacggg ccccgcggga 420
aaaataaaaa aaaaaatttt ccggggccgg aggaaaaaaa accgggggtt ttataaaggg 480

-continued gggggggtt gaaaaaatac gccggcacgt acctgcggtt cgtggaagat aaaaagtgac 540
ggagattaat tttattgggc cggccgggcc cgtagtacgc cctccgctgc gcatcccccc 600
cgtcagcctt gcctctcccc cccaggccta acagcaaggg gggtgaacgg tgggaacagc 660
aatcggaatg gctggccccg ctttcaatcc cccgagaaaa ccaagccgca accggtcgcc 720
cggtaattac aggcttggaa aggatcgccg ggtagacaac ggggccccaa aggccccata 780
caacgtagtc acccttggct tgccgcccgg agctgttccg agaacttctc aatggctcac 840
gcgcagccgg gaaagttcgt ctccggcaag aacacgagag aattcgtccc atcattggaa 900
gaggcctagt gcgctacggt gttgcgcgct gtcatcatga ttatgtc 947

<210> SEQ ID NO 24
<211> LENGTH: 425
<212> TYPE: DNA
<213> ORGANISM: Artificial Sequence
<220> FEATURE:
<223> OTHER INFORMATION: PCR fragment of HSV1 glycoprotein B

<400> SEQUENCE: 24
caggcatcac accatcacag accatcatcg tagagtaccg ccgtccccca gcgtgcaggc 60
ggcggccgcg tggtagagca ggcgggggg cgtggagcgt ggcagaccgc catggacgcg 120
tggacgcgca tccgtgcgcg ttttcctcca tgtaggggaa cctgaaactg gtagcggccc 180
gtaaggccgc ccgcccagga acatgtgggg gttaagcata gcaagtacta cggcagtgcc 240
gggtaacacc gtgtgtttca gcgcggcaac tggcgcagcc ttgtgggtag caaacacgcc 300
gtgcccggcc tttatttttg acggacccgg cagatcgttc aagccggacg cgggccgggt 360
ttagtagcgc ggcagggacc tcggcgagga gacaggaagc tcgctatcag actatccggg 420
taatt 425

<210> SEQ ID NO 25
<211> LENGTH: 967
<212> TYPE: DNA
<213> ORGANISM: Artificial Sequence
<220> FEATURE:
<223> OTHER INFORMATION: PCR fragment of HSV1 glycoprotein B

<400> SEQUENCE: 25
ttctcctaac gggtgcgcgg actcgagagc gccgcccgga ctgcagccgc cgacctccga 60
agtcgttaca gcaagacgcg cggcgaatat ctcacgtacg actccgactg tccgctgttg 120
gccatcgtcg agagcgcccc cgacggctgt atcggccccc ggtcggtcgt ggtctacgac 180
cgcgaagttt ttctcgatcc tctactcggt cctccagcac ctcgccccca ggctacctga 240
cgggggttac gacgggcccc gtagccccgg cattgcacaa ggcccccccc tcgggggggc 300
cgccgggggt tcgccgttag ggtccctttg ggggtggagg gggggtttg ggtttttcgg 360 gtttttgcc cattttcccg ttacggcttg gggttggggg cggccccagg gggggggagg 420
gggggggatt ggaaattccg ccggcccccc cccttgtggc ccccccccaa gggggggggg 480
cgggaagggg aaaaaaaaaa aaaaaccaaa aaaacccggg gccccccccc cccccacccg 540
aaaaaagcca aattggtgga gggggggggg ccccccctggg gggggacccc gtgggggaaa 600
ttggggggta aaaaaacccc ttttattttc ttgggggggg cccccccccc agggggcctg 660
gggggtccaa tttaagaaac ccacaaaatt ttccgtaccg gcccaaggat acaaaaattt 720
accgaggacc cccggggggg tttttttaga aaaaaaaccc cccccccaaa aatttcgagg 780

-continued

```
gcccaaagtg taaaaaaaaa acgccctgcc gttttttaca gaatattttt ctttgccgaa    840

accttaactc ctccaatttt taaggggaga ttttttttaaa gacacgcccc ctctcttcct    900

tttttcgagg agggggtaaa tagaacataa gtatcgcgcc cataaaaaaa aagatagaat    960

aaaaagg                                                               967
```

<210> SEQ ID NO 26
<211> LENGTH: 156
<212> TYPE: DNA
<213> ORGANISM: Artificial Sequence
<220> FEATURE:
<223> OTHER INFORMATION: PCR fragment of HSV1 glycoprotein B

<400> SEQUENCE: 26

```
ccaccagacc gagtacccgc tctcgcgcgt gacctggggg actgcatcgg caaggacgcc     60

cgcgacgcca tggaccgcat cttcgcccgc aggtacaacg cgacgcacat caaggtgggc    120

cagccgcagt actacctggc caatgggggc tttctt                              156
```

<210> SEQ ID NO 27
<211> LENGTH: 714
<212> TYPE: DNA
<213> ORGANISM: Artificial Sequence
<220> FEATURE:
<223> OTHER INFORMATION: PCR fragment of GFP

<400> SEQUENCE: 27

```
gaggccggat cacgggtgtg ccatcctggt cgagctggac ggcgacgtaa cggccacaag     60

ttcagcgtgt ccggcgaggg cgagggcgat gccacctacg gcaagctgac cctgaagttc    120

atctgcacca ccggcaagct gcccgtgccc tggcccaccc tcgtgaccac cctgacctac    180

ggcgtgcagt gcttcagccg ctaccccgac cacatgaagc agcacgactt cttcaagtcc    240

gccatgcccg aaggctacgt ccaggagcgc accatcttct tcaaggacga cggcaactac    300

aagacccgcg ccgaggtgaa gttcgagggc gacaccctgg tgaaccgcat cgagctgaag    360

ggcatcgact tcaaggagga cggcaacatc ctggggcaca agctggagta caactacaac    420

agccacaacg tctatatcat ggccgacaag cagaagaacg gcatcaaggt gaacttcaag    480

atccgccaca acatcgagga cggcagcgtg cagctcgccg accactacca gcagaacacc    540

cccatcggcg acggccccgt gctgctgccc gacaaccact acctgagcac ccagtccgcc    600

ctgagcaaag accccaacga gaagcgcgat cacatggtcc tgctggagtt cgtgaccgcc    660

gccgggatca ctctcggcat ggacgagctg tactgaaaac tctctttgag gaaa          714
```

<210> SEQ ID NO 28
<211> LENGTH: 513
<212> TYPE: DNA
<213> ORGANISM: Artificial Sequence
<220> FEATURE:
<223> OTHER INFORMATION: PCR fragment of GFP

<400> SEQUENCE: 28

```
cgccgccgtc ctggcccacc ctcgtgacca ccctgaccta cggcgtgcag tgcttcagcc     60

gctaccccga ccacaagaag cagcacgact tcttcaagtc cgccatgccc gaaggctacg    120

tccaggagcg caccatcttc ttcaaggacg acggcaacta caagacccgc gccgaggtga    180

agttcgaggg cgacaccctg gtgaaccgca tcgagctgaa gggcatcgac ttcaaggagg    240

acggcaacat cctggggcac aagctggagt acaactacaa cagccacaac gtctatatca    300

tggccgacaa gcagaagaac ggcatcaagg tgaacttcaa gatccgccac aacatcgagg    360
```

-continued acggcagcgt gcagctcgcc gaccactacc agcagaacac ccccatcggc gacggccccg 420
tgctgctgcc cgacaaccac tacctgagca cccagtccgc cctgagcaaa gaccccaacg 480
agaagcgcga tcacatggtc tgccgggagt taa 513

<210> SEQ ID NO 29
<211> LENGTH: 964
<212> TYPE: DNA
<213> ORGANISM: Artificial Sequence
<220> FEATURE:
<223> OTHER INFORMATION: PCR fragment of HSV1 VP11/12

<400> SEQUENCE: 29
tccgcgtggg ggcgtcatcg tggggacagg ggggcggtgg tccgacagaa cgctcctggc 60
tgtccaccgc ggcccgcaga tactcgttgt tcaggctgtc ggtggcccag acgccgtacc 120
cggtgagggt cgcgttgatg atatactggg cgtggtgatg gacgatcgac agaacctcca 180
ccgtggatac cacggtatcc acggtcccgt acgtaccgcc gctccgcttg ccggtctgcc 240
acaggttggc taggcacgtc aggtggccca ggacgtcgct gaccgccgcc ctgagcgcca 300
tgcactgcat ggagccggtc gtgccgctgg aaccccggtc caaatggcgc gcgaacgttt 360
ccgcgggccc cttccgggct gccgccgaag cggaaggaac cgggcaattg gagggactca 420
gccggtgaca tacgtgcttg tccgtcgtca acggcatcca ggaggcccac cggtacagca 480
cggaaacgta ggccaggagc tccgttaagc cgcattgcgg tgtcggtcct gggacgtttt 540 gggcccccg gggcgcataa ggaacatgta ctgctgaatc caatggaggg gcgtcgcgca 600
gccggcccac ggtggcggct tatttgggcc cccgcgcccc cgccttttaa acggggtgcc 660
gcgccaagcc acttttgggg ccgggttggc ccgcaacaac cacgtgaaag gctggggctc 720
cgcagtcgcc cacggggtcc ttcgggaaac gtcaaggccg gctgggccac aaccgtctgc 780
aggtacttca agtactgcgt ggaggatggc gcgctcaaac tgggccgctc tggtcagctc 840
caccttcgcc cagcgctggg tgtcggtctg aagcgtactg ccggatgtac tcgttagtgc 900
aggtcgcttg gcgagcccgt cacgatctag actatcgtgg ggagagagtg tgtagtatat 960
ataa 964

<210> SEQ ID NO 30
<211> LENGTH: 958
<212> TYPE: DNA
<213> ORGANISM: Artificial Sequence
<220> FEATURE:
<223> OTHER INFORMATION: PCR fragment of HSV1 VP11/12

<400> SEQUENCE: 30
ttcagctggg ggcgtcatcg tgcggacagg ggggcggtgg tccgacagaa acgctcctgg 60
ctgtccaccg cggcccgcag atactcgttg ttcaggctgt cggtggccca gacgccgtac 120
ccggtgaggg tcgcgttgat gatatactgg gcgtggtgat ggacgatcga cagaacctcc 180
accgtggata ccacggtatc cacggtcccg tacgtaccgc cgctccgctt gccggtctgc 240
cacaggttgg ctaggcacgt caggtggccc aggacgtcgc tgaccgccgc cctgagcgcc 300
atgcactgca tggagccggt cgtgccgctg ggaccccggt ccagatgggg gcgcgaacgt 360
ttccgggggg cccctccggc ctgccgccga gcggaaggaa ccgggcaatt ggagggactc 420
agccggggac atacgtgctt tgtccgtcgt ccacagcatc agggacgccc acggttacag 480
cacggaaacg tagcccagga cctctttgac ccgcagtgcg gtttcggtcc tggggcgact 540

-continued

```
tggtcccccc gggccccata aggaacatgt actgctgaat ccaatggaag ggcgtcggcc    600

agcccggcca gggtggcggc taatttgggc cgccggcgcc cccgcttttg aacgggggtg    660

cgcgccagcg tttttggggc cgggggtggg cccgcgccac cacgtgaagg ccggggtccg    720

cagtcccccc acggggtctt ggggaatgtc agggcggtgg gaaccaccgt tcggcggtac    780

tttccggaac gggcgtgaag gatggcgcgg ctcaaactgg accgcggggc agtctccact    840

ttcgcccaag cgcctgggtg tgcggccgaa agcatatgcc ggaatgtact cgtagtgacg    900

gttcgctggc gagccggtca cgatcaatct ctcggagacg tggtgtgata gtatataa      958
```